United States Patent
Ripka et al.

(10) Patent No.: US 8,343,973 B2
(45) Date of Patent: Jan. 1, 2013

(54) PHENOXYMETHYL HETEROCYCLIC COMPOUNDS

(75) Inventors: Amy Ripka, Reading, MA (US); Gideon Shapiro, Gainsville, FL (US); Richard Chesworth, Boston, MA (US)

(73) Assignee: EnVivo Pharmaceuticals, Inc., Watertown, MA (US)

( * ) Notice: Subject to any disclaimer, the term of this patent is extended or adjusted under 35 U.S.C. 154(b) by 446 days.

(21) Appl. No.: 12/642,026

(22) Filed: Dec. 18, 2009

(65) Prior Publication Data

US 2010/0292238 A1    Nov. 18, 2010

Related U.S. Application Data

(60) Provisional application No. 61/176,413, filed on May 7, 2009.

(51) Int. Cl.
    C07D 487/04    (2006.01)
    A61K 31/5025   (2006.01)
    A61P 25/28     (2006.01)

(52) U.S. Cl. ........................... 514/248; 544/236

(58) Field of Classification Search .............. 544/236; 514/248

See application file for complete search history.

(56) References Cited

U.S. PATENT DOCUMENTS

| 8,071,595 B2 | 12/2011 | Ripka et al. |
| 2003/0032579 A1 | 2/2003 | Lebel et al. |
| 2011/0053905 A1* | 3/2011 | Guo et al. .............. 514/210.18 |
| 2011/0183976 A1 | 7/2011 | Ripka et al. |
| 2012/0040979 A1* | 2/2012 | Falco et al. .............. 514/233.2 |
| 2012/0046320 A1* | 2/2012 | KC et al. .............. 514/338 |
| 2012/0053202 A1* | 3/2012 | De Peretti et al. .............. 514/300 |

FOREIGN PATENT DOCUMENTS

| EP | 1541149 | 6/2005 |
| WO | WO2006/072828 | 7/2006 |
| WO | WO2007/077490 | 7/2007 |
| WO | WO2007/129183 | 11/2007 |
| WO | WO 2008/033455 | 3/2008 |
| WO | WO2009/158393 | 12/2009 |
| WO | WO2009/158473 | 12/2009 |

OTHER PUBLICATIONS

U.S. Appl. No. 13/290,527, filed Nov. 7, 2011, Ripka et al.

Davis, J.M et al. "Dose response and dose equivalence of antipsychotics." Journal of Clinical Psychopharmacology, Apr. 2004, 24 (2),192-208.
Fernandez et al "Treatment of psychosis in Parkinson's disease: Safety considerations." Drug Safety, 2003, 26 (9), 643-659.
Fujishige et al. "Cloning and characterization of a novel human phosphodiesterase that hydrolyzes both cAMP and cGMP (PDE10A)" J. Biol. Chem. Jun. 1999,274, 18438-18445.
Handa et al. "Crystal structure of the GAF-B domain from human phosphodiesterase 10A complexed with its ligand, cAMP" J Biol. Chem. Jul. 2008, pp. 19657-19664.
Kostowski et. al "Papaverine drug induced stereotypy and catalepsy and biogenic aminesin the brain of the rat" Pharmacol. Biochem. Behav. Jul. 1976, 5, 15-17.
Lazorthes et al. "Advances in Drug Delivery Systems and Applications in Neurosurgery." Advances and Technical Standards in Neurosurgery, vol. 18, 1991. 143-192.
Loughney et al. "Isolation and characterization of PDE10A, a novel human 3',5'-cyclicnucleotide phosphodiesterase" Gene, Jun. 1999, vol. 234, No. 1. pp. 109-117.
Meyer et al "The Clinical Antipsychotic Trials Of Intervention Effectiveness (CATIE) Schizophrenia Trial: clinical comparison of subgroups with and without the metabolic syndrome." Schizophrenia Research, 2005, 80 (1), 9-43.
Minto, J. et al., Pharmacokinetics and Pharmacodynamics of Nandrolone Esters in Oil Vehicle: Effects of Ester, Injection Site and Injection Volume, Pharmcol. Exp. Ther. vol. 291, No. 1. Apr. 1997. pp. 93-102.
Navidpour et al., Design and synthesis of new water-soluble tetrazolide derivatives of celecoxib and refecoxib as selective cyclooxygenase-2 (COX-2) inhibitors, 2006, Bioorganic & Medicinal Chemistry Letters, 16, 4483-4487.
Ommaya et al. "Implantable Devices for Chronic Access and Drug Delivery to the Central Nervous System", Cancer Drug Delivery, vol. 1, No. 2, 1984. pp. 169-179.
Patani et al., Bioisosterism: A Rational Approach in Drug Design, 1996, Chem. Rev., vol. 96, No. 8. pp. 3147-3176.
Soderling and Beavo "Regulation of cAMP and cGMP signaling: New phosphodiesterases and new functions," Curr. Opin. Cell Biol., Apr. 2000, vol. 12, No. 2. pp. 174-179.
Soderling et al. "Isolation and characterization of a dual-substrate phosphodiesterase gene family: PDE10A" Proc. Natl Sci. Jun. 8, 1999, vol. 96, No. 12. pp. 7071-7076.

* cited by examiner

*Primary Examiner* — Susanna Moore
*Assistant Examiner* — Cecilia M Jaisle
(74) *Attorney, Agent, or Firm* — Wilmer Cutler Pickering Hale and Dorr LLP

(57) ABSTRACT

Phenoxymethyl compounds that inhibit at least one phosphodiesterase 10 are described as are pharmaceutical compositions containing such compounds an methods for treating various CNS disorders by administering such compounds to a patient in need thereof.

4 Claims, No Drawings

PHENOXYMETHYL HETEROCYCLIC COMPOUNDS

This application claims priority to U.S. Provisional Application 61/176,413, which was filed on May 7, 2009.

BACKGROUND

Cyclic phosphodiesterases are intracellular enzymes which, through the hydrolysis of cyclic nucleotides cAMP and cGMP, regulate the levels of these mono phosphate nucleotides which serve as second messengers in the signaling cascade of G-protein coupled receptors. In neurons, PDEs also play a role in the regulation of downstream cGMP and cAMP dependent kinases which phosphorylate proteins involved in the regulation of synaptic transmission and homeostasis. To date, eleven different PDE families have been identified which are encoded by 21 genes. The PDEs contain a variable N-terminal regulatory domain and a highly conserved C-terminal catalytic domain and differ in their substrate specificity, expression and localization in cellular and tissue compartments, including the CNS.

The discovery of a new PDE family, PDE10, was reported simultaneously by three groups in 1999 (Soderling et al. "Isolation and characterization of a dual-substrate phosphodiesterase gene family: PDE10A" *Proc. Natl. Sci.* 1999, 96, 7071-7076; Loughney et al. "Isolation and characterization of PDE10A, a novel human 3',5'-cyclic nucleotide phosphodiesterase" *Gene* 1999, 234, 109-117; Fujishige et al. "Cloning and characterization of a novel human phosphodiesterase that hydrolyzes both cAMP and cGMP (PDE10A)" *J. Biol. Chem.* 1999, 274, 18438-18445). The human PDE10 sequence is highly homologous to both the rat and mouse variants with 95% amino acid identity overall, and 98% identity conserved in the catalytic region.

PDE10 is primarily expressed in the brain (caudate nucleus and putamen) and is highly localized in the medium spiny neurons of the striatum, which is one of the principal inputs to the basal ganglia. This localization of PDE10 has led to speculation that it may influence the dopaminergic and glutamatergic pathways both which play roles in the pathology of various psychotic and neurodegenerative disorders.

PDE10 hydrolyzes both cAMP ($K_m$=0.05 uM) and cGMP ($K_m$=3 uM) (Soderling et al. "Isolation and Characterization of a dual-substrate phosphodiesterase gene family: PDE10." *Proc. Natl. Sci. USA* 1999, 96(12), 7071-7076). In addition, PDE10 has a five-fold greater $V_{max}$ for cGMP than for cAMP and these in vitro kinetic data have lead to the speculation that PDE10 may act as a cAMP-inhibited cGMP phosphodiesterase in vivo (Soderling and Beavo "Regulation of cAMP and cGMP signaling: New phosphodiesterases and new functions," *Curr. Opin. Cell Biol.*, 2000, 12, 174-179).

PDE10 is also one of five phosphodiesterase members to contain a tandem GAF domain at their N-terminus. It is differentiated by the fact that the other GAF containing PDEs (PDE2, 5, 6, and 11) bind cGMP while recent data points to the tight binding of cAMP to the GAF domain of PDE10 (Handa et al. "Crystal structure of the GAF-B domain from human phosphodiesterase 10A complexed with its ligand, cAMP" *J. Biol. Chem.* 2008, May 13, ePub).

PDE10 inhibitors have been disclosed for the treatment of a variety of neurological and psychiatric disorders including Parkinson's disease, schizophrenia, Huntington's disease, delusional disorders, drug-induced psychoses, obsessive compulsive and panic disorders (US Patent Application 2003/0032579). Studies in rats (Kostowski et. al "Papaverine drug induced stereotypy and catalepsy and biogenic amines in the brain of the rat" *Pharmacol. Biochem. Behav.* 1976, 5, 15-17) have showed that papaverine, a selective PDE10 inhibitor, reduces apomorphine induced stereotypes and rat brain dopamine levels and increases haloperidol induced catalepsy. This experiment lends support to the use of a PDE10 inhibitor as an antipsychotic since similar trends are seen with known, marketed antipsychotics.

Antipsychotic medications are the mainstay of current treatment for schizophrenia. Conventional or classic antipsychotics, typified by haloperidol, were introduced in the mid-1950s and have a proven track record over the last half century in the treatment of schizophrenia. While these drugs are effective against the positive, psychotic symptoms of schizophrenia, they show little benefit in alleviating negative symptoms or the cognitive impairment associated with the disease. In addition, drugs such as haloperidol have extreme side effects such as extrapyramidal symptoms (EPS) due to their specific dopamine D2 receptor interaction. An even more severe condition characterized by significant, prolonged, abnormal motor movements known as tardive dyskinesia also may emerge with prolonged classic antipsychotic treatment.

The 1990s saw the development of several new drugs for schizophrenia, referred to as atypical antipsychotics, typified by risperidone and olanzapine and most effectively, clozapine. These atypical antipsychotics are generally characterized by effectiveness against both the positive and negative symptoms associated with schizophrenia, but have little effectiveness against cognitive deficiencies and persisting cognitive impairment remain a serious public health concern (Davis, J. M et al. "Dose response and dose equivalence of antipsychotics." *Journal of Clinical Psychopharmacology*, 2004, 24 (2), 192-208; Friedman, J. H. et al "Treatment of psychosis in Parkinson's disease: Safety considerations." *Drug Safety*, 2003, 26 (9), 643-659). In addition, the atypical antipsychotic agents, while effective in treating the positive and, to some degree, negative symptoms of schizophrenia, have significant side effects. For example, clozapine which is one of the most clinically effective antipsychotic drugs shows agranulocytosis in approximately 1.5% of patients with fatalities due to this side effect being observed. Other atypical antipsychotic drugs have significant side effects including metabolic side effects (type 2 diabetes, significant weight gain, and dyslipidemia), sexual dysfunction, sedation, and potential cardiovascular side effects that compromise their clinically effectiveness. In the large, recently published NIH sponsored CAT1'-study, (Lieberman et al "The Clinical Antipsychotic Trials Of Intervention Effectiveness (CATIE) Schizophrenia Trial: clinical comparison of subgroups with and without the metabolic syndrome." *Schizophrenia Research*, 2005, 80 (1), 9-43) 74% of patients discontinued use of their antipsychotic medication within 18 months due to a number of factors including poor tolerability or incomplete efficacy. Therefore, a substantial clinical need still exists for more effective and better tolerated antipsychotic mediations possibly through the use of PDE10 inhibitors.

BRIEF SUMMARY

The disclosure relates compounds which are inhibitors of phosphodiesterase 10. The disclosure further relates to processes, pharmaceutical compositions, pharmaceutical preparations and pharmaceutical use of the compounds in the treatment of mammals, including human(s) for central nervous system (CNS) disorders and other disorders which may affect CNS function. The disclosure also relates to methods for treating neurological, neurodegenerative and psychiatric disorders including but not limited to those comprising cognitive deficits or schizophrenic symptoms.

Described herein are compounds of Formula (I) that are inhibitors of at least one phosphodiesterase 10:

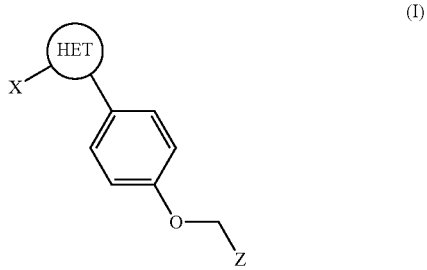

Wherein:
HET is a heterocyclic ring selected from Formulas A29, A31 and A39 below

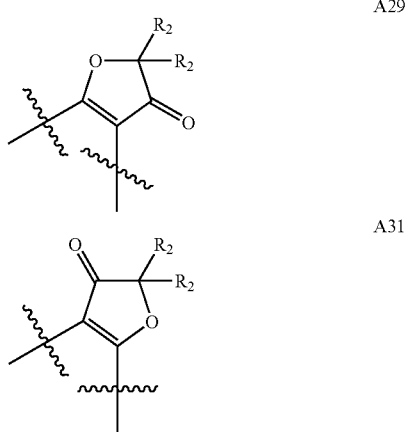

and the left most radical is connected to the X group;
X is selected from optionally substituted aryl and optionally substituted heteroaryl;
Z is optionally substituted heteroaryl;
Each $R_2$ is independently selected from $C_1$-$C_4$ alkyl, or two $R_2$ groups taken together with the carbon to which they are attached form a 3 membered cycloalkyl ring;

In one embodiment, alkyl groups are fully saturated whether present on their own or as part of another group (e.g. alkylamino or alkoxy).

In certain embodiments, substituent groups are not further substituted.

In various embodiments, any group that is defined as being optionally substituted can be singly or independently multiply optionally substituted.

In one embodiment, HET is selected from Formulas A29 and A31.

In another embodiment, HET is Formula A29.

In another embodiment, HET is Formula A31.

In one embodiment, X is selected from a monocyclic heteroaryl having 5 ring atoms selected from C, O, S and N provided the total number of ring heteroatoms is less than or equal to four and where no more than one of the total number of heteroatoms is oxygen or sulfur, and a monocyclic aromatic ring having 6 atoms selected from C and N provided that not more than 3 ring atoms are N, and where said ring may be optionally and independently substituted with up to two groups selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, halogen, cyano, alkylsulfonyl and nitro. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, 1,2,3,4-oxatriazolyl, 1,2,3,5-oxatriazolyl, 1,2,3,4-thiatriazolyl, 1,2,3,5-thiatriazolyl, 1,2,3-triazinyl, 1,2,4-triazinyl, 1,3,5-triazinyl, pyridinyl, pyrazinyl, pyridazinyl and pyrimidinyl.

In a further embodiment, X is a monocyclic heteroaryl having 6 ring atoms selected from C and N provided that not more than 3 ring atoms are N, and where said ring may be optionally and independently substituted with up to two groups selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, halogen, cyano, alkylsulfonyl and nitro. Examples include but are not limited to 1,2,3-triazinyl, 1,2,4-triazinyl, 1,3,5-triazinyl, pyridinyl, pyrazinyl, pyridazinyl and pyrimidinyl.

In a further embodiment, X is a monocyclic heteroaryl having 5 ring atoms selected from C, O, S, and N, provided the total number of ring heteroatoms is less than or equal to four and where no more than one of the total number of heteroatoms is oxygen or sulfur and where said ring may be optionally and independently substituted with up to two groups selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, halogen, cyano, alkylsulfonyl and nitro. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, 1,2,3,4-oxatriazolyl, 1,2,3,5-oxatriazolyl, 1,2,3,4-thiatriazolyl, 1,2,3,5-thiatriazolyl.

In a further embodiment, X is 4-pyridinyl optionally substituted with one group selected from $C_1$-$C_4$ alkyl, cyclopropyl, cyclopropyloxy, cyclopropylmethyl, $C_1$-$C_4$ alkoxy, $CF_3$, amino, alkylamino, dialkylamino, thioalkyl, halogen, alkylsulfonyl and cyano.

In a further embodiment, X is 4-pyridinyl.

In another embodiment X is selected from restricted phenyl.

In a further embodiment, X is selected from a 3,4-disubstituted phenyl, 4-substituted phenyl, and 4-pyridinyl.

In a further embodiment, X is selected from a 3,4-disubstituted phenyl and 4-substituted phenyl.

In another embodiment, X is selected from 4-pyridinyl and 4-substituted phenyl.

In an additional embodiment, X is 4-substituted phenyl.

In a further embodiment, X is 4-methoxyphenyl.

In another embodiment, X is 4-chlorophenyl.

In another embodiment, X is 4-cyanophenyl.

In one embodiment, Z is heteroaryl but is not quinolinyl or pyridyl.

In one embodiment, Z is heteroaryl but is not quinolinyl.

In one embodiment, Z is heteroaryl but is not pyridyl.

In one embodiment, Z is not pyridin-2-yl.

In one embodiment, Z is not pyridinyl.

In another embodiment, Z is selected from pyridin-2-yl, imidazo[1,2-a]pyridin-2-yl, imidazo[1,2-b]pyridazin-2-yl, and imidazo[1,2-b]pyridazin-6-yl all of which may be optionally substituted with up to 2 substituents independently selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, halogen, cyano, alkylsulfonyl and nitro.

In a further embodiment, Z is selected from imidazo[1,2-a]pyridin-2-yl, imidazo[1,2-b]pyridazin-2-yl, and imidazo[1,2-b]pyridazin-6-yl all of which may be optionally substituted with up to 2 substituents independently selected from $C_1$-$C_4$ alkyl, $C_1$-$C_4$ alkoxy, $C_3$-$C_6$ cycloalkyl, $C_3$-$C_6$ cycloalkyloxy, cycloalkylalkyl, cycloalkylalkoxy, halogen, alkylsulfonyl and cyano.

In a further embodiment, Z is a 3,5-disubstituted-pyridin-2-yl with each substituent being independently selected from $C_1$-$C_4$ alkyl, $C_1$-$C_4$ alkoxy, $C_3$-$C_6$ cycloalkyl, $C_3$-$C_6$ cycloalkyloxy, cycloalkylalkyl, cycloalkylalkoxy, halogen, alkylsulfonyl and cyano.

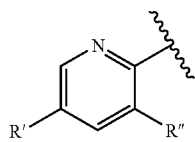

In a further embodiment, Z is 5-substituted-pyridin-2-yl with the substituent being independently selected from $C_1$-$C_4$ alkyl, $C_1$-$C_4$ alkoxy, $C_3$-$C_6$ cycloalkyl, $C_3$-$C_6$ cycloalkyloxy, cycloalkylalkyl, cycloalkylalkoxy, halogen, alkylsulfonyl and cyano.

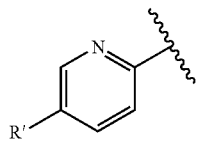

In an additional embodiment, Z is imidazo[1,2-a]pyridin-2-yl substituted with up to 2 substituents independently selected from $C_1$-$C_4$ alkyl, $C_1$-$C_4$ alkoxy, $C_3$-$C_6$ cycloalkyl, $C_3$-$C_6$ cycloalkyloxy, cycloalkylalkyl, cycloalkylalkoxy, halogen, alkylsulfonyl and cyano.

In an additional embodiment, Z is imidazo[1,2-b]pyridazin-2-yl substituted with up to 2 substituents independently selected from $C_1$-$C_4$ alkyl, $C_1$-$C_4$ alkoxy, $C_3$-$C_6$ cycloalkyl, $C_3$-$C_6$ cycloalkyloxy, cycloalkylalkyl, cycloalkylalkoxy, halogen, alkylsulfonyl and cyano.

In an additional embodiment, Z is imidazo[1,2-b]pyridazin-6-yl substituted with up to 2 substituents independently selected from $C_1$-$C_4$ alkyl, $C_1$-$C_4$ alkoxy, $C_3$-$C_6$ cycloalkyl, $C_3$-$C_6$ cycloalkyloxy, cycloalkylalkyl, cycloalkylalkoxy, halogen, alkylsulfonyl and cyano.

In a further embodiment, any Z substituent may be unsubstituted.

In one embodiment, $R_2$ is $C_1$-$C_4$ alkyl.

In another embodiment, $R_2$ is methyl.

In another embodiment, two $R_2$ groups taken together form a 3 membered cycloalkyl ring.

Compounds of the disclosure may contain asymmetric centers and exist as different enantiomers or diastereomers or a combination of these therein. All enantiomeric, diastereomeric forms of Formula (I) are embodied herein.

Compounds in the disclosure may be in the form of pharmaceutically acceptable salts. The phrase "pharmaceutically acceptable" refers to salts prepared from pharmaceutically acceptable non-toxic bases and acids, including inorganic and organic bases and inorganic and organic acids. Salts derived from inorganic bases include lithium, sodium, potassium, magnesium, calcium and zinc. Salts derived from organic bases include ammonia, primary, secondary and tertiary amines, and amino acids. Salts derived from inorganic acids include sulfuric, hydrochloric, phosphoric, hydrobromic. Salts derived from organic acids include $C_{1-6}$ alkyl carboxylic acids, di-carboxylic acids and tricarboxylic acids such as acetic acid, proprionic acid, fumaric acid, maleic acid, succinic acid, tartaric acid, adipic acid and citric acid, and alkylsulfonic acids such as methanesulphonic, and aryl sulfonic acids such as para-tolouene sulfonic acid and benzene sulfonic acid.

Compounds in the disclosure may be in the form of a solvate. This occurs when a compound of Formula (I) has an energetically favorable interaction with a solvent, crystallizes in a manner that it incorporates solvent molecules into the crystal lattice or a complex is formed with solvent molecules in the solid or liquid state. Examples of solvents forming solvates are water (hydrates), MeOH, EtOH, iPrOH, and acetone.

Compounds in the disclosure may exist in different crystal forms known as polymorphs. Polymorphism is the ability of a substance to exist in two or more crystalline phases that have different arrangements and/or conformations of the molecule in the crystal lattice.

Compounds in the disclosure may exist as isotopically labeled compounds of Formula (I) where one or more atoms are replaced by atoms having the same atomic number but a different atomic mass from the atomic mass which is predominantly seen in nature. Examples of isotopes include, but are not limited to hydrogen isotopes (deuterium, tritium), carbon isotopes ($^{11}C$, $^{13}C$, $^{14}C$) and nitrogen isotopes ($^{13}N$, $^{15}N$). For example, substitution with heavier isotopes such as deuterium ($^2H$) may offer certain therapeutic advantages resulting from greater metabolic stability which could be preferable and lead to longer in vivo half-life or dose reduction in a mammal or human.

Prodrugs of compounds embodied by Formula (I) are also within the scope of this disclosure. Particular derivatives of compounds of Formula (I) which may have little to negligible pharmacological activity themselves, can, when administered to a mammal or human, be converted into compounds of Formula (I) having the desired biological activity.

Compounds in the disclosure and their pharmaceutically acceptable salts, prodrugs, as well as metabolites of the compounds, may also be used to treat certain eating disorders, obesity, compulsive gambling, sexual disorders, narcolepsy, sleep disorders, diabetes, metabolic syndrome, neurodegenerative disorders and CNS disorders/conditions as well as in smoking cessation treatment.

In one embodiment the treatment of CNS disorders and conditions by the compounds of the disclosure can include Huntington's disease, schizophrenia and schizo-affective conditions, delusional disorders, drug-induced psychoses, panic and obsessive compulsive disorders, post-traumatic stress disorders, age-related cognitive decline, attention deficit/hyperactivity disorder, bipolar disorders, personality disorders of the paranoid type, personality disorders of the schizoid type, psychosis induced by alcohol, amphetamines, phencyclidine, opioids hallucinogens or other drug-induced psychosis, dyskinesia or choreiform conditions including dyskinesia induced by dopamine agonists, dopaminergic therapies, psychosis associated with Parkinson's disease, psychotic symptoms associated with other neurodegenerative disorders including Alzheimer's disease, dystonic conditions such as idiopathic dystonia, drug-induced dystonia, torsion dystonia, and tardive dyskinesia, mood disorders including major depressive episodes, post-stroke depression, minor depressive disorder, premenstrual dysphoric disorder, dementia including but not limited to multi-infarct dementia, AIDS-related dementia, and neurodegenerative dementia.

In another embodiment, compounds of the disclosure may be used for the treatment of eating disorders, obesity, compulsive gambling, sexual disorders, narcolepsy, sleep disorders as well as in smoking cessation treatment.

In a further embodiment, compounds of the disclosure may be used for the treatment of obesity, schizophrenia, schizoaffective conditions, Huntington's disease, dystonic conditions and tardive dyskinesia.

In another embodiment, compounds of the disclosure may be used for the treatment of schizophrenia, schizo-affective conditions, Huntington's disease and obesity.

In a further embodiment, compounds of the disclosure may be used for the treatment of schizophrenia and schizo-affective conditions.

In an additional embodiment, compounds of the disclosure may be used for the treatment of Huntington's disease.

In another embodiment, compounds of the disclosure may be used for the treatment of obesity and metabolic syndrome.

Compounds of the disclosure may also be used in mammals and humans in conjunction with conventional antipsychotic medications including but not limited to Clozapine, Olanzapine, Risperidone, Ziprasidone, Haloperidol, Aripiprazole, Sertindole and Quetiapine. The combination of a compound of Formula (I) with a subtherapeutic dose of an aforementioned conventional antipsychotic medication may afford certain treatment advantages including improved side effect profiles and lower dosing requirements.

DEFINITIONS

Alkyl is meant to denote a linear or branched saturated or unsaturated aliphatic $C_1$-$C_8$ hydrocarbon which can be optionally substituted with up to 3 fluorine atoms and, if specified, substituted with other groups. Unsaturation in the form of a double or triple carbon-carbon bond may be internal or terminally located and in the case of a double bond both cis and trans isomers are included. Examples of alkyl groups include but are not limited to methyl, trifluoromethyl, ethyl, trifluoroethyl, isobutyl, neopentyl, cis- and trans-2-butenyl, isobutenyl, propargyl. $C_1$-$C_4$ alkyl is the subset of alkyl limited to a total of up to 4 carbon atoms.

In each case in which a size range for the number of atoms in a ring or chain is disclosed, all subsets are disclosed. Thus, $C_x$-$C_y$ includes all subsets, e.g., $C_1$-$C_4$ includes $C_1$-$C_2$, $C_2$-$C_4$, $C_1$-$C_3$ etc.

Acyl is an alkyl-C(O)— group wherein alkyl is as defined above. Examples of acyl groups include acetyl and proprionyl.

Alkoxy is an alkyl-O— group wherein alkyl is as defined above. $C_1$-$C_4$ alkoxy is the subset of alkyl-O— where the subset of alkyl is limited to a total of up to 4 carbon atoms. Examples of alkoxy groups include methoxy, trifluoromethoxy, ethoxy, trifluoroethoxy, and propoxy.

Alkoxyalkyl is an alkyl-O—($C_1$-$C_4$ alkyl)- group wherein alkyl is as defined above. Examples of alkoxyalkyl groups include methoxymethyl and ethoxymethyl.

Alkoxyalkyloxy is an alkoxy-alkyl-O— group wherein alkoxy and alkyl are as defined above. Examples of alkoxyalkyloxy groups include methoxymethyloxy ($CH_3OCH_2O$—) and methoxyethyloxy ($CH_3OCH_2CH_2O$—) groups.

Alkylthio is alkyl-S— group wherein alkyl is as defined above. Alkylthio includes $C_1$-$C_4$ alkylathio.

Alkylsulfonyl is alkyl-$SO_2$— wherein alkyl is as defined above. Alkylsulfonyl includes $C_1$-$C_4$ alkylsulfonyl.

Alkylamino is alkyl-NH— wherein alkyl is as defined above. Alkylamino includes $C_1$-$C_4$ alkylamino.

Dialkylamino is (alkyl)$_2$-N— wherein alkyl is as defined above.

Amido is $H_2NC(O)$—

Alkylamido is alkyl-NHC(O)— wherein alkyl is as defined above.

Dialkylamido is (alkyl)$_2$-NC(O)— wherein alkyl is as defined above.

Aromatic is heteroaryl or aryl wherein heteroaryl and aryl are as defined below.

Aryl is a phenyl or napthyl group. Aryl groups may be optionally and independently substituted with up to three groups selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —$OC(O)R_a$, —$OC(O)OR_a$, —$OC(O)NHR_a$, —$OC(O)N(R_a)$, —$SR_a$, —$S(O)R_a$, —$NH_2$, —$NHR_a$, —$N(R_a)R_b$), —$NHC(O)R_a$, —$N(R_a)C(O)R_b$, —$NHC(O)OR_a$, —$N(R_a)C(O)OR_b$, —$N(R_a)C(O)NH(R_b)$, —$N(R_a)C(O)NH(R_b)_2$, —$C(O)NH_2$, —$C(O)NHR_a$, —$C(O)N(R_a)(R_b)$, —$CO_2H$, —$CO_2R_a$, —$COR_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^iPr$, $^tBu$, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Arylalkyl is an aryl-alkyl- group wherein aryl and alkyl are as defined above.

Aryloxy is an aryl-O— group wherein aryl is as defined above.

Arylalkoxy is an aryl-($C_1$-$C_4$ alkyl)-O— group wherein aryl is as defined above.

Carboxy is a $CO_2H$ or $CO_2R_c$ group wherein $R_c$ is independently chosen from, alkyl, $C_1$-$C_4$ alkyl, cycloalkyl, arylalkyl, cycloalkylalkyl, $CF_3$, and alkoxyalkyl, wherein alkyl is as defined above.

Cycloalkyl is a $C_3$-$C_7$ cyclic non-aromatic hydrocarbon which may contain a single double bond and is optionally and independently substituted with up to three groups selected from alkyl, alkoxy, hydroxyl and oxo. Examples of cycloalkyl groups include cyclopropyl, cyclobutyl, cyclopentyl, cyclohexyl, cyclopentenyl and cyclohexanonyl.

Cycloalkyloxy is a cycloalkyl-O— group wherein cycloalkyl is as defined above. Examples include cyclopropyloxy, cyclobutyloxy and cyclopentyloxy. $C_3$-$C_6$ cycloalkyloxy is the subset of cycloalkyl-O— where cycloalkyl contains 3-6 carbon atoms.

Cycloalkylalkyl is a cycloalkyl-($C_1$-$C_4$ alkyl)- group. Examples include cyclopropylmethyl, cyclopropylethyl, cyclohexylmethyl and cyclohexylethyl.

Cycloalkylalkoxy is a cycloalkyl-($C_1$-$C_4$ alkyl)-O— group wherein cycloalkyl and alkyl are as defined above. Examples of cycloalkylalkoxy groups include cyclopropylmethoxy, cyclopentylmethoxy and cyclohexylmethoxy.

Halogen is F, Cl, Br or I.

Heteroaryl is a tetrazole, 1,2,3,4-oxatriazole, 1,2,3,5-oxatriazole, a mono or bicyclic aromatic ring system, or a heterobicyclic ring system with one aromatic ring having 5 to 10 ring atoms independently selected from C, N, O and S, provided that not more than 3 ring atoms in any single ring are other than C. Examples of heteroaryl groups include but are not limited to thiophenyl, furanyl, thiazolyl, isothiazolyl, oxazolyl, isoxazolyl, 1,2,4-oxadiazolyl, 1,3,4-oxadiazolyl, pyrrazolyl, imidazolyl, 1,2,3-triazolyl, 1,3,4-triazolyl, pyrimidinyl, pyrazinyl, indolyl, quinolyl, tetrahydroquinolyl, isoquinolyl, tetrahydroisoquinolyl, indazolyl, benzthiadiazololyl, benzoxadiazolyl and benzimidazolyl. Heteroaryl groups may be optionally and independently substituted with up to 3 substituents independently selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —$OC(O)R_a$, —$OC(O)OR_a$, —$OC(O)NHR_a$, —$OC(O)N(R_a)$, —$SR_a$, —$S(O)R_a$, —$NH_2$, —$NHR_a$, —$N(R_a)(R_b)$, —$NHC(O)R_a$, —$N(R_a)C(O)R_b$, —$NHC(O)OR_a$, —$N(R_a)C(O)OR_b$, —$N(R_a)C(O)NH(R_b)$, —$N(R_a)C(O)NH(R_b)_2$, —$C(O)NH_2$, —$C(O)NHR_a$, —$C(O)N(R_a)(R_b)$, —$CO_2H$, —$CO_2R_a$, —$COR_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^iPr$, $^tBu$, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Heteroarylalkyl is a heteroaryl-($C_1$-$C_4$ alkyl)- group wherein heteroaryl and alkyl are as defined above. Examples of heteroarylalkyl groups include 4-pyridinylmethyl and 4-pyridinylethyl.

Heteroaryloxy is a heteroaryl-O group wherein heteroaryl is as defined above.

Heteroarylalkoxy is a heteroaryl-($C_1$-$C_4$ alkyl)-O— group wherein heteroaryl and alkoxy are as defined above. Examples of heteroarylalkyl groups include 4-pyridinylmethoxy and 4-pyridinylethoxy.

Heterobicyclic ring system is a ring system having 8-10 atoms independently selected from C, N, O and S, provided that not more than 3 ring atoms in any single ring are other than carbon and provided that at least one of the rings is aromatic; said bicyclic ring may be optionally and independently substituted with up to 3 substituents independently selected from alkyl, alkoxy, cycloalkyl, $C_3$-$C_6$ cycloalkyloxy, cycloalkylalkyl, halogen, nitro, alkylsulfonyl and cyano. Examples of 8-10 membered heterobicyclic ring systems include but are not limited to 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl, tetrahydroquinoxalinyl, benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b]pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d]pyrimidyl, pyrido[4,3-b]pyrazyl, pyrido[4,3-c]pyridazyl, pyrido[4,3-c]pyrimidyl, quinazolyl, 1H-benzo[d][1,2,3]triazoyl, 1H-benzo[d]imidazoyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl, [1,2,4]triazolo[4,3-a]pyridinyl, benzo[b]thienyl, benzo[c][1,2,5]oxadiazyl, benzo[c][1,2,5]thiadiazyl, benzo[d]isothiazoyl, benzo[d] isoxazoyl, benzo[d]oxazoyl, benzo[d]thiazoyl, benzofuryl, imidazo[1,2-a]pyrazyl, imidazo[1,2-c]pyridinyl, imidazo[1,2-a]pyrimidyl, imidazo[1,2-b]pyridazyl, imidazo[1,2-c]pyrimidyl, imidazo[1,5-c]pyrazyl, imidazo[1,5-a]pyridinyl, imidazo[1,5-a]pyrimidyl, imidazo[1,5-b]pyridazyl, imidazo[1,5-c]pyrimidyl, indolizyl, pyrazolo[1,5-c]pyrazyl, pyrazolo[1,5-a]pyridinyl, pyrazolo[1,5-a]pyrimidyl, pyrazolo[1,5-b]pyridazine, pyrazolo[1,5-c]pyrimidine, pyrrolo[1,2-a]pyrazine, pyrrolo[1,2-c]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, 2H-indazoyl, 3H-imidazo[4,5-b]pyridinyl, 3H-imidazo[4,5-c]pyridinyl, benzo[c]isothiazyl, benzo[c]isoxazyl, furo[2,3-b]pyridinyl, furo[2,3-c]pyridinyl, furo[3,2-b]pyridinyl, furo[3,2-c]pyridinyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo[5,4-b]pyridinyl, isoxazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, thiazolo[4,5-b]pyridiyl, thiazolo[4,5-c]pyridinyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl and thieno[3,2-c]pyridinyl.

Heterocycloalkyl is a non-aromatic, monocyclic or bicyclic saturated or partially unsaturated ring system comprising 5-10 ring atoms selected from C, N, O and S, provided that not more than 2 ring atoms in any single ring are other than C. In the case where the heterocycloalkyl group contains a nitrogen atom the nitrogen may be substituted with an alkyl, acyl, —C(O)O-alkyl, —C(O)NH(alkyl) or a —$C(O)N(alkyl)_2$ group. Heterocycloalkyl groups may be optionally and independently substituted with hydroxy, alkyl and alkoxy groups and may contain up to two oxo groups. Heterocycloalkyl groups may be linked to the rest of the molecule via either carbon or nitrogen ring atoms. Examples of heterocycloalkyl groups include tetrahydrofuranyl, tetrahydrothienyl, tetrahydro-2H-pyran, tetrahydro-2H-thiopyranyl, pyrrolidinyl, pyrrolidonyl, succinimidyl, piperidinyl, piperazinyl, N-methylpiperazinyl, morpholinyl, morpholin-3-one, thiomorpholinyl, thiomorpholin-3-one, 2,5-diazabicyclo[2.2.2]octanyl, 2,5-diazabicyclo[2.2.1]heptanyl, octahydro-1H-pyrido[1,2-a]pyrazine, 3-thia-6-azabicyclo[3.1.1]heptane and 3-oxa-6-azabicyclo[3.1.1]heptanyl.

Heterocycloalkylalkyl is a heterocycloalkyl-($C_1$-$C_4$ alkyl)- group wherein heterocycloalkyl is as defined above.

Heterocycloalkyloxy is a heterocycloalkyl-O— group wherein heterocycloalkyl is as defined above.

Heterocycloalkylalkoxy is a heterocycloalkyl-($C_1$-$C_4$ alkyl)-O— group wherein heterocycloalkyl is as defined above.

Oxo is a —C(O)— group.

Phenyl is a benzene ring which may be optionally and independently substituted with up to three groups selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —OC(O)$R_a$, —OC(O)O$R_a$, —OC(O)NH$R_a$, —OC(O)N($R_a$), —S$R_a$, —S(O)$R_a$, —$NH_2$, —NH$R_a$, —N($R_a$)($R_b$), —NHC(O)$R_a$, —N($R_a$)C(O)$R_b$, —NHC(O)O$R_a$, —N($R_a$)C(O)O$R_b$, —N($R_a$)C(O)NH($R_b$), —N($R_a$)C(O)NH($R_b$)$_2$, —C(O)$NH_2$, —C(O)NH$R_a$, —C(O)N($R_a$)($R_b$), —$CO_2$H, —$CO_2R_a$, —COR$_a$ wherein $R_a$ and $R_b$ are independently chosen from alkyl, alkoxyalkyl, —$CH_2CH_2$OH, —$CH_2CH_2$OMe, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Restricted phenyl is a benzene ring which may be optionally and independently substituted with up to three groups selected from halogen, $CF_3$, CN, alkoxy, alkoxyalkyl, aryloxy, alkoxyalkyloxy, heterocycloalkyl, heterocycloalkyloxy, heteroaryl, heteroaryloxy, —$OCH_2CH_2OCH_3$, —OC(O)$R_a$, —OC(O)O$R_a$, —OC(O)N($R_a$), —N($R_a$)($R_b$), —NHC(O)$R_a$, —N($R_a$)C(O)$R_b$, —NHC(O)O$R_a$, —N($R_a$)C(O)O$R_b$, —C(O)N($R_a$)($R_b$), —COR$_a$ wherein $R_a$ and $R_b$ are independently chosen from alkyl, alkoxyalkyl, —$CH_2CH_2$OH, —$CH_2CH_2$OMe, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Abbreviations used in the following examples and preparations include:

Ac Acyl (Me-C(O)—)
AcN Acetonitrile
BINAP 2,2'-bis(diphenylphosphino)-1,1'-binaphthyl
Bn Benzyl
Celite® Diatomaceous earth
DBU 1,8-Diazabicyclo[5.4.0]undec-7-ene
DCC N,N', Dicyclohexylcarbodiimide
DCM Dichloromethane
DIEA Di-isopropylethyl amine
DIPEA Di-isopropylethyl amine
DMAP 4-Dimethylaminopyridine
DMF Dimethylformamide
DMP Dess Martin Periodinane
DMSO Dimethyl sulfoxide
Dppf 1,4-Bis(diphenylphosphino) ferrocene
EDC 1-(3-Dimethylaminopropyl)-3-ethylcarbodiimide Hydrochloride
$Et_3N$ Triethylamine
g gram(s)
h Hour(s)
hr Hour(s)
HATU 2-(7-Aza-1H-benzotriazole-1-yl)-1,1,3,3-tetramethyluronium hexafluorophosphate
HMDS Hexamethyldisilazide
HOBt 1-Hydroxybenzotriazole
HPLC High Pressure Liquid Chromatography
HRMS High resolution mass spectrometry
i.v. Intravenous
KHMDS Potassium Hexamethydisilazide
LDA Lithium Di-isopropylamide
m Multiplet
m- meta
MEM Methoxyethoxymethyl
MeOH Methyl Alcohol or Methanol
min Minute(s)
mmol millimoles
mmole millimoles
Ms Mesylate
MS Mass Spectrometry
MW Molecular Weight
NBS N-Bromosuccinamide
NIS N-Iodosuccinamide
NMR Nuclear Magnetic Resonance
NMM N-Methyl Morpholine
NMP N-Methyl-2-pyrrolidone
o ortho
o/n overnight
p para
PCC Pyridinium Chlorochromate
PEPPSI 1,3-Bis(2,6-diisopropylphenyl)imidazolidene)(3-chloropyridinyl) palladium(II) dichloride
$PhNTf_2$ 1,1,1-trifluoro-N-phenyl-N-(trifluoromethylsulfonyl)methanesulfonamide
POPd Dihydrogen dichlorobis(di-tert-butylphosphinito-kp) palladate (2-)
p.s.i. Pounds per square inch
PPA Polyphosphoric acid
PPAA 1-Propanephosphonic Acid Cyclic Anhydride
PTSA p-Toluenesulfonic acid
PyBOP® Benzotriazol-1-yl-oxytripyrrolidinophosphonium hexafluorophosphate
RT (or rt) room temperature (about 20-25° C.)
s Singlet
sat. Saturated
t Triplet
TBAF Tetra-butyl ammonium fluoride
TEA Triethylamine
TFA Trifluoroacetic Acid
THF Tetrahydrofuran
TLC Thin layer chromatography
TMS Trimethylsilyl
Tf Triflate
Tof-MS Time of Flight Mass Spectrometry
Ts Tosylate
v/v volume/volume
wt/v weight/volume

DETAILED DESCRIPTION

The 1,2 disubstituted heterocyclic compounds of Formula I may be prepared from multi-step organic synthesis routes from commercially available starting materials by one skilled in the art of organic synthesis using established organic synthetic procedures. Non-commercially available phenyl acetic acids can be made from commercially available starting materials via methods known by one skilled in the art of organic synthesis. Such methods include synthesis from the corresponding aryl acids via. the Wolff rearrangement using diazomethane.

Compounds of the disclosure where HET is A29 and A31 may be prepared generally as depicted in Schemes 1-8 below.

Compounds of the disclosure of Formula (I) wherein HET is A29 and X=phenyl or heteroaryl (each respectively optionally substituted) thus having general Formula LIV may be prepared generally as depicted in Scheme 1:

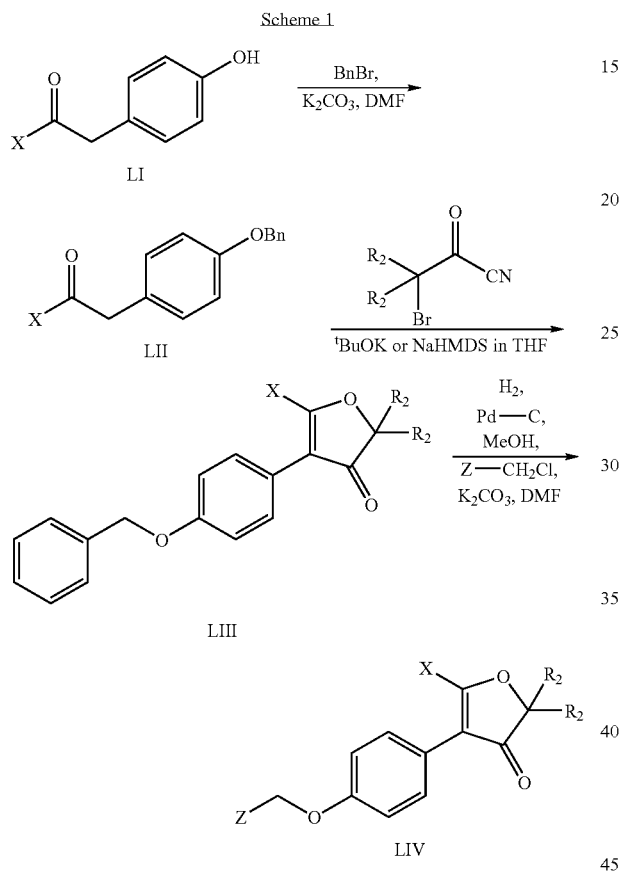

Alternatively, compounds of the disclosure of Formula (I) wherein HET is A29 and X=phenyl or heteroaryl (each respectively optionally substituted) and thus having general Formula LIV may also be prepared generally as depicted in Scheme 2:

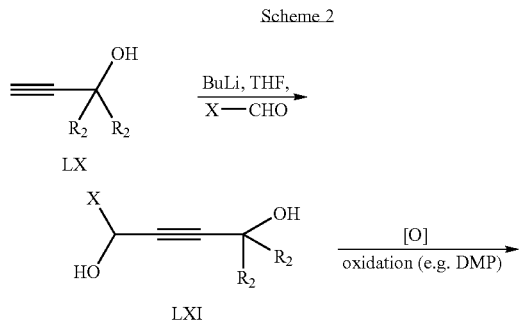

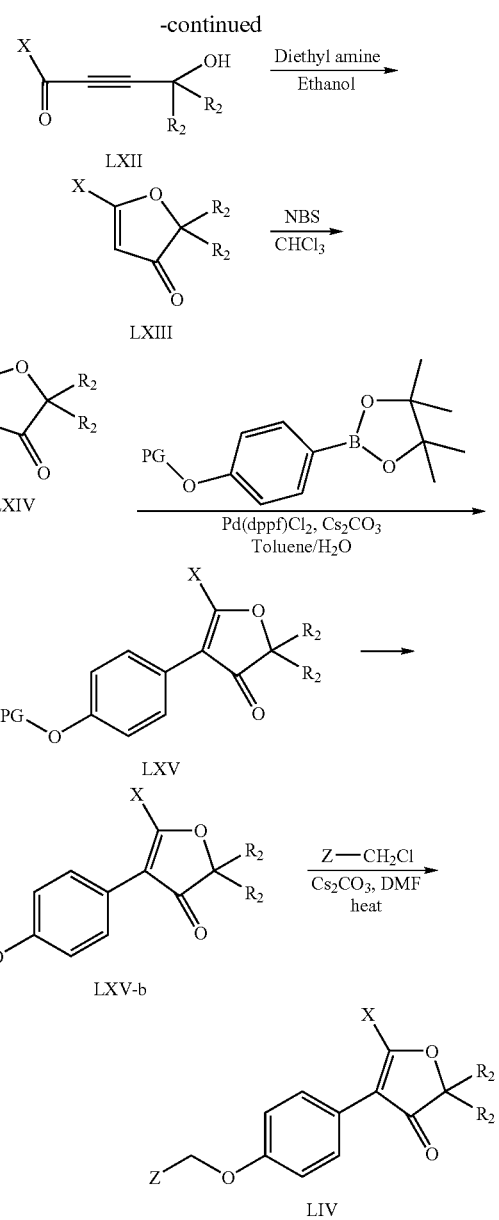

Intermediate compounds of Formula LXIII may alternatively be synthesized as depicted in Scheme 3.

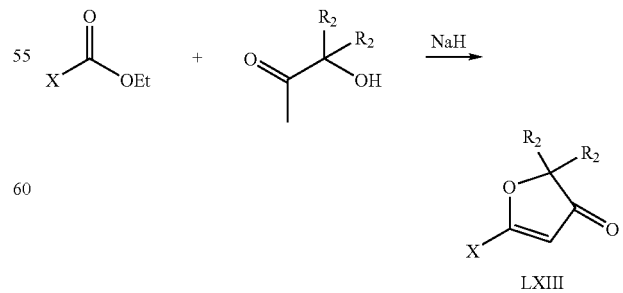

Compounds of the disclosure of Formula (I) wherein HET is A31 and X=phenyl or heteroaryl (each optionally substituted) are as described previously and thus having general Formula LXXIV may be prepared generally as depicted in Scheme 4:

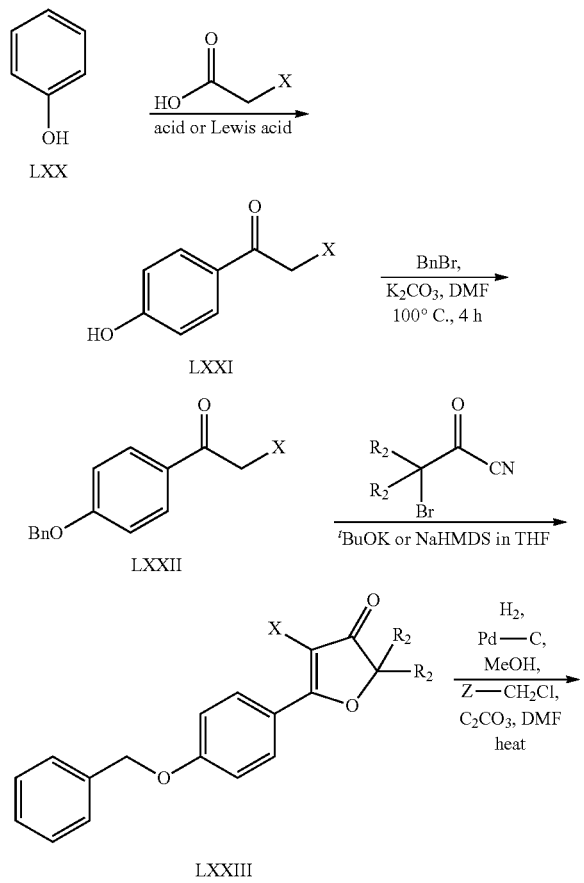

The general synthesis of heterocyclic chloride intermediates (Z—CH$_2$—Cl) where Z corresponds to an imidazo[1,2-a]pyrid-2-yl is depicted in Scheme 5.

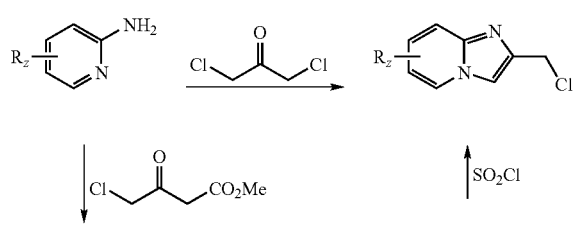

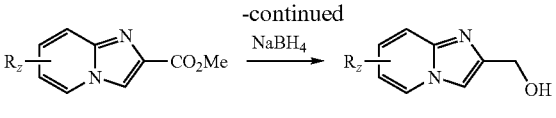

The general synthesis of heterocyclic chloride intermediates (Z—CH$_2$—Cl) where Z corresponds to an imidazo[1,2-b]pyridazin-6-yl is depicted in Scheme 6.

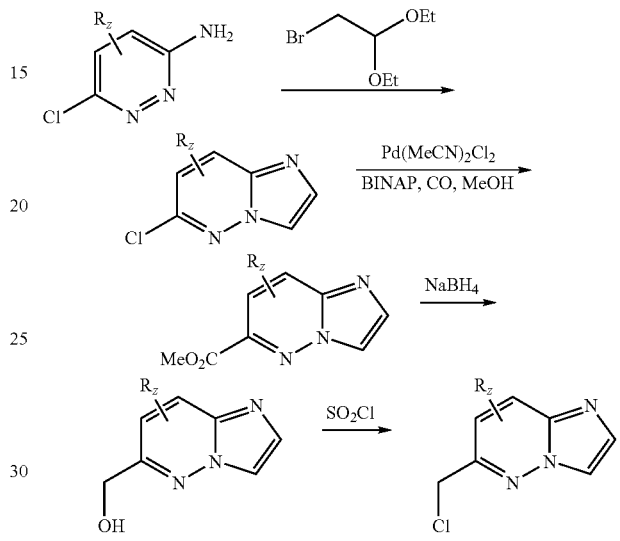

The general synthesis of heterocyclic chloride intermediates (Z—CH$_2$—Cl) where Z corresponds to an imidazo[1,2-b]pyridazin-2-yl is depicted in Scheme 7.

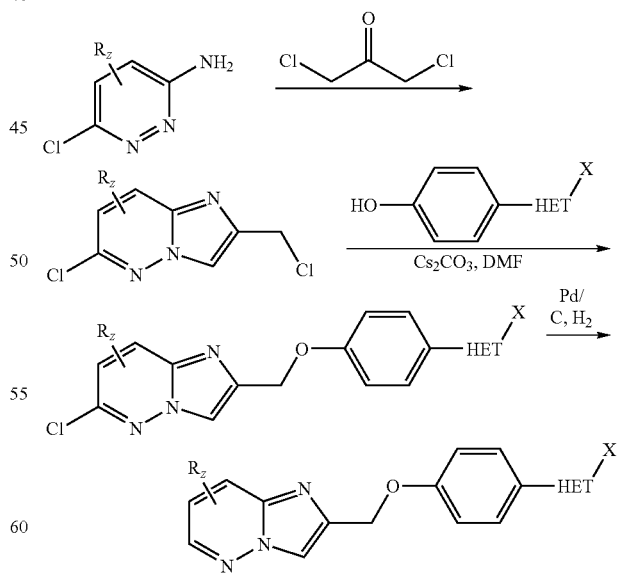

The general synthesis of heterocyclic chloride intermediates (Z—CH$_2$—Cl) where Z corresponds to either a 5-substituted-pyridin-2-yl or a 3,5-disubstituted-1pyridin-2-yl is depicted in Scheme 8.

Scheme 8

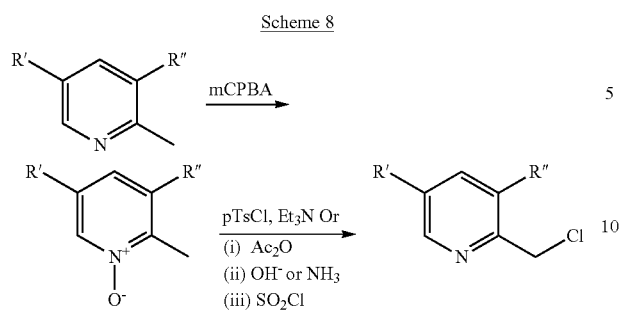

Reactive groups not involved in the above processes can be protected with standard protecting groups during the reactions and removed by standard procedures (T. W. Greene & P. G. M. Wuts, Protecting Groups in Organic Synthesis, Third Edition, Wiley-Interscience) known to those of ordinary skill in the art. Presently preferred protecting groups include methyl, benzyl, MEM, acetate and tetrahydropyranyl for the hydroxyl moiety, and BOC, Cbz, trifluoroacetamide and benzyl for the amino moiety, methyl, ethyl, tert-butyl and benzyl esters for the carboxylic acid moiety. Practitoners in the art will also recognize that the order of certain chemical reactions can be changed. Practitioners of the art will also note that alternative reagents and conditions exist for various chemical steps.

Experimental Procedures

The synthesis of N-methoxy-N-methylcarboxamides from their corresponding carboxylic acids is known by those of ordinary skill in the art. A representative procedure is described below, where is selected from

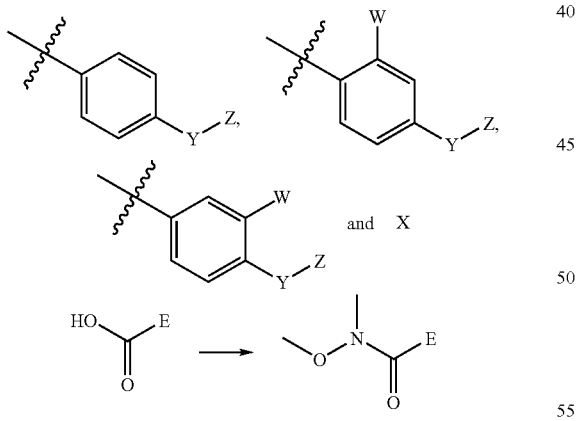

To a stirred solution of carboxylic acid (1 eq., 3 mmol) in DCM (50 mL) was added HATU (1.5 eq, 4.5 mmol), N-methoxy methylamine (1.5 eq, 4.5 mmol) and TEA (3 eq., 9 mmol) at RT under nitrogen atmosphere. The reaction mixture was then stirred at RT for 3 h. The reaction mixture was diluted with water and the aqueous layer was extracted with DCM (3×50 mL). The combined organic extracts were washed with water (50 mL), brine (20 mL), dried over anhydrous $Na_2SO_4$, filtered and evaporated under reduced pressure to afford the corresponding N-methoxy-N-methylcarboxamide.

HPLC Conditions

Condition-A:
  Column: Acquity BEH C-18 (50×2.1 mm, 1.7μ)
  Column Temp: 25° C.
  Mobile Phase A/B: Acetonitrile (0.025% TFA) and water
  Flow Rate: 0.50 mL/Min 4-(5,5-dimethyl-4-oxo-4,5-dihydrofuran-2-yl)benzonitrile

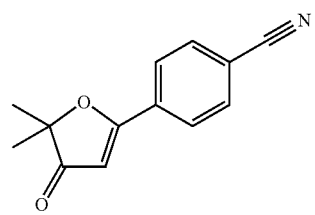 [SMILES: CC1(C)OC(c2ccc(C#N)cc2)=CC1=O]

To a suspension of NaH (0.9 g) in THF at RT was added 3-hydroxy-3-methyl-2-butanone (1 g) and ethyl methyl 4-cyanobenzoate (1.58 g). The resultant mixture was refluxed overnight, upon which the reaction was quenched with 12N HCl (6 mL) MgSO4 (excess) was added until the organic phase became clear. The solids were removed by filtration and the filtrate was concentrated under reduced pressure. The residue was purified by column chromatography to give 4-(5,5-dimethyl-4-oxo-4,5-dihydrofuran-2-yl)benzonitrile (0.63 g).

Synthesis of 4-(4-Hydroxyphenyl)-5-(4-methoxyphenyl)-2,2-dimethylfuran-3(2H)-one 4-Methoxy-N-methoxy-N-methylbenzamide

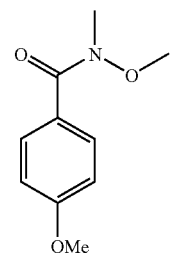

To a stirred solution of 4-methoxybenzoic acid (10.0 g, 65.70 mmol) in DCM (50 mL) were added EDCI (18.90 g, 98.60 mmol), HOBT (10.0 g, 65.70 mmol), N-methoxy methylamine (13.0 g, 131.40 mmol) and DIPEA (34.3 mL, 197.20 mmol) at RT under a nitrogen atmosphere. The reaction mixture was stirred at RT for 12 h. The reaction mixture was diluted with water and the aqueous layer was extracted with DCM (3×100 mL). The combined organic extracts were washed with water (2×100 mL), brine (2×50 mL), dried over anhydrous $Na_2SO_4$, filtered and evaporated under reduced pressure to afford crude product. The crude material was purified by flash column chromatography using 20% ethyl acetate in hexane and silica gel (230-400 Mesh) to afford N,4-dimethoxy-N-methylbenzamide (11.0 g, 86%) as a colorless liquid.

4-Hydroxy-1-(4-methoxyphenyl)-4-methylpent-2-yn-1-one

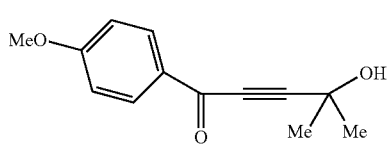 [SMILES: COc1ccc(C(=O)C#CC(C)(C)O)cc1]

To a stirred solution of 2-methylbut-3-yn-2-ol (2.15 g, 25.6 mmol) in dry THF (80 mL) was added n-BuLi (24.0 mL, 38.7 mmol, 1.6 M in hexane) drop wise at −20° C. under an inert atmosphere for a period of 10 min. After being stirred for 30 min at −20° C., a solution of N,4-dimethoxy-N-methylbenzamide (2.5 g, 12.8 mmol) in dry THF (10 mL) was added to reaction mixture and stirring was continued for an additional 3 h at −20° C. The reaction mixture was quenched with a saturated NH$_4$Cl solution and extracted with EtOAc (2×100 mL). The combined organic layer was washed with water (100 mL), brine (40 mL), dried over Na$_2$SO$_4$, filtered and concentrated in vacuo to afford 4-hydroxy-1-(4-methoxyphenyl)-4-methylpent-2-yn-1-one (2.25 g, 81%) as a colorless liquid.

5-(4-Methoxyphenyl)-2,2-dimethylfuran-3(2H)-one

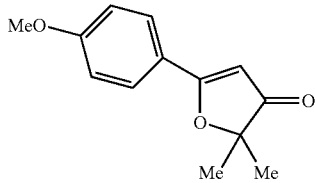

To 4-hydroxy-1-(4-methoxyphenyl)-4-methylpent-2-yn-1-one (10 g, 45.8 mmol) was added methanolic ammonia (50 mL) at room temperature and the reaction mixture was stirred overnight. The mixture was concentrated under reduced pressure and 50% aqueous acetic acid was added. The resultant mixture was heated at reflux for 4 hours. The pH was adjusted to 8 with saturated ammonium chloride solution and extracted with DCM. The combined organics were washed with water and brine solution, dried over sodium sulphate, filtered, concentrated under reduced pressure and washed with heptane to afford 5-(4-methoxyphenyl)-2,2-dimethylfuran-3(2H)-one (8.6 g, 86%) as white solid. $^1$H NMR (500 MHz, d$_6$-DMSO): δ 7.99 (d, 2H), 7.15 (d, 2H), 6.20 (s, 1H), 3.89 (s, 3H), 1.42 (s, 6H). MS: [M+H]+: m/z=218.1.

4-Bromo-5-(4-methoxyphenyl)-2,2-dimethylfuran-3(2H)-one

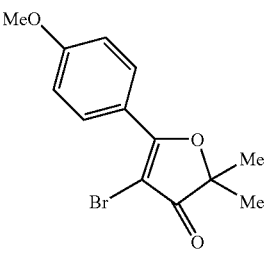 [SMILES: COc1ccc(C2=C(Br)C(=O)C(C)(C)O2)cc1]

To a stirred solution of 5-(4-methoxyphenyl)-2,2-dimethylfuran-3(2H)-one (5.5 g, 0.025 mol) in CHCl$_3$ (100 mL) was added NBS (6.733 g, 0.038 mol) portion wise at RT. The reaction mixture was stirred for 2 h at RT. The reaction mixture was diluted with DCM (100 mL), washed with water (50 mL), brine (50 mL), dried over Na$_2$SO$_4$, filtered and then concentrated in vacuo to obtain the crude product. The crude material was purified via by flash column chromatography using 25% ethyl acetate in hexane and silica gel (230-400 Mesh) to afford 4-bromo-5-(4-methoxyphenyl)-2,2-dimethylfuran-3(2H)-one (4.6 g, 65%) as a solid.

4-(4-(Benzyloxy)phenyl)-5-(4-methoxyphenyl)-2,2-dimethylfuran-3(2H)-one

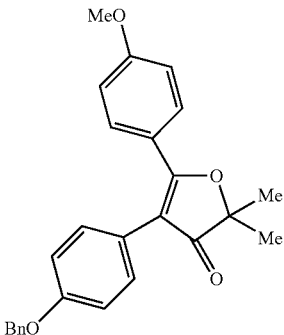 [SMILES: COc1ccc(C2=C(c3ccc(OCc4ccccc4)cc3)C(=O)C(C)(C)O2)cc1]

4-Bromo-5-(4-methoxyphenyl)-2,2-dimethylfuran-3(2H)-one (2 g, 6.7 mol), 2-(4-(benzyloxy)phenyl)-4,4,5,5-tetramethyl-1,3,2-dioxaborolane (2.43 g, 0.0067 mol), and Cs$_2$CO$_3$ (11 g, 0.034 mol) in toluene (25 mL) and water (8 mL) was degassed, Pd (dppf) Cl$_2$ (1.1 g, 0.0013 mol) was added under an inert atmosphere and the mixture degassed once again. The reaction was heated at reflux for 3 h, upon which the reaction mixture was filtered through a pad of Celite® and the filtrate was diluted with EtOAc (100 mL), washed with water (50 mL), brine (50 mL), dried over Na$_2$SO$_4$, filtered and concentrated in vacuo to obtain the crude product. The crude material was purified by flash column chromatography using 30% ethyl acetate in hexane and silica gel (230-400 Mesh), Rf=0.30 to afford 4-(4-(benzyloxy)phenyl)-5-(4-methoxyphenyl)-2,2-dimethylfuran-3(2H)-one (2.3 g, 73%) as solid. $^1$H NMR (500 MHz, d$_6$-DMSO): δ 8.42 (d, J=7.6 Hz, 1H), 8.06-7.99 (m, 2H), 7.95

(t, J=7.2 Hz, 1H), 7.72 (t, J=7.2 Hz, 1H), 7.63 (t, J=7.8 Hz, 1H), 7.56 (d, J=7.2 Hz, 2H); 7.18 (d, J=7.4 Hz, 2H), 7.12 (d, J=7.2 Hz, 2H), 6.89 (d, J=7.2 Hz, 2H), 5.38 (s, 2H), 3.79 (s, 3H), 1.42 (s, 6H). MS: [M+H]+: m/z=452.1; [M+Na]+: m/z=474.2.

4-(4-Hydroxyphenyl)-5-(4-methoxyphenyl)-2,2-dimethylfuran-3(2H)-one

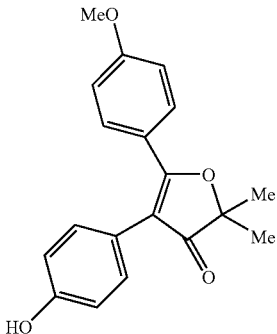 [SMILES: COc1ccc(C2=C(c3ccc(O)cc3)C(=O)C(C)(C)O2)cc1]

5% Palladium on carbon (7.0 g) was added to a solution 4-(4-(benzyloxy)phenyl)-5-(4-methoxyphenyl)-2,2-dimethylfuran-3(2H)-one (19 g, 42.1 mmol) in methanol (25 ml) at RT under an atmosphere of nitrogen. The nitrogen atmosphere was changed to an atmosphere of hydrogen. The reaction mixture was stirred under an atmosphere of hydrogen at RT for 4 h (the reaction was monitored by TLC). The reaction mixtures was filtered over through a pad of Celite®, washed with methanol, concentrated in vacuo and the resultant residue was slurried with heptane. The solid was filtered & dried under vacuum to afford 4-(4-hydroxyphenyl)-5-(4-methoxyphenyl)-2,2-dimethylfuran-3(2H)-one (14.0 g, 95%) as light yellow solid. $^1$H NMR, 500 MHz, DMSO-$d_6$: δ 9.5 (bs, 1H), 7.55 (d, 2H), 7.05 (d, 2H), 7.0 (d, 2H), 6.75 (d, 2H), 3.8 (s, 3H), 1.4 (s, 6H). MS: [M+H]: m/z=311.2. HPLC: (98.8%, Eclipse XDB-C18, 150×4.6 mm, 5 um. Mobile Phase: 0.1% TFA in Water. (A). ACN (B), Flow rate: 1.5 ml/min).

Synthesis of 5-(4-Hydroxyphenyl)-2,2-dimethyl-4-(pyridin-4-yl) furan-3(2H)-one

Trimethyl (2-methylbut-3-yn-2-yloxy) silane

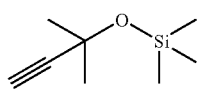

To a stirred solution of 2-methylbut-3-yn-2-ol (20 g, 0.23 mol) in HMDS (42.3 g, 0.261 mol) was added LiClO$_4$ (38.03 g, 0.35 mol) at RT. The reaction mixture was then stirred for additional 30 minutes, diluted with water (100 mL) and then extracted with ether (3×200 mL) The combined ether layers were washed with water (100 mL) and brine (100 mL), dried over Na$_2$SO and filtered. The ether was distilled off at 80° C. to afford trimethyl (2-methylbut-3-yn-2-yloxy) silane (25 g) as an oil.

4-Methyl-1-(pyridin-4-yl)-4-(trimethylsilyloxy) pent-2-yn-1-one

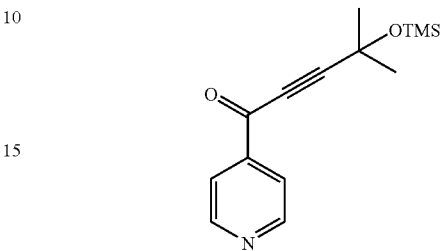

To a pre-cooled −78° C. stirred solution of trimethyl (2-methylbut-3-yn-2-yloxy) silane (5.0 g, 0.03 mol) in dry THF (150 mL), n-BuLi (23.82 mL, 0.03 mol, 1.6 M in hexane) was added dropwise over a period of 10 minutes under an inert atmosphere. The reactions was stirred for 30 minutes at −78° C. and then a solution of N-methoxy-N-methylisonicotinamide (6.34 g, 0.03 mol) in dry THF (30 mL) was added to the reaction mixture and stirring was continued for an additional 40 min at −78° C. The reaction mixture was quenched with a saturated NH$_4$Cl solution and extracted with EtOAc (2×100 mL). The combined organic layers were washed with water (100 mL) and brine (100 mL), dried over Na$_2$SO$_4$, filtered and finally concentrated in vacuo to obtain a residue. The residue was purified via silica gel column chromatography eluting with 5% EtOAc in hexanes to afford 4-methyl-1-(pyridin-4-yl)-4-(trimethylsilyloxy) pent-2-yn-1-one (2.2 g, 27%) as oil.

4-Hydroxy-4-methyl-1-(pyridin-4-yl) pent-2-yn-1-one

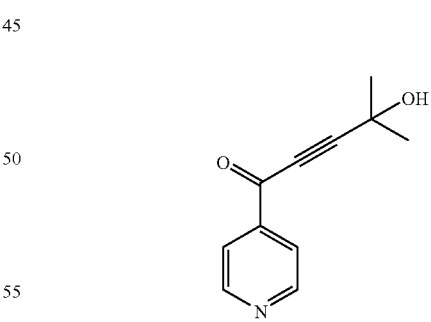

To a stirred solution of 4-methyl-1-(pyridin-4-yl)-4-(trimethylsilyloxy) pent-2-yn-1-one (0.5 g, 1.915 mmol) in DCM (10 mL) was added PTSA (0.47 g, 2.49 mmol) at RT and the reaction mixture was stirred for 2 h. The reaction mixture was diluted with DCM (50 mL). The organic layers were washed with a saturated NaHCO$_3$ solution and water, dried over Na₂SO₄, filtered and then concentrated in vacuo to afford 4-hydroxy-4-methyl-1-(pyridin-4-yl) pent-2-yn-1-one (0.35 g, 96%) as an oil.

2,2-Dimethyl-5-(pyridin-4-yl) furan-3(2H)-one

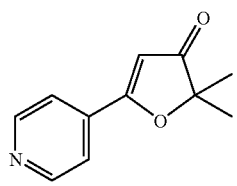

To a stirred solution of 4-hydroxy-4-methyl-1-(pyridin-4-yl) pent-2-yn-1-one (1.49 g, 0.007 mol) in ethanol (15 mL), diethylamine (0.511 g, 0.007 mol) in EtOH (15 mL) was added dropwise at RT. The mixture was then stirred for additional 40 min. The EtOH was evaporated and the mixture was diluted with EtOAc (100 mL). The organic layers were washed with water (50 mL) and brine (20 mL), dried over Na₂SO₄, filtered and concentrated in vacuo to afford 2,2-dimethyl-5-(pyridin-4-yl) furan-3(2H)-one (1.4 g).

4-Bromo-2,2-dimethyl-5-(pyridin-4-yl) furan-3(2H)-one

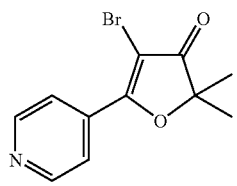

To a stirred solution of 2,2-dimethyl-5-(pyridin-4-yl) furan-3(2H)-one (0.81 g, 4.28 mmol) in CHCl₃ (20 mL), NBS (1.3 g, 7.28 mmol) was added portionwise at RT. The reaction mixture was then stirred for 2 h and diluted with DCM (100 mL). The organic layers were washed with water (50 mL) and brine (50 mL), dried over Na₂SO₄, filtered, and then concentrated in vacuo to obtain the crude product. The crude material was purified via silica gel column chromatography to afford 4-bromo-2,2-dimethyl-5-(pyridin-4-yl) furan-3(2H)-one (0.25 g, 21%) as a solid.

4-(4-(Benzyloxy)phenyl)-2,2-dimethyl-5-(pyridin-4-yl)furan-3(2H)-one

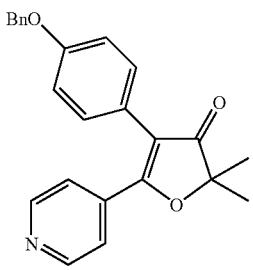 [SMILES: CC1(C)OC(c2ccncc2)=C(c2ccc(OCc3ccccc3)cc2)C1=O]

A solution of 4-bromo-2,2-dimethyl-5-(pyridin-4-yl)furan-3(2H)-one (10.0 g, 37.2 mmol), 2-(4-(benzyloxy)phenyl)-4,4,5,5-tetramethyl-1,3,2-dioxaborolane (13.8 g, 44.7 mmol), and Cs₂CO₃ (36.27 g, 111.6 mmol) in toluene (100 mL) and water (50 mL) was degassed. Dichloro[1,1'-bis(diphenylphosphino)ferrocene]palladium(II) (2.7 g, 3.7 mmol) was added under an inert atmosphere and again degassed. Then the reaction was refluxed for 3 h and monitored by TLC. Upon complete consumption of the starting material, the reaction mixture was filtered through a bed of Celite® washing with ethyl acetate. The organic layer was then washed with water, brine, dried over Na₂SO₄, filtered and concentrated under reduced pressure. The residue was purified by flash column chromatography using 20% ethyl acetate in n-hexanes on 230-400 mesh silica gel to afford 4-(4-(benzyloxy)phenyl)-2,2-dimethyl-5-(pyridin-4-yl)furan-3(2H)-one (8.3 g, 60.2%) as a light orange color solid. ¹H NMR, 500 MHz, DMSO-d₆: δ 8.2 (d, 2H), 7.85 (d, 2H), 7.6 (d, 4H), 7.4 (t, 1H), 7.15 (d, 2H), 7.05 (d, 2H), 5.1 (s, 2H), 1.45 (s, 6H). MS: [M+H]+: m/z=396.0. HPLC: (97.5%, Column: Eclipse XDB-C18, 150×4.6 mm, 5 um. Mobile Phase: 0.1% TFA in Water. (A). ACN (B), Flow rate: 1.5 ml/min).

5-(4-Hydroxyphenyl)-2,2-dimethyl-4-(pyridin-4-yl) furan-3(2H)-one

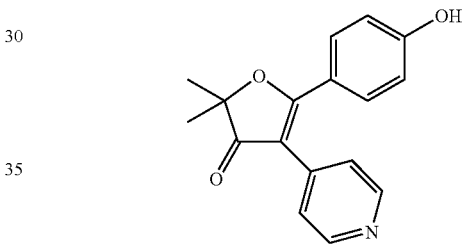

To a stirred solution of 5-(4-(benzyloxy)phenyl)-2,2-dimethyl-4-(pyridin-4-yl) furan-3(2H)-one (620 mg, 0.001 mmol) in MeOH (15 mL) was added Pd (OH)₂ (120 mg, 0.85 mmol) at RT under an inert atmosphere. The reaction mixture was stirred under a hydrogen atmosphere for 1 h. The reaction mixture was then filtered through a pad of Celite® and the filtrate was concentrated in vacuo to obtain the crude product. The crude material was purified via silica gel column chromatography to afford 544-hydroxyphenyl)-2,2-dimethyl-4-(pyridin-4-yl) furan-3(2H)-one (280 mg, 60%) as a solid.

Synthesis of 4-(3-(4-Hydroxyphenyl)-5,5-dimethyl-4-oxo-4,5-dihydrofuran-2-yl) benzonitrile 4-Cyano-N-methoxy-N-methylbenzamide

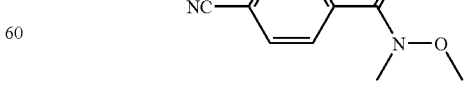

To a stirred solution of 4-cyanobenzoic acid (5.0 g, 34.0 mmol) in DCM (75 mL) were added HATU (19.40 g, 51.0 mmol), N-methoxy, N-methylamine (4.90 g, 51.0 mmol) and TEA (14.30 mL, 102.0 mmol) at RT under a nitrogen atmosphere. The reaction mixture was then stirred at RT for 3 h, diluted with water and the aqueous layer was extracted with DCM (3×100 mL). The combined organic extracts were washed with water (60 mL) and brine (30 mL), dried over anhydrous $Na_2SO_4$, filtered and evaporated under reduced pressure to afford 4-cyano-N-methoxy-N-methylbenzamide (6.2 g, 96%) as a yellow color oil.

4-(4-Methyl-4-(trimethylsilyloxy)pent-2-ynoyl)benzonitrile

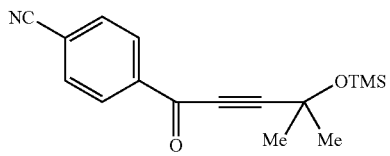

To a −78° C. stirred solution of trimethyl (2-methylbut-3-yn-2-yloxy) silane (3.3 g, 20.00 mmol) in dry THF (45 mL), n-BuLi (4.1 mL, 9.00 mmol, 1.6 M in hexane) was added dropwise over 10 minutes under an inert atmosphere. The reaction mixture was stirred for 30 min at −78° C., and then a solution of 4-cyano-N-methoxy-N-methylbenzamide (2.0 g, 10.00 mmol) in dry THF (15 mL) was added to the reaction mixture and stirring was continued for an additional 1 h at −78° C. The reaction mixture was quenched with a saturated $NH_4Cl$ solution and extracted with EtOAc (2×100 mL). The combined organic layers were washed with water (50 mL) and brine (50 mL), dried over $Na_2SO_4$, filtered, and concentrated in vacuo to obtain the crude product. The crude material was purified via silica gel column chromatography eluting with 15% EtOAc in hexanes to afford 4-(4-methyl-4-(trimethylsilyloxy) pent-2-ynoyl)benzonitrile (3.8 g, 68%) as a yellow oil.

4-(4-Hydroxy-4-methylpent-2-ynoyl)benzonitrile

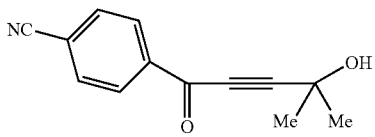

To a stirred solution of 4-(4-methyl-4-(trimethylsilyloxy) pent-2-ynoyl)benzonitrile (1.7 g, 5.00 mmol) in DCM (15 mL) was added PTSA (1.70 g, 8.90 mmol) at RT and the reaction mixture was stirred for 30 min. The reaction mixture was diluted with water (10 mL) and extracted with DCM (2×50 mL). The combined organic layers were washed with a saturated $NaHCO_3$ solution and water, dried over $Na_2SO_4$, filtered, and then concentrated in vacuo to afford 4-(4-hydroxy-4-methylpent-2-ynoyl)benzonitrile (1.20 g) as a yellow oil.

4-(5,5-Dimethyl-4-oxo-4,5-dihydrofuran-2-yl)benzonitrile

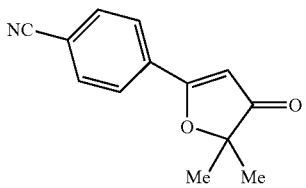

To a stirred solution of crude 4-(4-hydroxy-4-methylpent-2-ynoyl)benzonitrile (1.2 g, 5.60 mmol) in ethanol (12 mL), a solution of diethyl amine (0.58 mL, 5.60 mmol) in EtOH (5 mL) was added dropwise at RT. The reaction mixture was then stirred for additional 1 h. The ethanol was removed and the mixture then diluted with EtOAc (50 mL). The combined organic layers were washed with water (10 mL), brine (10 mL), dried over $Na_2SO_4$, filtered, and concentrated in vacuo to afford crude 4-(5,5-dimethyl-4-oxo-4,5-dihydrofuran-2-yl)benzonitrile (1.2 g) as a light green semi solid which was taken on to the next step without further purification.

4-(3-Bromo-5,5-dimethyl-4-oxo-4,5-dihydrofuran-2-yl)benzonitrile

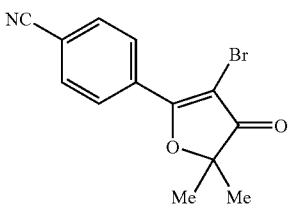

To a stirred solution of 4-(5,5-dimethyl-4-oxo-4,5-dihydrofuran-2-yl)benzonitrile (1.2 g, 5.60 mmol) in $CHCl_3$ (12 mL), NBS (1.1 g, 6.00 mmol) was added portionwise at RT. The reaction mixture was then stirred for 3 h and diluted with DCM (100 mL). The combined organic layers were washed with water (30 mL) and brine (30 mL), dried over $Na_2SO_4$, filtered, and then concentrated in vacuo to obtain the crude product. The crude material was purified via silica gel column chromatography to afford 4-(3-bromo-5,5-dimethyl-4-oxo-4,5-dihydrofuran-2-yl)benzonitrile (0.50 g, 31%) as an off white solid.

4-(3-(4-(benzyloxy)phenyl)-5,5-dimethyl-4-oxo-4,5-dihydrofuran-2-yl)benzonitrile

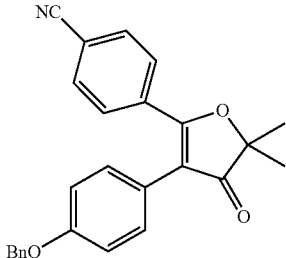 [SMILES: CC1(C)OC(c2ccc(C#N)cc2)=C(c2ccc(OCc3ccccc3)cc2)C1=O]

A solution of 4-(3-bromo-5,5-dimethyl-4-oxo-4,5-dihydrofuran-2-yl)benzonitrile (29.0 g, 107.4 mmol), 2-(4-(benzyloxy)phenyl)-4,4,5,5-tetramethyl-1,3,2-dioxaborolane (34.7 g, 118.8 mmol), and $Cs_2CO_3$ (104.7 g, 322.2 mmol) in toluene (200 mL) and water (50 mL) was degassed. Dichloro[1,1'-bis(diphenylphosphino)ferrocene]palladium(II) (8.5 g, 10 mmol) was added under an inert atmosphere and the solution was again degassed. The reaction was then refluxed for 3 h and monitored for completion by TLC. Upon complete consumption of the starting material, the reaction mixture was filtered through a bed of Celite® washing with ethyl acetate. The organic layer was then washed with water, brine, dried over $Na_2SO_4$, filtered and concentrated under reduced pressure. The residue was purified by flash column chromatography using 20% ethyl acetate in n-hexane on 230-400 mesh silica gel (Rf=0.3) to afford 4-(3-(4-(benzyloxy)phenyl)-5,5-dimethyl-4-oxo-4,5-dihydrofuran-2-yl)benzonitrile (31.5 g, 74.25%) as solid. $^1$H NMR: 500 MHz, DMSO-$d_6$: δ 7.95 (d, 2H), 7.75 (d, 2H), 7.5 (d, 4H), 7.35 (t, 1H), 7.15 (d, 2H), 7.05 (d, 2H), 5.1 (s, 2H), 1.45 (s, 6H). MS: [M+H]+: m/z=396.0. HPLC: (99.5%, Eclipse XDB-C18, 150×4.6 mm, 5 um. Mobile Phase: 0.1% TFA in Water. (A). ACN (B), Flow rate: 1.5 ml/min).

4-(3-(4-Hydroxyphenyl)-5,5-dimethyl-4-oxo-4,5-dihydrofuran-2-yl) benzonitrile

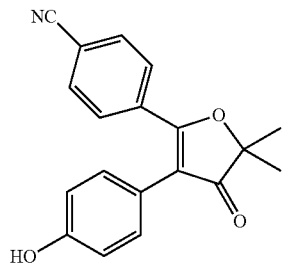 [SMILES: CC1(C)OC(c2ccc(C#N)cc2)=C(c2ccc(O)cc2)C1=O]

Boron tribromide (3.4 g, 15.8 mmol) was added to a solution of 4-(3-(4-(benzyloxy)phenyl)-5,5-dimethyl-4-oxo-4,5-dihydrofuran-2-yl)benzonitrile (2.5 g, 6.3 mmol) in DCM at 0° C. & the mixture was stirred for 1 h (reaction was monitored by TLC). Upon complete consumption of the starting material, the mixture was quenched with chilled water and extracted with DCM. The combined organics were dried over sodium sulfate, filtered and concentrated under reduced pressure. The residue was purified by column chromatography to afford 4-(3-(4-hydroxyphenyl)-5,5-dimethyl-4-oxo-4,5-dihydrofuran-2-yl)benzonitrile (1.8 g, 93.2%) as yellow solid. $^1$H NMR: 500 MHz, CDCl$_3$: δ 9.6 (s, 1H), 7.95 (d, 2H), 7.75 (d, 2H), 7.0 (d, 2H), 6.75 (d, 2H), 1.5 (s, 6H).

2,3,5-Trimethylpyridine 1-oxide

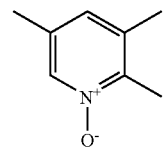

3-Chloro per benzoic acid (10 g, 164.2 mmol) was added to a solution of 2,3,5-trimethylpyridine (10 g, 82.1 mmol) in DCM at 0° C. and the mixture was stirred at RT for 8 h (the reaction was monitored by TLC). The reaction was quenched with sodium bicarbonate solution and stirred for 1 h at RT. The organic layer was separated, dried over sodium sulfate, filtered and concentrated under reduced pressure to afford 2,3,5-trimethylpyridine 1-oxide (6.5 g, 58.0%) as a brown solid. $^1$H NMR: 200 MHz, CDCl$_3$: δ 8.15 (s, 1H), 7.15 (s, 1H), 2.55 (s, 3H), 2.35 (s, 3H), 2.25 (s, 3H). MS: [M+H]+: m/z=311.2.

2-(Chloromethyl)-3,5-dimethylpyridine

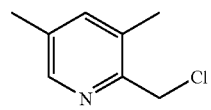

Tosyl chloride (12.5 g, 65.6 mmol) was added to a solution of 2,3,5-trimethylpyridine 1-oxide (6.0 g, 43.7 mmol), and triethylamine (6.6 g, 65.6 mmol) in DCM (60 ml) at RT under an atmosphere of nitrogen. The reaction mixture was heated to reflux and reflux was maintained 4 h (reaction was monitored by TLC). The reaction was quenched with water and extracted with DCM. The combined organics were dried over sodium sulfate, filtered and concentrated under reduced pressure. The residue was purified by flash column chromatography using 10% ethyl acetate in n-hexanes and silica gel (230-400 Mesh) to afford 2-(chloromethyl)-3,5-dimethylpyridine (4.5 g, 66.1%) as a brown thick syrup. $^1$H NMR: 200 MHz, CDCl₃: δ 8.15 (s, 1H), 7.45 (s, 1H), 4.75 (s, 2H), 2.35 (s, 3H), 2.25 (s, 3H). MS: [M+H]+: m/z=156.3.

4-(4-((3,5-dimethylpyridin-2-yl)methoxy)phenyl)-5-(4-methoxyphenyl)-2,2-dimethylfuran-3(2H)-one

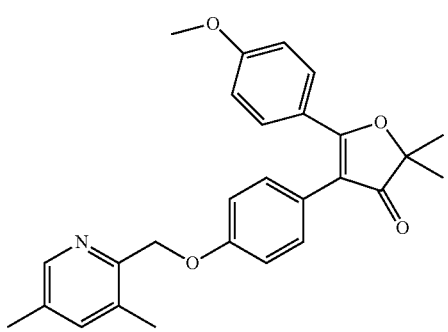

4-(4-Hydroxyphenyl)-5-(4-methoxyphenyl)-2,2-dimethylfuran-3(2H)-one (3.0 g, 9.6 mmol) was added to a mixture of cesium carbonate (12.6 g, 38.6 mmol) and DMF (1000 mL) at RT under an atmosphere of nitrogen. The reaction mixture was stirred at RT for 30 min upon which 2-(chloromethyl)-3,5-dimethylpyridine (2.25 g, 14.5 mmol) was added. The reaction mixture was heated for 4 h at 80° C. (the reaction was monitored by TLC). The reaction mixture was diluted with water and extracted with EtOAc. The combined organics were dried over sodium sulfate, filtered and concentrated under reduced pressure. The residue was purified by flash column chromatography using 15% ethyl acetate in n-hexane and silica gel (230-400 mesh) to afford 4-(4-((3,5-dimethylpyridin-2-yl)methoxy)phenyl)-5-(4-methoxyphenyl)-2,2-dimethylfuran-3(2H)-one (3.2 g, 65.3%) as an off-white solid. ¹H NMR: 500 MHz, DMSO-d₆: δ 8.2 (s, 1H), 7.65 (d, 2H), 7.45 (s, 1H), 7.15 (d, 2H), 7.1 (d, 2H), 7.0 (d, 2H), 5.2 (s, 2H), 3.8 (s, 3H), 2.35 (s, 3H), 2.3 (s, 3H), 1.45 (s, 6H). MS: [M+H]+: m/z=430.4. HPLC (96.3%, Condition-A).

4-(4-((3,5-dimethylpyridin-2-yl)methoxy)phenyl)-5-(4-methoxyphenyl)-2,2-dimethylfuran-3(2H)-one methanesulfonate

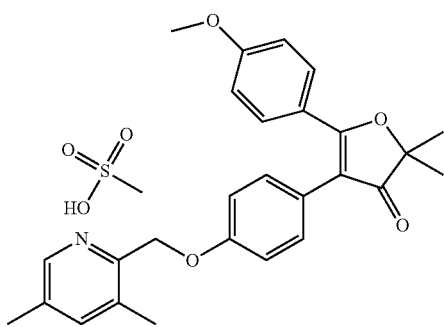

Methanesulfonic acid (445.0 mg, 4.6 mmol) was added to a solution of 4-(4-((3,5-dimethylpyridin-2-yl)methoxy)phenyl)-5-(4-methoxyphenyl)-2,2-dimethylfuran-3(2H)-one (2.01 g, 4.6 mmol) in DCM (3 ml) and diethyl ether (150 mL) at RT under an atmosphere of nitrogen. The reaction mixture was stirred at RT for 4 h and the solids were removed by filtration. The solid was washed with 20% DCM in diethyl ether and dried under vacuo to afford 4-(4-((3,5-dimethylpyridin-2-yl)methoxy)phenyl)-5-(4-methoxyphenyl)-2,2-dimethylfuran-3(2H)-one methanesulfonate (2.1 g, 87%) as a white solid. ¹H NMR: 500 MHz, DMSO-d₆: δ 8.2 (s, 1H), 7.65 (d, 2H), 7.45 (s, 1H), 7.15 (d, 2H), 7.1 (d, 2H), 7.0 (d, 2H), 5.2 (s, 2H), 3.8 (s, 3H), 2.35 (s, 3H), 2.3 (s, 3H), 1.45 (s, 6H), HPLC: (98.9%, Condition-A).

2-(Chloromethyl) imidazo[1,2-a]pyridine

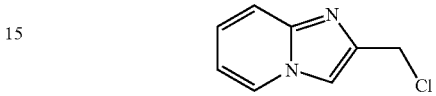

1,3-Dichloroacetone (22.9 g, 180.3 mmol) was added to a solution of 2-amino pyridine (10 g, 106.3 mmol) in acetonitrile (200 ml). The mixture was heated at reflux for 14 h (the reaction was monitored by TLC). Upon completion of the reaction, the volatiles were removed under reduced pressure. The residue was diluted with water and adjusted the pH to 7.5 with sodium bicarbonate solution which was extracted with EtOAc. The combined organics were dried over sodium sulfate, filtered and concentrated under reduced pressure. The residue was purified by flash column chromatography using 12% ethyl acetate in n-hexanes and silica gel (230-400 mesh) to afford 2-(chloromethyl) imidazo[1,2-a]pyridine (8.0 g, 47.9%) as pale yellow solid. ¹H NMR: 200 MHz, CDCl₃: δ 8.15 (d, 1H), 7.6 (dd, 2H), 7.1 (t, 1H), 6.8 (t, 1H), 4.75 (s, 2H). MS: [M+H]+: m/z=167.2.

4-(4-(Imidazo[1,2-a]pyridin-2-ylmethoxy)phenyl)-5-(4-methoxyphenyl)-2,2-dimethylfuran-3(2H)-one

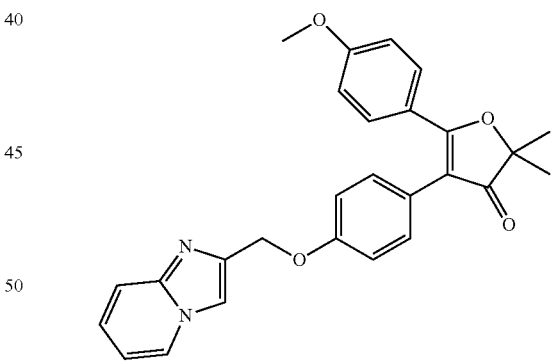

4-(4-Hydroxyphenyl)-5-(4-methoxyphenyl)-2,2-dimethylfuran-3(2H)-one (2.5 g, 8.06 mmol) was added to a mixture of cesium carbonate (10.5 g, 32.2 mmol) and DMF (20 mL) at RT under nitrogen. The reaction mixture was stirred at RT for 30 min, upon which 2-(chloromethyl) imidazo[1,2-a]pyridine (2.4 g, 12.0 mmol) was added. The mixture was heated at 80° C. for 4 h (reaction was monitored by TLC). The reaction mixture was allowed to cool to RT, diluted with water and extracted with EtOAc. The combined organics were dried over sodium sulfate, filtered and concentrated under reduced pressure. The residue was purified by flash column chromatography using 20% ethyl acetate in n-hexane and silica gel (230-400 mesh), to afford 4-(4-(imidazo[1,2-a]pyridin-2-ylmethoxy)phenyl)-5-(4-methoxyphenyl)-2,2-dimethylfuran-3(2H)-one (2.8 g, 77.7%) as Off-white solid. ¹H NMR: 500 MHz, DMSO-d₆: δ 8.55 (d, 1H), 8.0 (s, 1H), 7.55 (Ar, 3H), 7.3-6.85 (Ar, 8H), 5.15 (s, 2H), 3.85 (s, 3H), 1.25 (s, 6H). MS: [M+H]+: m/z=441.2. HPLC: (97.3%, Condition-A).

4-(4-(Imidazo[1,2-a]pyridin-2-ylmethoxy)phenyl)-5-(4-methoxyphenyl)-2,2-dimethylfuran-3(2H)-one methanesulfonate

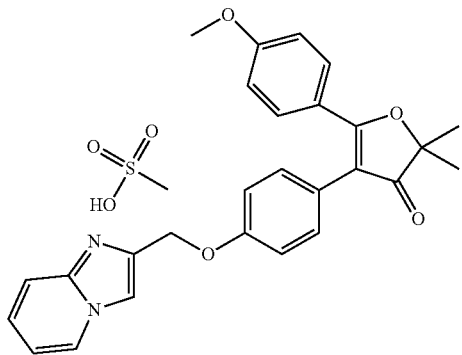

Methanesulfonic acid (531 mg, 5.5 mmol) was added to a solution of 4-(4-(imidazo[1,2-a]pyridin-2-ylmethoxy)phenyl)-5-(4-methoxyphenyl)-2,2-dimethylfuran-3(2H)-one (2.5 g, 5.5 mmol) in DCM (5 ml) and diethyl ether (150 mL) at RT under an atmosphere of nitrogen. The reaction mixture was stirred for a further 4 h at RT. The solids were collected by filtration, washed with 20% DCM in diethyl ether and dried in vacuo to afford 4-(4-(imidazo[1,2-a]pyridin-2-ylmethoxy)phenyl)-5-(4-methoxyphenyl)-2,2-dimethylfuran-3(2H)-one methanesulfonate (2.4 g, 82.7%) as white solid. ¹H NMR: 500 MHz, DMSO-d₆: δ 8.75 (d, 1H), 8.1 (s, 1H), 7.65 (Ar, 3H), 7.3-6.85 (Ar, 8H), 5.2 (s, 2H), 3.85 (s, 3H), 1.25 (s, 6H), HPLC: (98.8%, Condition-A).

6-Chloroimidazo[1,2-b]pyridazine

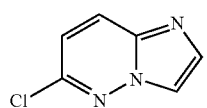

Bromoacetaldehyde diethylacetal (36.5 g, 216 mmol) was added to a solution of aq.cHBr (7.2 ml) and then heated to reflux for 30 min. The mixture was then cooled to 0° C., upon which ethanol (236 ml), sodium bicarbonate (8.09 g, 95 mmol) and 6-chloropyridazin-3-amine (4 g, 30 mmol) were added. The mixture was heated to 80° C. for 3 h (reaction was monitored by TLC) and then allowed to cool to RT. The mixture was concentrated under reduced pressure, diluted with water and extracted with EtOAc. The combined organics were dried over sodium sulfate, filtered and concentrated under reduced pressure. The residue was purified by flash column chromatography using 15% ethyl acetate in n-hexane and silica gel (230-400 mesh), to afford 6-chloroimidazo[1,2-b]pyridazine (4.0 g, 85.2%) as Off-white solid. ¹H NMR: 200 MHz, CDCl₃: δ 7.4-7.2 (Ar, 4H), 3.85 (q, 1H), 3.4 (q, 1H), 3.2 (q, 2H), 1.35 (t, 3H), 1.1 (t, 3H). MS: [M+H]+: m/z=154.3.

Methylimidazo[1,2-b]pyridazine-6-carboxylate

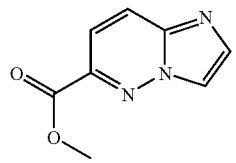

6-Chloroimidazo[1,2-b]pyridazine (5.0 g, 32 mmol) was added to a solution of methanol (75 ml) and acetonitrile (75 ml) in a steel bomb at RT under nitrogen bubbling. Triethylamine (4.0 g, 39.4 mmol), BINAP (2.0 g, 3.0 mmol) and bisacetonitrile palladium dichloride (0.854 g, 3.0 mmol) were then added to the mixture. The mixture was heated to 100° C. which was maintained for approximately 10 hours (the reaction was monitored by TLC). The reaction mixture was filtered through a bed of Celite® washing with ethyl acetate. The organics were washed with water and brine, dried over sodium sulfate and concentrated under reduced pressure. The residue was purified by flash column chromatography using 10% ethyl acetate in n-hexane and silica gel (230-400 mesh) to afford methyl imidazo[1,2-b]pyridazine-6-carboxylate (2.5 g, 43%) as an off-white solid. ¹H NMR: 200 MHz, DMSO-d₆₃: δ 8.55 (s, 1H), 8.3 (d, 1H), 7.95 (s, 1H), 7.55 (d, 1H), 3.95 (s, 3H). MS: [M+H]+: m/z=177.9.

Imidazo[1,2-b]pyridazin-6-ylmethanol

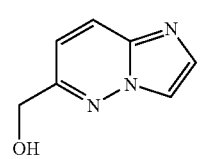 [SMILES: OCc1ccc2nccn2n1]

Sodium borohydride (1.1 g, 31.1 mmol) was added to a solution of methyl imidazo[1,2-b]pyridazine-6-carboxylate (2.4 g, 15.5 mmol) in THF (35 mL) and methanol (2.5 ml) at RT. The reaction mixture was stirred at RT for 2 h (the reaction was monitored by TLC) upon which the mixture was concentrated under reduced pressure. The reaction mixture was diluted with water and extracted with EtOAc. The combined organics were dried over sodium sulfate, filtered and concentrated under reduced pressure to afford imidazo[1,2-b]pyridazin-6-ylmethanol (1.6 g, 81%) as a white solid. ¹H NMR: 200 MHz, DMSO-d$_6$: δ 8.5 (s, 1H), 8.3 (d, 1H), 7.9 (s, 1H), 7.55 (d, 1H), 5.65 (t, 1H), 4.6 (d, 2H). MS: [M+H]+: m/z=311.2.

6-(Chloromethyl) imidazo[1,2-b]pyridazine

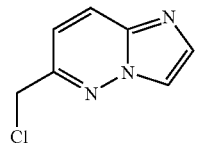 [SMILES: ClCc1ccc2nccn2n1]

Thionyl chloride (10 ml) was added to imidazo[1,2-b]pyridazin-6-ylmethanol (1.5 g, 9.0 mmol) at 20° C. under an atmosphere of nitrogen at RT. The reaction mixture was stirred at reflux for 3 h (the reaction was monitored by TLC) upon which the volatiles were removed under reduced pressure. The reaction mixture was diluted with water and extracted with EtOAc. The combined organics were dried over sodium sulfate, filtered and concentrated under reduced pressure. The residue was purified by flash column chromatography using 15% ethyl acetate in n-hexane and silica gel (230-400 mesh) to afford 6-(chloromethyl) imidazo[1,2-b]pyridazine (1.2 g, 69%) as an off-white solid. $^1$H NMR, 200 MHz, DMSO-d$_6$: δ 8.35 (s, 1H), 8.3 (d, 1H), 7.85 (s, 1H), 7.35 (d, 1H), 4.95 (s, 2H). MS: [M+H]+: m/z=149.9.

4-(4-(Imidazo[1,2-b]pyridazin-6-ylmethoxy)phenyl)-5-(4-methoxyphenyl)-2,2-dimethylfuran-3(2H)-one

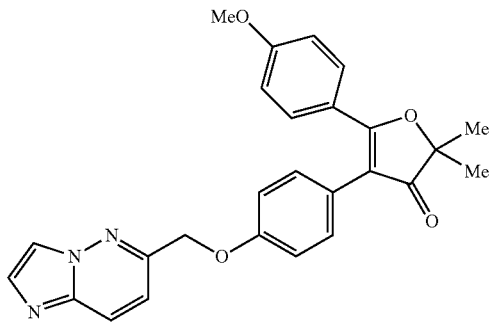 [SMILES: COc1ccc(C2=C(c3ccc(OCc4ccc5nccn5n4)cc3)C(=O)C(C)(C)O2)cc1]

4-(4-Hydroxyphenyl)-5-(4-methoxyphenyl)-2,2-dimethylfuran-3(2H)-one (1.2 g, 3.8 mmol) was added to a mixture of cesium carbonate (3.7 g, 11.6 mmol) and DMF (25 mL) at RT under an atmosphere of nitrogen. The reaction mixture was stirred at RT for 30 min upon which 6-(chloromethyl) imidazo[1,2-b]pyridazine (0.96 g, 5 mmol) was added. The mixture was heated at 80° C. for 4 h (the reaction was monitored by TLC). The reaction mixture was diluted with water and extracted with EtOAc. The combined organics were dried over sodium sulfate, filtered and concentrated under reduced pressure. The residue was purified by flash column chromatography using 30% ethyl acetate in n-hexane and silica gel (230-400 mesh) to afford 4-(4-(imidazo[1,2-b]pyridazin-6-ylmethoxy)phenyl)-5-(4-methoxyphenyl)-2,2-dimethylfuran-3(2H)-one (0.8 g, 47%) as Off-white solid. $^1$H NMR: 200 MHz, DMSO-d$_6$: δ 8.35 (s, 1H), 8.2 (d, 1H), 7.8 (s, 1H), 7.55 (d, 2H), 7.4 (d, 1H), 7.2 (d, 2H), 7.1 (d, 2H), 7.0 (d, 2H), 5.3 (s, 2H), 3.9 (s, 3H), 1.45 (s, 6H). MS: [M+H]+: m/z=442.1. HPLC: (95.8%, Condition-A).

4-(4-(Imidazo[1,2-b]pyridazin-6-ylmethoxy)phenyl)-5-(4-methoxyphenyl)-2,2-dimethylfuran-3(2H)-one methanesulfonate

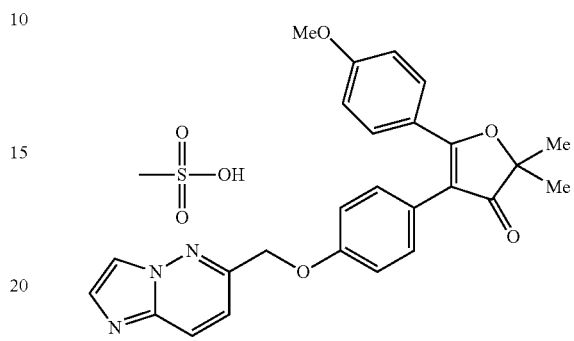

Methanesulfonic acid (54 mg, 0.5 mmol) was added to a solution of compound 4-(4-(imidazo[1,2-b]pyridazin-6-ylmethoxy)phenyl)-5-(4-methoxyphenyl)-2,2-dimethylfuran-3(2H)-one (250 mg, 0.5 mmol) in DCM (2 ml) and diethyl ether (20 mL) at RT under an atmosphere of nitrogen. The reaction mixture was stirred at RT for 4 h upon which the mixture was filtered and the solids were washed with 20% DCM in diethyl ether and dried in vacuo to afford 4-(4-(imidazo[1,2-b]pyridazin-6-ylmethoxy)phenyl)-5-(4-methoxyphenyl)-2,2-dimethylfuran-3(2H)-one methanesulfonate (240 mg, 80.0%) as an off-white solid. $^1$H NMR: 200 MHz, DMSO-d$_6$: δ 8.55 (s, 1H), 8.35 (d, 1H), 78.1 (s, 1H), 7.65 (d, 2H), 7.4 (d, 1H), 7.2 (d, 2H), 7.1 (d, 2H), 7.0 (d, 2H), 5.35 (s, 2H), 3.9 (s, 3H), 2.35 (s, 3H), 1.45 (s, 6H). HPLC: (98.3%, Condition-A).

6-Chloro-2-(chloromethyl) imidazo[1,2-b]pyridazine

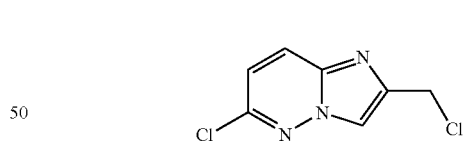

1,3-Dichloroacetone (21.4 g, 168.0 mmol) was added to a solution of 6-chloropyridazin-3-amine (10 g, 77.2 mmol) in acetonitrile (200 ml). The mixture was heated at reflux for 14 h (the reaction was monitored by TLC). The volatiles were removed under reduced pressure and the reaction mixture was diluted with water. The pH was adjusted to ~7.5 with sodium bicarbonate solution and then extracted with EtOAc. The combined organics were dried over sodium sulfate, filtered and concentrated under reduced pressure. The residue was purified by flash column chromatography using 14% ethyl acetate in n-hexane and silica gel (230-400 mesh) to afford 6-chloro-2-(chloromethyl) imidazo[1,2-b]pyridazine (6.0 g, 64.1%) as white solid. ¹H NMR: 200 MHz, CDCl₃: δ 8.0 (s, 1H), 7.9 (d, 1H), 7.1 (d, 1H), 4.75 (s, 2H). MS: [M+H]+: m/z=202.8.

4-(4-((6-Chloroimidazo[1,2-b]pyridazin-2-yl)methoxy)phenyl)-5-(4-methoxyphenyl)-2,2-dimethylfuran-3(2H)-one

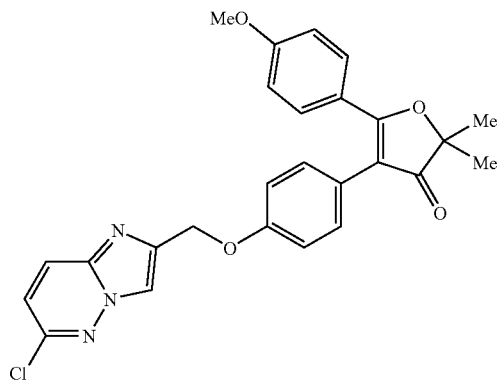 [SMILES: COc1ccc(C2=C(c3ccc(OCc4cn5nc(Cl)ccc5n4)cc3)C(=O)C(C)(C)O2)cc1]

4-(4-Hydroxyphenyl)-5-(4-methoxyphenyl)-2,2-dimethylfuran-3(2H)-one (200 mg, 0.64 mmol) was added to a mixture of cesium carbonate (838 mg, 2.5 mmol) and DMF (5 mL) at RT under an atmosphere of nitrogen. The reaction mixture was stirred at RT for 30 min upon which 6-chloro-2-(chloromethyl) imidazo[1,2-b]pyridazine (196 mg, 9.6 mmol) was added. The mixture was heated at 80° C. for 4 h (the reaction was monitored by TLC). The reaction mixture was diluted with water and extracted with EtOAc; the combined organics were dried over sodium sulfate, filtered and concentrated under reduced pressure. The organic residue was purified by flash column chromatography using 30% ethyl acetate in n-hexane and silica gel (230-400 mesh) to afford 4-(4-((6-chloroimidazo[1,2-b]pyridazin-2-yl)methoxy)phenyl)-5-(4-methoxyphenyl)-2,2-dimethylfuran-3(2H)-one (180 mg, 63.0%) as an off-white solid. ¹H NMR, 500 MHz, DMSO-d₆: δ 8.45 (s, 1H), 8.2 (d, 1H), 7.55 (d, 2H), 7.4 (d, 1H), 7.15 (d, 2H), 7.1 (d, 2H), 7.0 (d, 2H), 5.25 (s, 2H), 3.8 (s, 3H), 1.25 (s, 6H). MS: [M+H]+: m/z=476.7. HPLC: (96.7%, Condition-A).

4-(4-(Imidazo[1,2-b]pyridazin-2-ylmethoxy)phenyl)-5-(4-methoxyphenyl)-2,2-dimethylfuran-3(2H)-one

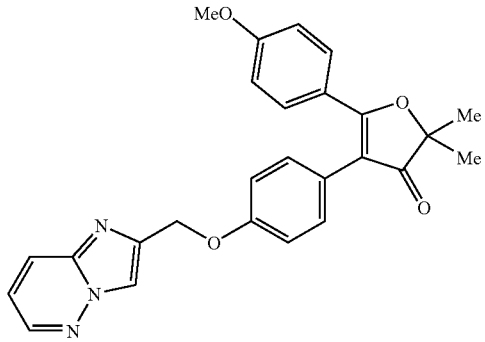 [SMILES: COc1ccc(C2=C(c3ccc(OCc4cn5ncccc5n4)cc3)C(=O)C(C)(C)O2)cc1]

Palladium hydroxide (36 mg) was added to a solution of 4-(4-((6-chloroimidazo[1,2-b]pyridazin-2-yl)methoxy)phenyl)-5-(4-methoxyphenyl)-2,2-dimethylfuran-3(2H)-one (180 mg, 0.37 mmol) and diethyl amine (28 mg, 0.37) in methanol (25 ml) at RT under an atmosphere of nitrogen. The nitrogen atmosphere was exchanged for hydrogen and was stirred at RT for 2 h (the reaction was monitored by TLC). The compound was filtered through a bed of Celite® bed washing with methanol. The filtrate was concentrated under reduced pressure to afford 4-(4-(imidazo[1,2-b]pyridazin-2-ylmethoxy)phenyl)-5-(4-methoxyphenyl)-2,2-dimethylfuran-3(2H)-one (160 mg, 96.7%) as a white solid. ¹H NMR: 500 MHz, DMSO-d₆: δ 8.45 (s, 1H), 8.4 (s, 1H) 8.15 (d, 1H), 7.55 (d, 2H), 7.25 (d, 1H), 7.15 (d, 2H), 7.1 (d, 2H), 7.0 (d, 2H), 5.25 (s, 2H), 3.8 (s, 3H), 1.25 (s, 6H). MS: [M+H]+: m/z=442.3. HPLC: (97.4%, Condition-A).

4-(4-(Imidazo[1,2-b]pyridazin-2-ylmethoxy)phenyl)-5-(4-methoxyphenyl)-2,2-dimethylfuran-3(2H)-one methanesulfonate

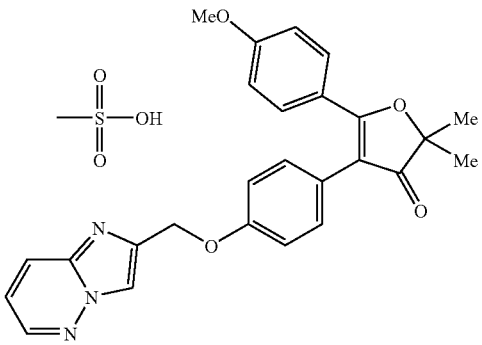

Methanesulfonic acid (34.8 mg, 0.36 mmol) was added to a solution of compound 4-(4-(imidazo[1,2-b]pyridazin-2-ylmethoxy)phenyl)-5-(4-methoxyphenyl)-2,2-dimethylfuran-3(2H)-one (160 mg, 0.36 mmol) in DCM (3 ml) and diethyl ether (15 mL) at RT under an atmosphere of nitrogen. The reaction mixture was stirred at RT for 4 h, upon which the mixture was filtered and the solids were washed with 20% DCM in diethyl ether. The solids were dried under vacuo to afford 4-(4-(imidazo[1,2-b]pyridazin-2-ylmethoxy)phenyl)-5-(4-methoxyphenyl)-2,2-dimethylfuran-3(2H)-one methanesulfonate (110 mg, 56%) as a white solid. ¹H NMR: 500 MHz, DMSO-d₆: δ 8.45 (s, 1H), 8.4 (s, 1H) 8.15 (d, 1H), 7.55

(d, 2H), 7.25 (d, 1H), 7.15 (d, 2H), 7.1 (d, 2H), 7.0 (d, 2H), 5.25 (s, 2H), 3.8 (s, 3H), 2.35 (s, 3H), 1.25 (s, 6H), HPLC: (98.5%, Condition-A).

4-(3-(4-((3,5-dimethylpyridin-2-yl)methoxy)phenyl)-5,5-dimethyl-4-oxo-4,5-dihydrofuran-2-yl)benzonitrile

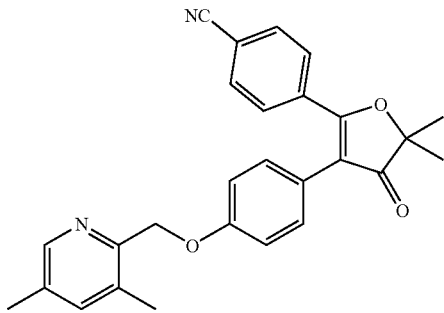

4-(3-(4-Hydroxyphenyl)-5,5-dimethyl-4-oxo-4,5-dihydrofuran-2-yl)benzonitrile (1.5 g, 4.9 mmol) was added to a mixture of carbonate (6.3 g, 19.6 mmol) and DMF (100 mL) at RT under nitrogen. The reaction mixture was stirred at RT for 30 min upon which 2-(chloromethyl)-3,5-dimethylpyridine (1.14 g, 7.3 mmol) was added. The mixture was heated at 80° C. for 4 h (the reaction was monitored by TLC). The reaction mixture was diluted with water and extracted with EtOAc; the combined organics were dried over sodium sulfate, filtered and concentrated under reduced pressure. The residue was purified by flash column chromatography using 22% ethyl acetate in n-hexane and silica gel (230-400 mesh) to afford 4-(3-(4-((3,5-dimethylpyridin-2-yl)methoxy)phenyl)-5,5-dimethyl-4-oxo-4,5-dihydrofuran-2-yl) (0.70 g, 35%) as yellow solid. $^1$H NMR, 200 MHz, CDCl$_3$: δ 7.45-6.8 (Ar, 11H), 4.9 (d, 1H), 4.6 (d, 1H), 3.75 (s, 3H), 3.2 (d, 2H) 3.1 (q, 1H), 2.5 (q, 1H) 0.95 (t, 6H). MS: [M+H]+: m/z=425.2. HPLC: (96.3%, Condition-A).

4-(3-(4-((3,5-Dimethylpyridin-2-yl)methoxy)phenyl)-5,5-dimethyl-4-oxo-4,5-dihydrofuran-2-yl)benzonitrile methanesulfonate

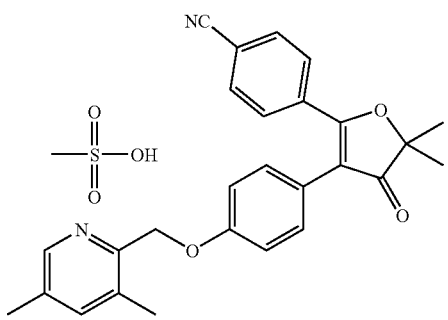

Methanesulfonic acid (158 mg, 1.6 mmol) was added to a solution of compound 4-(3-(4-((3,5-dimethylpyridin-2-yl)methoxy)phenyl)-5,5-dimethyl-4-oxo-4,5-dihydrofuran-2-yl) (700 mg, 1.6 mmol) in DCM (0.5 ml) and diethyl ether (15 mL) at RT under an atmosphere of nitrogen. The reaction mixture was stirred at RT for 4 h upon which, the mixture was filtered and the solids were washed with 20% DCM in diethyl ether and dried in vacuo to afford 4-(3-(4-(3,5-dimethylpyridin-2-yl)methoxy)phenyl)-5,5-dimethyl-4-oxo-4,5-dihydrofuran-2-yl)benzonitrile methanesulfonate (2.1 g, 75%) as a white solid. $^1$H NMR: 200 MHz, CDCl$_3$: δ 8.2 (d, 1H), 7.5 (t, 1H), 7.3-6.8 (Ar, 9H) 5.1 (s, 2H), 4.05 (s, 2H), 3.8 (s, 3H), HPLC: (97.1%, Condition-A).

4-(3-(4-(Imidazo[1,2-a]pyridin-2-ylmethoxy)phenyl)-5,5-dimethyl-4-oxo-4,5-dihydrofuran-2-yl) benzonitrile

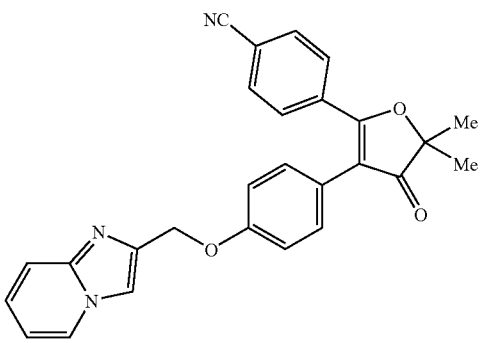

4-(3-(4-Hydroxyphenyl)-5,5-dimethyl-4-oxo-4,5-dihydro furan-2-yl)benzonitrile (3.15 g, 10.3 mmol) was added to a mixture of cesium carbonate (13.4 g, 41.3 mmol) and DMF (100 mL) at RT under an atmosphere of nitrogen. The reaction mixture was stirred at RT for 30 min upon which 2-(chloromethyl)imidazo[1,2-a]pyridine (2.0 g, 12.3 mmol) was added. The mixture was heated at 80° C. for 4 h (the reaction was monitored by TLC). The reaction mixture was diluted with water and extracted with EtOAc, the combined organics were dried over sodium sulfate, filtered and concentrated under reduced pressure. The residue was purified by flash column chromatography using 20% ethyl acetate in n-hexane and silica gel (230-400 mesh) to afford 4-(3-(4-(imidazo[1,2-a]pyridin-2-ylmethoxy)phenyl)-5,5-dimethyl-4-oxo-4,5-dihydrofuran-2-yl)benzonitrile (2.7 g, 60%) as an off-white solid. $^1$H NMR: 500 MHz, DMSO-d$_6$: δ 8.55 (d, 1H), 8.0 (s, 1H), 7.55 (Ar, 3H), 7.3-6.85 (Ar, 8H), 5.15 (s, 2H), 1.25 (s, 6H). MS: [M+H]+: m/z=436.2. HPLC: (97.3%, Condition-A).

4-(3-(4-(Imidazo[1,2-a]pyridin-2-ylmethoxy)phenyl)-5,5-dimethyl-4-oxo-4,5-dihydrofuran-2-yl)benzonitrile methanesulfonate

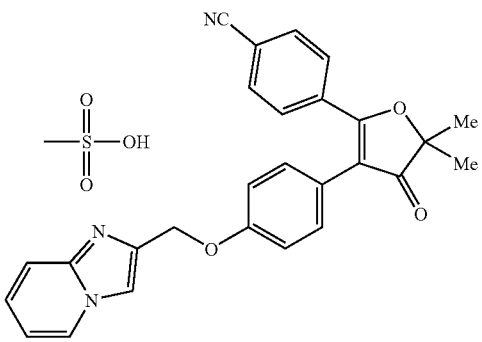

Methanesulfonic acid (309 mg, 3.2 mmol) was added to a solution of compound 4-(3-(4-(imidazo[1,2-a]pyridin-2-ylmethoxy)phenyl)-5,5-dimethyl-4-oxo-4,5-dihydrofuran-2-yl)benzonitrile (1.4 g, 3.2 mmol) in DCM (5 ml) and diethyl ether (30 mL) at RT under an atmosphere of nitrogen. The reaction mixture was stirred at RT for 4 h upon which it was filtered and the solids were washed with 20% DCM in diethyl ether and dried in vacuo to afford 4-(3-(4-(imidazo[1,2-a]pyridin-2-ylmethoxy)phenyl)-5,5-dimethyl-4-oxo-4,5-dihydrofuran-2-yl)benzonitrile methanesulfonate (1.1 g, 64%) as a white solid. $^1$H NMR: 500 MHz, DMSO-d$_6$: δ 8.55 (d, 1H), 8.0 (s, 1H), 7.55 (Ar, 3H), 7.3-6.85 (Ar, 8H), 5.15 (s, 2H), 2.15 (s, 3H), 1.25 (s, 6H), HPLC: (98.5%, Condition-A).

3-Chloro-2-(chloromethyl)imidazo[1,2-a]pyridine

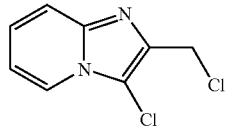 [SMILES: ClCc1nc2ccccn2c1Cl]

N-Chloro succinimide (329 g, 2.46 mmol) was added to a solution of 2-(chloromethyl)imidazo[1,2-a]pyridine (450 mg, 2.2 mmol) in DCM (15 ml) at RT under an atmosphere of nitrogen. Stirring was continued for 2 h (reaction was monitored by TLC) upon which the reaction mixture was diluted with DCM and washed with water and brine solution. The organic layer was dried over sodium sulfate, filtered and concentrated under reduced pressure. The residue was purified by flash column chromatography using 10% ethyl acetate in n-hexane and silica gel (230-400 mesh) to afford 3-chloro-2-(chloromethyl)imidazo[1,2-a]pyridine (400 mg, 76%) as Off-white solid. $^1$H NMR: 200 MHz, CDCl$_3$: δ 8.4 (d, 1H), 7.7 (d, 1H), 7.5 (t, 1H), 7.1 (t, 1H), 4.85 (s, 2H). MS: [M+H]+: m/z=201.8. HPLC: (98.3%, Condition-A).

4-(4-((3-Chloroimidazo[1,2-a]pyridin-2-yl)methoxy) phenyl)-5-(4-methoxyphenyl)-2,2-dimethylfuran-3 (2H)-one

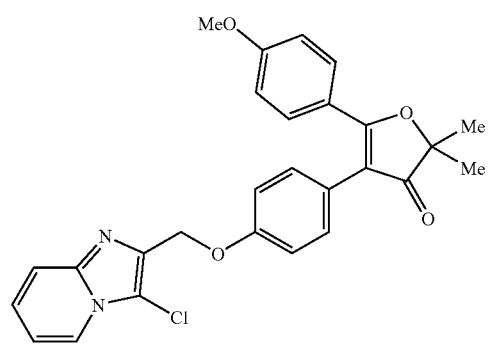 [SMILES: COc1ccc(C2=C(c3ccc(OCc4nc5ccccn5c4Cl)cc3)C(=O)C(C)(C)O2)cc1]

4-(4-Hydroxyphenyl)-5-(4-methoxyphenyl)-2,2-dimethylfuran-3(2H)-one (200 mg, 0.64 mmol) was added to a mixture of cesium carbonate (843 mg, 2.5 mmol) and DMF (20 mL) at RT under an atmosphere of nitrogen. The reaction mixture was stirred at RT for 30 min, upon which 3-chloro-2-(chloromethyl)imidazo[1,2-a]pyridine (183 mg, 0.77 mmol) was added. The mixture was heated at 80° C. for 4 h (the reaction was monitored by TLC) upon which, the mixture was diluted with water and extracted with EtOAc. The combined organics were dried over sodium sulfate, filtered and concentrated under reduced pressure. The residue was purified by flash column chromatography using 18% ethyl acetate in n-hexane and silica gel (230-400 mesh) to afford 4-(4-((3-chloroimidazo[1,2-a]pyridin-2-yl)methoxy)phenyl)-5-(4-methoxyphenyl)-2,2-dimethylfuran-3(2H)-one (250 mg, 81%) as an off-white solid. $^1$H NMR: 500 MHz, DMSO-d$_6$: δ 8.4 (d, 1H), 7.7 (d, 1H), 7.55 (Ar, 3H), 7.7-6.9 (Ar, 10H), 5.2 (s, 2H), 3.8 (s, 3H), 1.4 (s, 6H). MS: [M+H]+: m/z=470.7. HPLC: (97.2%, Condition-A).

4-(4-((3-Chloroimidazo[1,2-a]pyridin-2-yl)methoxy) phenyl)-5-(4-methoxyphenyl)-2,2-dimethylfuran-3 (2H)-one methanesulfonate

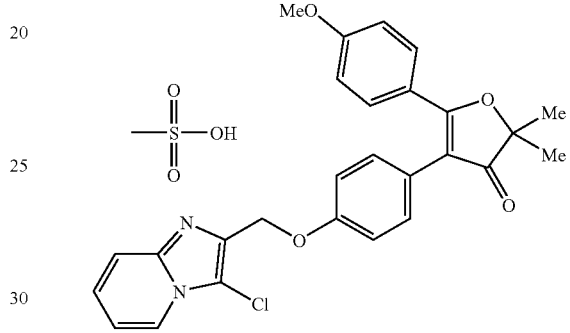

Methanesulfonic acid (50.5 mg, 0.52 mmol) was added to a solution of 4-(4-((3-chloroimidazo[1,2-a]pyridin-2-yl) methoxy)phenyl)-5-(4-methoxyphenyl)-2,2-dimethylfuran-3(2H)-one (250 mg, 0.52 mmol) in DCM (2.5 ml) and diethyl ether (25 mL) at RT under an atmosphere of nitrogen. The reaction mixture was stirred at RT for 4 h upon which the compound was filtered, washed with 20% DCM in diethyl ether and dried in vacuo to afford 4-(4-(3-chloroimidazo[1,2-a]pyridin-2-yl)methoxy)phenyl)-5-(4-methoxyphenyl)-2,2-dimethylfuran-3(2H)-one methanesulfonate (260 mg, 86%) as white solid. $^1$H NMR: 500 MHz, DMSO-d$_6$: δ 8.55 (d, 1H), 8.0 (s, 1H), 7.65 (Ar, 3H), 7.3-6.85 (Ar, 7H), 5.2 (s, 2H), 3.85 (s, 3H), 2.15 (s, 3H) 1.25 (s, 6H), HPLC: (98.8%, Condition-A).

Methyl 5-methylpicolinate

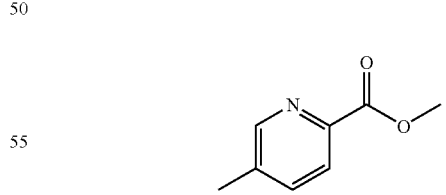

2-Chloro-5-methylpyridine (10 g, 78 mmol) was added to a solution of methanol (75 ml) and acetonitrile (75 ml) in steel bomb at RT under nitrogen bubbling followed by the addition of triethylamine (11.8 g, 117 mmol), BINAP (970 mg, 1.5 mmol) and bisacetonitrile palladium dichloride (0.4 g, 1.5 mmol). The mixture was heated to 100° C. and this temperature was maintained over night (the reaction was monitored by TLC). The reaction mixture was filter through Celite® bed and washing with ethyl acetate. The filtrate was washed with water and brine. The organic layer was concentrated under reduced pressure and purified by flash column chromatography using 10% ethyl acetate in n-hexane and silica gel (230-400 mesh) to afford methyl 5-methylpicolinate (6.5 g, 55%) as an off-white solid. $^1$H NMR: 200 MHz, CDCl$_3$: δ 8.6 (s, 1H), 8.0 (d, 1H), 7.65 (d, 1H), 4.05 (s, 3H), 2.4 (s, 3H). MS: [M+H]+: m/z=151.9.

(5-Methylpyridin-2-yl)methanol

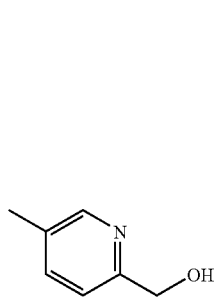

Sodium borohydride (4.5 g, 115. mmol) was added to a solution of methyl 5-methylpicolinate (6.0 g, 39.5 mmol) in THF (60 mL) and methanol (6 ml) at RT. The reaction mixture was stirred at RT for 2 h (the reaction was monitored by TLC). The mixture was concentrated under reduced pressure and the residue was diluted with water and extracted with EtOAc. The combined organics were dried over sodium sulfate, filtered and concentrated under reduced pressure. The organic layer was concentrated under vacuo to afford (5-methylpyridin-2-yl)methanol (3.5 g, 72.9%) as an off-white solid. $^1$H NMR: 200 MHz, CDCl$_3$: δ 8.5 (s, 1H), 7.7 (d, 1H), 7.15 (d, 1H), 5.0 (s, 3H), 3.4 (s, 3H). MS: [M+H]+: m/z=124.0.

2-(Chloromethyl)-5-methylpyridine

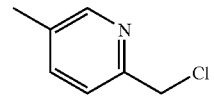

Thionyl chloride (30 ml) was added to (5-methylpyridin-2-yl)methanol (3.0 g, 24.3 mmol) at 20° C. under nitrogen. The reaction mixture was stirred at reflux for 3 h (the reaction was monitored by TLC). The reaction mixture was concentrated under reduced pressure upon which it was diluted with water and extracted with EtOAc. The combined organics were dried over sodium sulfate, filtered and concentrated under reduced pressure. The residue was purified by flash column chromatography using 6% ethyl acetate in n-hexane and silica gel (230-400 mesh), to afford 2-(chloromethyl)-5-methylpyridine (2.5 g, 73%) as an off-white solid. $^1$H NMR: 200 MHz, CDCl$_3$: δ 8.4 (s, 1H), 7.5 (d, 1H), 7.3 (d, 1H), 4.6 (s, 2H), 2.3 (s, 3H). MS: [M+H]+: m/z=142.2.

5-(4-Methoxyphenyl)-2,2-dimethyl-4-(4-((5-methylpyridin-2-yl)methoxy)phenyl)furan-3(2H)-one

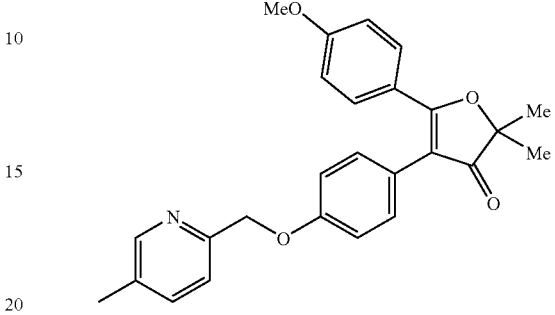

4-(4-Hydroxyphenyl)-5-(4-methoxyphenyl)-2,2-dimethylfuran-3(2H)-one (2.0, 6.5 mmol) was added to a mixture of cesium carbonate (10.5 g, 32.2 mmol) and DMF (50 mL) at RT under an atmosphere of nitrogen. The reaction mixture was stirred at RT for 30 min, upon which 2-(chloromethyl)-5-methylpyridine (1.36 g, 9.6 mmol) was added. The mixture was heated at 80° C. for 4 h (the reaction was monitored by TLC). The reaction mixture allowed to cool, diluted with water and extracted with EtOAc. The combined organics were dried over sodium sulfate, filtered and concentrated under reduced pressure. The residue was purified by flash column chromatography using 20% ethyl acetate in n-hexane and silica gel (230-400 mesh), to afford 5-(4-methoxyphenyl)-2,2-dimethyl-4-(4-((5-methylpyridin-2-yl)methoxy)phenyl)furan-3(2H)-one (2.0 g, 76.9%) as an off-white solid. $^1$H NMR: 200 MHz, DMSO-d$_6$: δ 8.4 (s, 1H), 7.6 (d, 1H), 7.55 (d, 2H), 7.4 (d, 1H), 7.2 (d, 2H), 7.1 (d, 2H), 7.0 (d, 2H), 5.2 (s, 2H), 3.8 (s, 3H), 2.3 (s, 3H), 1.45 (s, 6H). MS: [M+H]+: m/z=415.2. HPLC: (97.5%, Condition-A).

5-(4-Methoxyphenyl)-2,2-dimethyl-4-(4-((5-methylpyridin-2-yl)methoxy)phenyl)furan-3(2H)-one methanesulfonate

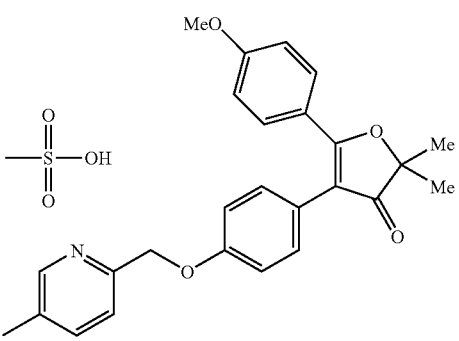

Methanesulfonic acid (462 mg, 4.8 mmol) was added to a solution of 544-methoxyphenyl)-2,2-dimethyl-4-(4-((5-methylpyridin-2-yl)methoxy)phenyl)furan-3(2H)-one (2.0 g, 4.8 mmol) in DCM (5 ml) and diethyl ether (50 mL) at RT under an atmosphere of nitrogen. The reaction mixture was stirred at RT for 4 h upon which the solids were collected by filtration, washed with 20% DCM in diethyl ether and dried in vacuo to afford 5-(4-Methoxyphenyl)-2,2-dimethyl-4-(4-((5-methylpyridin-2-yl)methoxy)phenyl)furan-3(2H)-one methanesulfonate (2.0 g, 90.9%) as a white solid. $^1$H NMR: 200 MHz, DMSO-$d_6$: δ 8.5 (s, 1H), 7.6 (d, 1H), 7.55 (d, 2H), 7.4 (d, 1H), 7.2 (d, 2H), 7.1 (d, 2H), 7.0 (d, 2H), 5.2 (s, 2H), 3.8 (s, 3H), 2.35 (s, 3H), 2.3 (s, 3H), 1.45 (s, 6H), HPLC: (99.3%, Condition-A).

4-(5,5-Dimethyl-3-(4-((5-methylpyridin-2-yl)methoxy)phenyl)-4-oxo-4,5-dihydrofuran-2-yl)benzonitrile 4-(3-(4-Hydroxyphenyl)-5,5-dimethyl-4-oxo-4,5-dihydrofuran-2-yl)benzonitrile (0.4 g, 1.3 mmol) was added to a mixture of cesium carbonate (1.7 g, 5.2 mmol) and DMF (20 mL) at RT under nitrogen. The reaction mixture was stirred at RT for 30 minutes upon which afford 2-(chloromethyl)-5-methylpyridine (306 mg, 1.9 mmol) was added. The mixture was heated at 80° C. for 4 h (the reaction was monitored by TLC). The reaction mixture was diluted with water and extracted with EtOAc. The combined organics were dried over sodium sulfate, filtered and concentrated under reduced pressure. The residue was purified by flash column chromatography using 25% ethyl acetate in n-hexane and silica gel (230-400 mesh) to afford 4-(5,5-dimethyl-3-(4-((5-methylpyridin-2-yl)methoxy)phenyl)-4-oxo-4,5-dihydrofuran-2-yl)benzonitrile (160 mg, 30.1%) as an off-white solid. $^1$H NMR: 200 MHz, DMSO-$d_6$: δ 8.4 (s, 1H), 7.6 (d, 1H), 7.55 (d, 2H), 7.4 (d, 1H), 7.2 (d, 2H), 7.1 (d, 2H), 7.0 (d, 2H), 5.2 (s, 2H), 2.3 (s, 3H), 1.45 (s, 6H). MS: [M+H]+: m/z=411.2. HPLC: (97.3%, Condition-A).

4-(5,5-Dimethyl-3-(4-((5-methylpyridin-2-yl)methoxy)phenyl)-4-oxo-4,5-dihydrofuran-2-yl)benzonitrile methanesulfonate

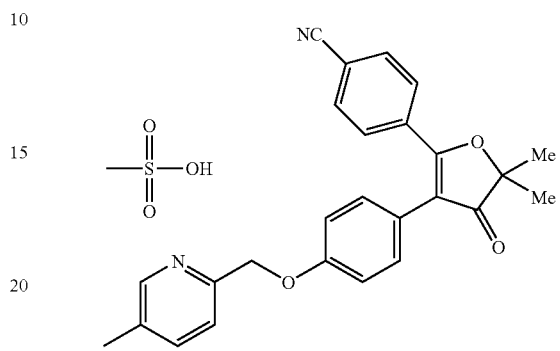

Methanesulfonic acid (36 mg, 0.3 mmol) was added to a solution of 4-(5,5-dimethyl-3-(4-((5-methylpyridin-2-yl)methoxy)phenyl)-4-oxo-4,5-dihydrofuran-2-yl)benzonitrile (150 mg, 0.3 mmol) in DCM (5 ml) and diethyl ether (50 mL) at RT under an atmosphere of nitrogen. The reaction mixture was stirred at RT for 4 h upon which the solids were collected by filtration, washed with 20% DCM in diethyl ether, dried in vacuo to afford 4-(5,5-dimethyl-3-(4-((5-methylpyridin-2-yl)methoxy)phenyl)-4-oxo-4,5-dihydrofuran-2-yl)benzonitrile methanesulfonate (120 mg, 67.0%) as a white solid. $^1$H NMR: 200 MHz, DMSO-$d_6$: δ 8.5 (s, 1H), 7.6 (d, 1H), 7.55 (d, 2H), 7.4 (d, 1H), 7.2 (d, 2H), 7.1 (d, 2H), 7.0 (d, 2H), 5.2 (s, 2H), 2.35 (s, 3H), 2.3 (s, 3H), 1.45 (s, 6H). HPLC: (98.3%, Condition-A).

Methyl 2-oxobutanoate

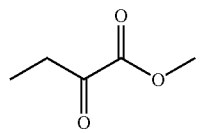

Trimethylsilyl chloride (1.06 g, 9.8 mmol) was added to a stirred solution of 2-oxobutanoic acid (10.0 g, 98.0 mmol) in 2,2-dimethoxypropane (90 ml) and methanol (20 ml). The mixture was stirred for 18 hours at RT (the reaction was monitored by TLC) upon which the mixture was concentrated under reduced pressure afford crude methyl 2-oxobutanoate (8.0 g) as a brown liquid. $^1$H NMR: 200 MHz, CDCl$_3$: δ 3.85 (s, 3H), 2.9 (q, 2H), 1.15 (t, 1H), 6.8 (t, 1H), 4.75 (s, 2H).

Methyl 3-bromo-2-oxobutanoate

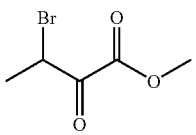

Copper bromide (30.0 g, 137 mmol) was added to a stirred solution of methyl 2-oxobutanoate (8.0 g, 68.9 mmol) in ethyl acetate (150 ml) and chloroform (100 ml). The mixture was stirred for 18 hours at reflux (the reaction was monitored by TLC). The mixture was filtered and washed with ethyl acetate and the filtrates were concentrated in vacuo to afford crude methyl 3-bromo-2-oxobutanoate (6.5 g) as a colorless liquid. $^1$H NMR: 200 MHz, CDCl$_3$: δ 5.2 (q, 1H), 3.9 (s, 3H), 1.8 (d, 3H).

Methyl 3-methylimidazo[1,2-a]pyridine-2-carboxylate

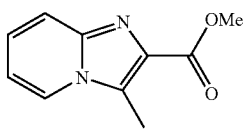

Methyl 3-bromo-2-oxobutanoate (6.5 g, 34.3 mmol) was added to a stirred solution of 2-aminopyridine (4.0 g, 42.5 mmol) in acetonitrile (100 ml). The mixture was heated at reflux for 14 h (the reaction was monitored by TLC). The mixture was concentrated in vacuo and the residue was diluted with water and the pH was to 7.5 using sodium bicarbonate solution. The mixture was extracted with EtOAc; the combined organics were dried over sodium sulfate, filtered and concentrated under reduced pressure. The residue was purified by flash column chromatography using 8% ethyl acetate in n-hexane and silica gel (230-400 mesh) to afford methyl 3-methylimidazo[1,2-a]pyridine-2-carboxylate (2.0 g, 25.1%) as a pale yellow solid. $^1$H NMR: 200 MHz, CDCl$_3$: δ 7.95 (d, 1H), 7.7 (d, 1H), 7.25 (t, 1H), 6.8 (t, 1H), 4.0 (s, 3H), 2.8 (s, 3H). MS: [M+H]+: m/z=191.1.

(3-Methylimidazo[1,2-a]pyridin-2-yl)methanol

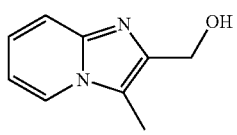

Sodium borohydride (1.5 g, 41.6 mmol) was added to a solution of methyl 3-methylimidazo[1,2-a]pyridine-2-carboxylate (2.0 g, 10.5 mmol) in THF (50 mL) and methanol (2.5 ml) at RT. The reaction mixture was stirred at RT for 2 h (the reaction was monitored by TLC) upon which the mixture was concentrated under reduced pressure. The residue was diluted with water and extracted with EtOAc. The combined organics were dried over sodium sulfate, filtered and concentrated under reduced pressure to afford (3-methylimidazo[1,2-a]pyridin-2-yl)methanol (0.8 g, 47.05%) as off-white solid. $^1$H NMR: 200 MHz, CDCl$_3$: δ 7.45 (d, 1H), 7.6 (d, 1H), 7.2 (t, 1H), 6.8 (t, 1H), 4.85 (s, 2H), 2.45 (s, 3H). MS: [M+H]+: m/z=162.9.

2-(Chloromethyl)-3-methylimidazo[1,2-a]pyridine

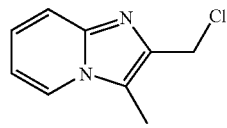

Thionyl chloride (10 ml) was added to (3-methylimidazo[1,2-a]pyridin-2-yl)methanol (0.8 g, 4.9 mmol) at 20° C. under an atmosphere of nitrogen. The reaction mixture was stirred at reflux for 3 h (the reaction was monitored by TLC). The mixture was concentrated under reduced pressure, the residue was diluted with water and extracted with EtOAc. The combined organics were dried over sodium sulfate, filtered and concentrated under reduced pressure. The residue was purified by flash column chromatography using 6% ethyl acetate in n-hexane and silica gel (230-400 mesh) to afford 2-(chloroethyl)-3-methylimidazo[1,2-a]pyridine (400 mg, 45.4%) as an off-white solid. $^1$H NMR: 200 MHz, CDCl$_3$: δ 8.15 (s, 1H), 7.6 (s, 1H), 7.55 (d, 1H), 7.15 (d, 1H), 4.75 (s, 21-1). MS: [M+H]+: m/z=181.3.

5-(4-Methoxyphenyl)-2,2-dimethyl-4-(4-((3-methylimidazo[1,2-a]pyridin-2-yl)methoxy)phenyl)furan-3(2H)-one

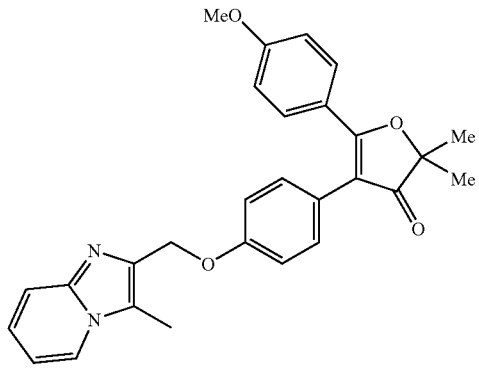 [SMILES: COc1ccc(C2=C(c3ccc(OCc4nc5ccccn5c4C)cc3)C(=O)C(C)(C)O2)cc1]

4-(4-Hydroxyphenyl)-5-(4-methoxyphenyl)-2,2-dimethylfuran-3(2H)-one (0.1 g, 0.32 mmol) was added to a mixture of cesium carbonate (0.52 g, 1.62 mmol) and DMF (20 mL) at RT under an atmosphere of nitrogen. The reaction mixture was stirred at RT for 30 min upon which 2-(chloromethyl)-3-methylimidazo[1,2-a]pyridine (87 mg, 0.48 mmol) was added. The mixture was heated at for 4 h (the reaction was monitored by TLC). The reaction mixture was diluted with water and extracted with EtOAc, the combined organics were dried over sodium sulfate, filtered and concentrated under reduced pressure. The residue was purified by flash column chromatography using 20% ethyl acetate in n-hexane and silica gel (230-400 mesh) to afford 5-(4-methoxyphenyl)-2, 2-dimethyl-4-(4-((3-methylimidazo[1,2-a]pyridin-2-yl) methoxy)phenyl)furan-3(2H)-one (2.8 g, 77%) as an off-white solid. $^1$H NMR, 500 MHz, DMSO-$d_6$: δ 8.25 (d, 1H), 7.45 (d, 3H), 7.25 (t, 1H), 7.15-6.95 (Ar, 7H), 5.2 (s, 2H), 3.85 (s, 3H), 2.45 (s, 3H), 1.45 (s, 6H). MS: [M+H]+: m/z=455.3. HPLC: (96.3%, Condition-A).

2-(Chloromethyl)-5-methylimidazo[1,2-a]pyridine

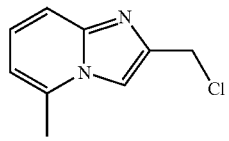

1,3-Dichloroacetone (17.6 g, 138.3 mmol) was added to a solution of 6-methylpyridin-2-amine (10 g, 92.5 mmol) in acetonitrile (200 ml). The mixture was heated at reflux for 14 h (the reaction was monitored by TLC). The mixture was concentrated under reduced pressure, the residue was diluted with water, and the pH was adjusted to 7.5 with sodium bicarbonate solution. The mixture was extracted with EtOAc, the combined organics were dried over sodium sulfate, filtered and concentrated under reduced pressure. The residue was purified by flash column chromatography using 10% ethyl acetate in n-hexane and silica gel (230-400 mesh) to afford 2-(chloromethyl)-5-methylimidazo[1,2-a]pyridine (7.0 g, 70.7%) as a pale yellow solid. $^1$H NMR: 200 MHz, CDCl$_3$: δ 8.15 (s, 1H), 7.6 (dd, 2H), 7.1 (t, 1H), 6.8 (t, 1H), 4.95 (s, 2H), 2.6 (s, 3H). MS: [M+H]+: m/z=181.5.

5-(4-Methoxyphenyl)-2,2-dimethyl-4-(4-((5-methylimidazo[1,2-a]pyridin-2-yl)methoxy)phenyl)furan-3(2H)-one

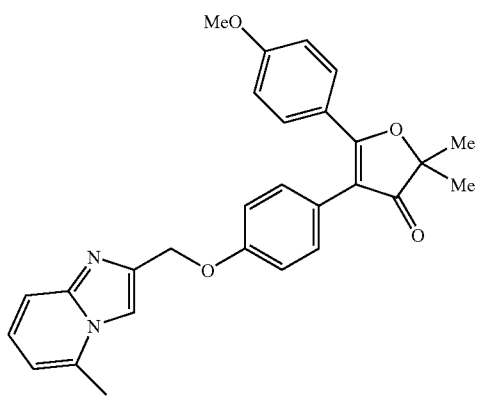 [SMILES: COc1ccc(C2=C(c3ccc(OCc4cn5c(C)cccc5n4)cc3)C(=O)C(C)(C)O2)cc1]

4-(4-Hydroxyphenyl)-5-(4-methoxyphenyl)-2,2-dimethylfuran-3(2H)-one (250 mg, 0.8 mmol) was added to a mixture of cesium carbonate (1.05 g, 3.22 mmol) and DMF (20 mL) at RT under nitrogen. The reaction mixture was stirred at RT for 30 minutes upon which 2-(chloromethyl)-5-methylimidazo[1,2-a]pyridine (218 mg, 1.2 mmol) was added. The mixture was heated at for 4 h (the reaction was monitored by TLC) upon which the reaction mixture was diluted with water and extracted with EtOAc. The combined organics were dried over sodium sulfate, filtered and concentrated under reduced pressure. The residue was purified by flash column chromatography using 15% ethyl acetate in n-hexane and silica gel (230-400 mesh) to afford 5-(4-methoxyphenyl)-2,2-dimethyl-4-(4-((5-methylimidazo[1,2-a]pyridin-2-yl)methoxy)phenyl)furan-3(2H)-one (280 mg, 77.7%) as a light yellow solid. $^1$H NMR: 500 MHz, DMSO-$d_5$: δ 7.95 (s, 1H), 7.6 (d, 2H), 7.4 (d, 1H), 7.25 (t, 1H), 7.2 (d, 3H), 7.15 (d, 2H), 7.0 (d, 2H), 6.8 (d, 1H), 5.2 (s, 2H), 3.85 (s, 3H), 2.6 (s, 3H), 1.25 (s, 6H). MS: [M+H]+: m/z=455.6. HPLC: (97.3%, Condition-A).

5-(4-Methoxyphenyl)-2,2-dimethyl-4-(4-((5-methylimidazo[1,2-a]pyridin-2-yl)methoxy)phenyl)furan-3(2H)-one methanesulfonate

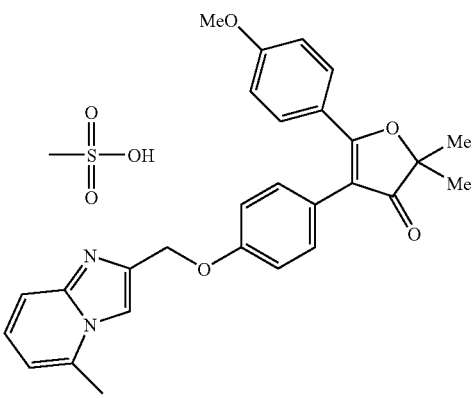

Methanesulfonic acid (53.1 mg, 0.5 mmol) was added to a solution of 544-methoxyphenyl)-2,2-dimethyl-4-(4-((5-methylimidazo[1,2-a]pyridin-2-yl)methoxy)phenyl)furan-3 (2H)-one (250 g, 0.5 mmol) in DCM (2.5 ml) and diethyl ether (50 mL) at RT under an atmosphere of nitrogen. The reaction mixture was stirred at RT for 4 h upon which, the solids were collected by filtration, washed with 20% DCM in diethyl ether, dried in vacuo to afford 5-(4-methoxyphenyl)-2,2-dimethyl-4-(4-((5-methylimidazo[1,2-a]pyridin-2-yl) methoxy)phenyl)furan-3(2H)-one methanesulfonate (240 mg, 82.7%) as white solid: $^1$H NMR: 500 MHz, DMSO-$d_6$: δ 7.95 (s, 1H), 7.6 (d, 2H), 7.4 (d, 1H), 7.25 (t, 1H), 7.2 (d, 3H), 7.15 (d, 2H), 7.0 (d, 2H), 6.8 (d, 1H), 5.2 (s, 2H), 3.85 (s, 3H), 2.6 (s, 3H), 2.5 (s, 3H), 1.25 (s, 6H), HPLC: (98.4%, Condition-A).

6-Chloro-2-(chloromethyl)imidazo[1,2-a]pyridine

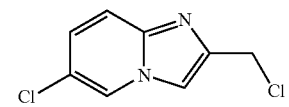 [SMILES: ClCc1cn2cc(Cl)ccc2n1]

1,3-Dichloroacetone (7.4 g, 58.3 mmol) was added to a solution of 5-chloropyridin-2-amine (5.0 g, 38.9 mmol) in acetonitrile (100 ml). The mixture was heated at reflux for 14 h (the reaction was monitored by TLC). Upon completion of the reaction as judged by TLC, the mixture was concentrated under reduced pressure. The residue was diluted with water and the pH was adjusted to 7.5 with sodium bicarbonate solution. The mixture was extracted with EtOAc, the combined organics were dried over sodium sulfate, filtered and concentrated under reduced pressure. The residue was purified by flash column chromatography using 10% ethyl acetate in n-hexane and silica gel (230-400 mesh) to afford 6-chloro-2-(chloromethyl) imidazo[1,2-a]pyridine (1.5 g, 30%) as a pale yellow solid. $^1$H NMR: 200 MHz, CDCl$_3$: δ 8.0 (d, 1H), 7.6 (dd, 2H), 6.8 (d, 1H), 4.75 (s, 2H). MS: [M+H]+: m/z=201.9.

4-(4-((6-Chloroimidazo[1,2-a]pyridin-2-yl)methoxy)phenyl)-5-(4-methoxyphenyl)-2,2-dimethylfuran-3(2H)-one

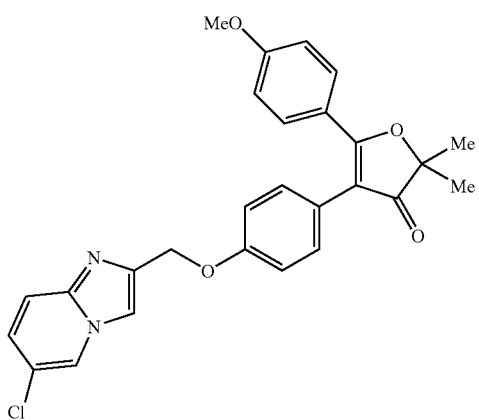 [SMILES: COc1ccc(C2=C(c3ccc(OCc4cn5cc(Cl)ccc5n4)cc3)C(=O)C(C)(C)O2)cc1]

4-(4-Hydroxyphenyl)-5-(4-methoxyphenyl)-2,2-dimethylfuran-3(2H)-one (300 mg, 0.96 mmol) was added to a mixture of cesium carbonate (1.05 g, 3.8 mmol) and DMF (20 mL) at RT under nitrogen. The reaction mixture was stirred at RT for 30 minutes, upon which 6-chloro-2-(chloromethyl) imidazo[1,2-a]pyridine (201 mg, 1.4 mmol) was added. The mixture was heated at 80° C. for 4 h (the reaction was monitored by TLC). Upon completion of the reaction as judged by TLC, the reaction mixture was diluted with water and extracted with EtOAc. The combined organics were dried over sodium sulfate, filtered and concentrated under reduced pressure. The residue was purified by flash column chromatography using 20% ethyl acetate in n-hexane and silica gel (230-400 mesh) to afford 4-(4-((6-chloroimidazo[1,2-a]pyridin-2-yl)methoxy)phenyl)-5-(4-methoxy phenyl)-2,2-dimethylfuran-3(2H)-one (180 mg, 39.3%) as a white solid. $^1$H NMR, 500 MHz, DMSO-d$_6$: δ 8.85 (s, 1H), 8.0 (s, 1H), 7.6 (d, 3H), 7.3 (d, 1H), 7.15 (d, 2H), 7.1 (d, 2H), 7.0 (d, 2H), 5.15 (s, 2H), 3.8 (s, 3H), 1.4 (s, 6H). MS: [M+H]+: m/z=475. HPLC: (98.0%, Condition-A).

4-(4-β6-Chloroimidazo[1,2-a]pyridin-2-yl)methoxy)phenyl)-5-(4-methoxyphenyl)-2,2-dimethylfuran-3(2H)-one methanesulfonate

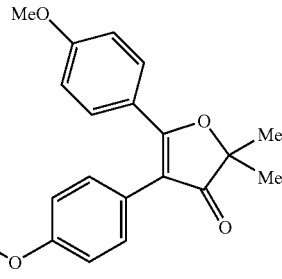

Methanesulfonic acid (53.1 mg, 0.5 mmol) was added to a solution of compound 4-(4-((6-chloroimidazo[1,2-a]pyridin-2-yl)methoxy)phenyl)-5-(4-methoxyphenyl)-2,2-dimethyl-furan-3(2H)-one (250 g, 0.5 mmol) in DCM (2.5 ml) and diethyl ether (50 mL) at RT under an atmosphere of nitrogen. The reaction mixture was stirred at RT for 4 h upon which the solids were collected by filtration, washed with 20% DCM in diethyl ether and dried in vacuo to afford 4-(4-((6-chloroimidazo[1,2-a]pyridin-2-yl)methoxy)phenyl)-5-(4-methoxyphenyl)-2,2-dimethylfuran-3(2H)-one methanesulfonate (240 mg, 82%) as a white solid. $^1$H NMR: 500 MHz, DMSO-d$_6$: δ 8.8 (s, 1H), 8.3 (s, 1H), 8.0 (s, 1H), 7.6 (d, 2H), 7.4 (d, 1H), 7.15 (d, 2H), 7.1 (d, 2H), 7.0 (d, 2H) 5.35 (s, 2H), 3.8 (s, 3H), 2.3 (s, 3H), 1.4 (s, 6H), HPLC: (99.3%, Condition-A).

Tables

In the following tables, if a specific example contains multiple instances of R$_2$, they will be separated by commas in the table (e.g. Me, Me or Et, Me). If the R$_2$ column contains a value "-group-" e.g. "-cyclopropyl-", then both R$_2$ values are taken together to be a spiro ring.

In a further aspect the compounds of the disclosure are embodied in with distinct examples listed in the table below taken from Formula (I):

| Example # | HET | X | Z | R$_2$ |
|---|---|---|---|---|
| 1 | A29 | MeO-phenyl | imidazo[1,2-a]pyridin-2-yl | Me, Me |
| 2 | A29 | NC-phenyl | imidazo[1,2-a]pyridin-2-yl | Me, Me |

-continued

| Example # | HET | X | Z | R₂ |
|---|---|---|---|---|
| 3 | A29 | 4-pyridyl | imidazo[1,2-a]pyridin-2-yl | Me, Me |
| 4 | A29 | 4-MeO-phenyl | 3-F-imidazo[1,2-a]pyridin-2-yl | Me, Me |
| 5 | A29 | 4-NC-phenyl | 3-F-imidazo[1,2-a]pyridin-2-yl | Me, Me |
| 6 | A29 | 4-pyridyl | 3-F-imidazo[1,2-a]pyridin-2-yl | Me, Me |
| 7 | A29 | 4-MeO-phenyl | 3-Cl-imidazo[1,2-a]pyridin-2-yl | Me, Me |
| 8 | A29 | 4-NC-phenyl | 3-Cl-imidazo[1,2-a]pyridin-2-yl | Me, Me |
| 9 | A29 | 4-pyridyl | 3-Cl-imidazo[1,2-a]pyridin-2-yl | Me, Me |
| 10 | A29 | 4-MeO-phenyl | 3-Me-imidazo[1,2-a]pyridin-2-yl | Me, Me |
| 11 | A29 | 4-NC-phenyl | 3-Me-imidazo[1,2-a]pyridin-2-yl | Me, Me |
| 12 | A29 | 4-pyridyl | 3-Me-imidazo[1,2-a]pyridin-2-yl | Me, Me |

-continued

| Example # | HET | X | Z | R₂ |
|---|---|---|---|---|
| 13 | A29 | MeO-C₆H₄- | imidazo[1,2-a]pyridin-2-yl, 3-OH | Me, Me |
| 14 | A29 | NC-C₆H₄- | imidazo[1,2-a]pyridin-2-yl, 3-OH | Me, Me |
| 15 | A29 | pyridin-4-yl | imidazo[1,2-a]pyridin-2-yl, 3-OH | Me, Me |
| 16 | A29 | MeO-C₆H₄- | imidazo[1,2-a]pyridin-2-yl, 3-OMe | Me, Me |
| 17 | A29 | NC-C₆H₄- | imidazo[1,2-a]pyridin-2-yl, 3-OMe | Me, Me |
| 18 | A29 | pyridin-4-yl | imidazo[1,2-a]pyridin-2-yl, 3-OMe | Me, Me |
| 19 | A29 | MeO-C₆H₄- | imidazo[1,2-a]pyridin-2-yl, 3-OCF₃ | Me, Me |
| 20 | A29 | NC-C₆H₄- | imidazo[1,2-a]pyridin-2-yl, 3-OCF₃ | Me, Me |
| 21 | A29 | pyridin-4-yl | imidazo[1,2-a]pyridin-2-yl, 3-OCF₃ | Me, Me |
| 22 | A29 | MeO-C₆H₄- | imidazo[1,2-a]pyridin-2-yl, 3-CN | Me, Me |

-continued

| Example # | HET | X | Z | R₂ |
|---|---|---|---|---|
| 23 | A29 | 4-cyanophenyl | 2-methyl-imidazo[1,2-a]pyridin-3-yl, 3-CN | Me, Me |
| 24 | A29 | pyridin-4-yl | 2-methyl-imidazo[1,2-a]pyridin-3-yl, 3-CN | Me, Me |
| 25 | A29 | 4-methoxyphenyl | 5-fluoro-imidazo[1,2-a]pyridin-2-yl | Me, Me |
| 26 | A29 | 4-cyanophenyl | 5-fluoro-imidazo[1,2-a]pyridin-2-yl | Me, Me |
| 27 | A29 | pyridin-4-yl | 5-fluoro-imidazo[1,2-a]pyridin-2-yl | Me, Me |
| 28 | A29 | 4-methoxyphenyl | 5-chloro-imidazo[1,2-a]pyridin-2-yl | Me, Me |
| 29 | A29 | 4-cyanophenyl | 5-chloro-imidazo[1,2-a]pyridin-2-yl | Me, Me |
| 30 | A29 | pyridin-4-yl | 5-chloro-imidazo[1,2-a]pyridin-2-yl | Me, Me |
| 31 | A29 | 4-methoxyphenyl | 5-methyl-imidazo[1,2-a]pyridin-2-yl | Me, Me |
| 32 | A29 | 4-cyanophenyl | 5-methyl-imidazo[1,2-a]pyridin-2-yl | Me, Me |

-continued

| Example # | HET | X | Z | R₂ |
|---|---|---|---|---|
| 33 | A29 | 4-pyridyl | 5-methyl-imidazo[1,2-a]pyridin-2-yl | Me, Me |
| 34 | A29 | 4-MeO-phenyl | 5-hydroxy-imidazo[1,2-a]pyridin-2-yl | Me, Me |
| 35 | A29 | 4-NC-phenyl | 5-hydroxy-imidazo[1,2-a]pyridin-2-yl | Me, Me |
| 36 | A29 | 4-pyridyl | 5-hydroxy-imidazo[1,2-a]pyridin-2-yl | Me, Me |
| 37 | A29 | 4-MeO-phenyl | 5-methoxy-imidazo[1,2-a]pyridin-2-yl | Me, Me |
| 38 | A29 | 4-NC-phenyl | 5-methoxy-imidazo[1,2-a]pyridin-2-yl | Me, Me |
| 39 | A29 | 4-pyridyl | 5-methoxy-imidazo[1,2-a]pyridin-2-yl | Me, Me |
| 40 | A29 | 4-MeO-phenyl | 5-OCF₃-imidazo[1,2-a]pyridin-2-yl | Me, Me |
| 41 | A29 | 4-NC-phenyl | 5-OCF₃-imidazo[1,2-a]pyridin-2-yl | Me, Me |
| 42 | A29 | 4-pyridyl | 5-OCF₃-imidazo[1,2-a]pyridin-2-yl | Me, Me |

-continued

| Example # | HET | X | Z | R₂ |
|---|---|---|---|---|
| 43 | A29 | MeO-phenyl | imidazo[1,2-a]pyridine-CN | Me, Me |
| 44 | A29 | NC-phenyl | imidazo[1,2-a]pyridine-CN | Me, Me |
| 45 | A29 | pyridyl | imidazo[1,2-a]pyridine-CN | Me, Me |
| 46 | A29 | MeO-phenyl | F-imidazo[1,2-a]pyridine | Me, Me |
| 47 | A29 | NC-phenyl | F-imidazo[1,2-a]pyridine | Me, Me |
| 48 | A29 | pyridyl | F-imidazo[1,2-a]pyridine | Me, Me |
| 49 | A29 | MeO-phenyl | Cl-imidazo[1,2-a]pyridine | Me, Me |
| 50 | A29 | NC-phenyl | Cl-imidazo[1,2-a]pyridine | Me, Me |
| 51 | A29 | pyridyl | Cl-imidazo[1,2-a]pyridine | Me, Me |
| 52 | A29 | MeO-phenyl | Me-imidazo[1,2-a]pyridine | Me, Me |

-continued
| Example # | HET | X | Z | R₂ |
|---|---|---|---|---|
| 53 | A29 | 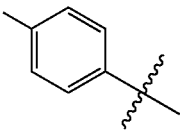 | 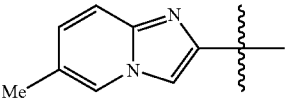 | Me, Me |
| 54 | A29 | 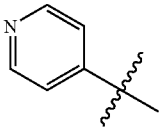 [SMILES: *c1ccncc1] | 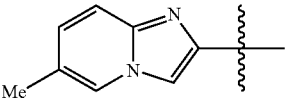 | Me, Me |
| 55 | A29 | 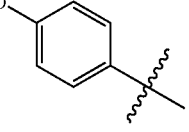 | 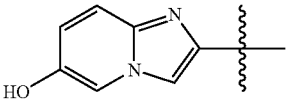 | Me, Me |
| 56 | A29 | 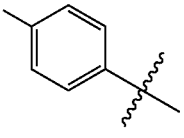 | 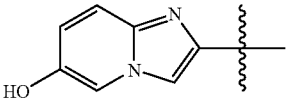 | Me, Me |
| 57 | A29 | 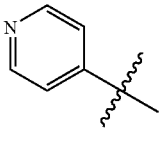 [SMILES: *c1ccncc1] | 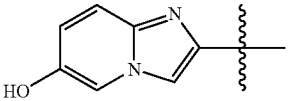 | Me, Me |
| 58 | A29 | 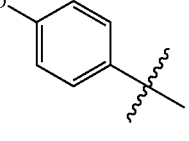 | 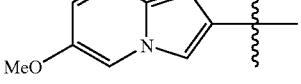 | Me, Me |
| 59 | A29 | 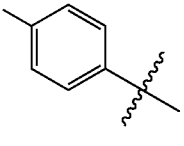 | 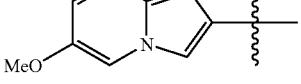 | Me, Me |
| 60 | A29 | 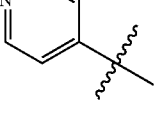 | 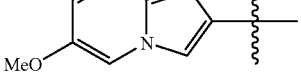 | Me, Me |
| 61 | A29 | 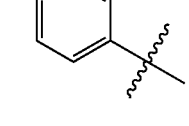 | 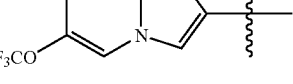 | Me, Me |
| 62 | A29 | 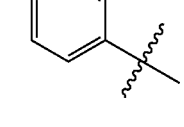 | 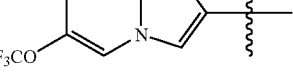 | Me, Me |

-continued

| Example # | HET | X | Z | R₂ |
|---|---|---|---|---|
| 63 | A29 | 4-pyridyl | 6-(trifluoromethoxy)imidazo[1,2-a]pyridin-2-yl | Me, Me |
| 64 | A29 | 4-methoxyphenyl | 6-cyanoimidazo[1,2-a]pyridin-2-yl | Me, Me |
| 65 | A29 | 4-cyanophenyl | 6-cyanoimidazo[1,2-a]pyridin-2-yl | Me, Me |
| 66 | A29 | 4-pyridyl | 6-cyanoimidazo[1,2-a]pyridin-2-yl | Me, Me |
| 67 | A29 | 4-methoxyphenyl | 7-fluoroimidazo[1,2-a]pyridin-2-yl | Me, Me |
| 68 | A29 | 4-cyanophenyl | 7-fluoroimidazo[1,2-a]pyridin-2-yl | Me, Me |
| 69 | A29 | 4-pyridyl | 7-fluoroimidazo[1,2-a]pyridin-2-yl | Me, Me |
| 70 | A29 | 4-methoxyphenyl | 7-chloroimidazo[1,2-a]pyridin-2-yl | Me, Me |
| 71 | A29 | 4-cyanophenyl | 7-chloroimidazo[1,2-a]pyridin-2-yl | Me, Me |
| 72 | A29 | 4-pyridyl | 7-chloroimidazo[1,2-a]pyridin-2-yl | Me, Me |

-continued

| Example # | HET | X | Z | R₂ |
|---|---|---|---|---|
| 73 | A29 | MeO-C₆H₄- | 7-Me-imidazo[1,2-a]pyridin-2-yl | Me, Me |
| 74 | A29 | NC-C₆H₄- | 7-Me-imidazo[1,2-a]pyridin-2-yl | Me, Me |
| 75 | A29 | pyridin-4-yl | 7-Me-imidazo[1,2-a]pyridin-2-yl | Me, Me |
| 76 | A29 | MeO-C₆H₄- | 7-HO-imidazo[1,2-a]pyridin-2-yl | Me, Me |
| 77 | A29 | NC-C₆H₄- | 7-HO-imidazo[1,2-a]pyridin-2-yl | Me, Me |
| 78 | A29 | pyridin-4-yl | 7-HO-imidazo[1,2-a]pyridin-2-yl | Me, Me |
| 79 | A29 | MeO-C₆H₄- | 7-MeO-imidazo[1,2-a]pyridin-2-yl | Me, Me |
| 80 | A29 | NC-C₆H₄- | 7-MeO-imidazo[1,2-a]pyridin-2-yl | Me, Me |
| 81 | A29 | pyridin-4-yl | 7-MeO-imidazo[1,2-a]pyridin-2-yl | Me, Me |
| 82 | A29 | MeO-C₆H₄- | 7-F₃CO-imidazo[1,2-a]pyridin-2-yl | Me, Me |

-continued

| Example # | HET | X | Z | R₂ |
|---|---|---|---|---|
| 83 | A29 | 4-NC-phenyl | 7-(F₃CO)-imidazo[1,2-a]pyridin-2-yl | Me, Me |
| 84 | A29 | pyridin-4-yl | 7-(F₃CO)-imidazo[1,2-a]pyridin-2-yl | Me, Me |
| 85 | A29 | 4-MeO-phenyl | 7-NC-imidazo[1,2-a]pyridin-2-yl | Me, Me |
| 86 | A29 | 4-NC-phenyl | 7-NC-imidazo[1,2-a]pyridin-2-yl | Me, Me |
| 87 | A29 | pyridin-4-yl | 7-NC-imidazo[1,2-a]pyridin-2-yl | Me, Me |
| 88 | A29 | 4-MeO-phenyl | imidazo[1,2-b]pyridazin-6-yl | Me, Me |
| 89 | A29 | 4-NC-phenyl | imidazo[1,2-b]pyridazin-6-yl | Me, Me |
| 90 | A29 | pyridin-4-yl | imidazo[1,2-b]pyridazin-6-yl | Me, Me |
| 91 | A29 | 4-MeO-phenyl | 3-F-imidazo[1,2-b]pyridazin-6-yl | Me, Me |
| 92 | A29 | 4-NC-phenyl | 3-F-imidazo[1,2-b]pyridazin-6-yl | Me, Me |

-continued

| Example # | HET | X | Z | R₂ |
|---|---|---|---|---|
| 93 | A29 | 4-pyridyl | 3-fluoroimidazo[1,2-b]pyridazin-6-yl | Me, Me |
| 94 | A29 | 4-methoxyphenyl | 3-chloroimidazo[1,2-b]pyridazin-6-yl | Me, Me |
| 95 | A29 | 4-cyanophenyl | 3-chloroimidazo[1,2-b]pyridazin-6-yl | Me, Me |
| 96 | A29 | 4-pyridyl | 3-chloroimidazo[1,2-b]pyridazin-6-yl | Me, Me |
| 97 | A29 | 4-methoxyphenyl | 3-methylimidazo[1,2-b]pyridazin-6-yl | Me, Me |
| 98 | A29 | 4-cyanophenyl | 3-methylimidazo[1,2-b]pyridazin-6-yl | Me, Me |
| 99 | A29 | 4-pyridyl | 3-methylimidazo[1,2-b]pyridazin-6-yl | Me, Me |
| 100 | A29 | 4-methoxyphenyl | 3-methylimidazo[1,2-b]pyridazin-6-yl | Me, Me |
| 101 | A29 | 4-cyanophenyl | 3-hydroxyimidazo[1,2-b]pyridazin-6-yl | Me, Me |
| 102 | A29 | 4-pyridyl | 3-hydroxyimidazo[1,2-b]pyridazin-6-yl | Me, Me |

-continued
| Example # | HET | X | Z | R$_2$ |
|---|---|---|---|---|
| 103 | A29 | 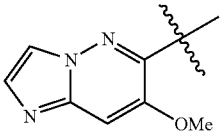 | 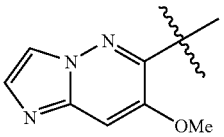 | Me, Me |
| 104 | A29 | 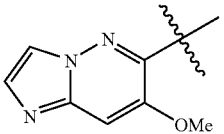 [SMILES: *c1nn2ccnc2cc1OC] | 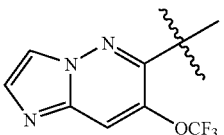 | Me, Me |
| 105 | A29 | 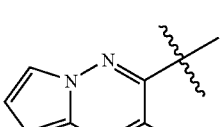 | 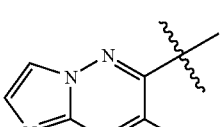 | Me, Me |
| 106 | A29 | 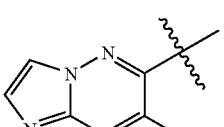 | 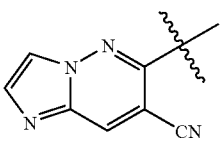 | Me, Me |
| 107 | A29 | 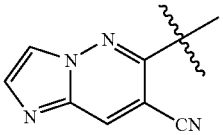 [SMILES: *c1nn2ccnc2cc1C#N] | 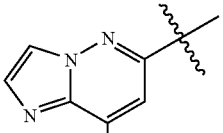 | Me, Me |
| 108 | A29 | | | Me, Me |
| 109 | A29 | | | Me, Me |
| 110 | A29 | | | Me, Me |
| 111 | A29 | | | Me, Me |
| 121 | A29 | | | Me, Me |

-continued

| Example # | HET | X | Z | R₂ |
|---|---|---|---|---|
| 122 | A29 | 4-cyanophenyl | 8-fluoroimidazo[1,2-b]pyridazin-6-yl | Me, Me |
| 123 | A29 | pyridin-4-yl | 8-fluoroimidazo[1,2-b]pyridazin-6-yl | Me, Me |
| 124 | A29 | 4-methoxyphenyl | 8-chloroimidazo[1,2-b]pyridazin-6-yl | Me, Me |
| 125 | A29 | 4-cyanophenyl | 8-chloroimidazo[1,2-b]pyridazin-6-yl | Me, Me |
| 126 | A29 | pyridin-4-yl | 8-chloroimidazo[1,2-b]pyridazin-6-yl | Me, Me |
| 127 | A29 | 4-methoxyphenyl | 8-methylimidazo[1,2-b]pyridazin-6-yl | Me, Me |
| 128 | A29 | 4-cyanophenyl | 8-methylimidazo[1,2-b]pyridazin-6-yl | Me, Me |
| 129 | A29 | pyridin-4-yl | 8-methylimidazo[1,2-b]pyridazin-6-yl | Me, Me |

-continued

| Example # | HET | X | Z | R$_2$ |
|---|---|---|---|---|
| 130 | A29 | 4-MeO-phenyl | imidazo[1,2-b]pyridazine, 8-OH | Me, Me |
| 131 | A29 | 4-NC-phenyl | imidazo[1,2-b]pyridazine, 8-OH | Me, Me |
| 132 | A29 | pyridin-4-yl | imidazo[1,2-b]pyridazine, 8-OH | Me, Me |
| 133 | A29 | 4-MeO-phenyl | imidazo[1,2-b]pyridazine, 8-OMe | Me, Me |
| 134 | A29 | 4-NC-phenyl | imidazo[1,2-b]pyridazine, 8-OMe | Me, Me |
| 135 | A29 | pyridin-4-yl | imidazo[1,2-b]pyridazine, 8-OMe | Me, Me |
| 136 | A29 | 4-MeO-phenyl | imidazo[1,2-b]pyridazine, 8-OCF$_3$ | Me, Me |
| 137 | A29 | 4-NC-phenyl | imidazo[1,2-b]pyridazine, 8-OCF$_3$ | Me, Me |

-continued

| Example # | HET | X | Z | R₂ |
|---|---|---|---|---|
| 138 | A29 | 4-pyridyl | imidazo[1,2-b]pyridazin-6-yl, 8-OCF₃ | Me, Me |
| 139 | A29 | 4-MeO-phenyl | imidazo[1,2-b]pyridazin-6-yl, 8-CN | Me, Me |
| 140 | A29 | 4-NC-phenyl | imidazo[1,2-b]pyridazin-6-yl, 8-CN | Me, Me |
| 141 | A29 | 4-pyridyl | imidazo[1,2-b]pyridazin-6-yl, 8-CN | Me, Me |
| 142 | A29 | 4-MeO-phenyl | 2-F-imidazo[1,2-b]pyridazin-6-yl | Me, Me |
| 143 | A29 | 4-NC-phenyl | 2-F-imidazo[1,2-b]pyridazin-6-yl | Me, Me |
| 144 | A29 | 4-pyridyl | 2-F-imidazo[1,2-b]pyridazin-6-yl | Me, Me |
| 145 | A29 | 4-MeO-phenyl | 2-Cl-imidazo[1,2-b]pyridazin-6-yl | Me, Me |
| 146 | A29 | 4-NC-phenyl | 2-Cl-imidazo[1,2-b]pyridazin-6-yl | Me, Me |

-continued

| Example # | HET | X | Z | R₂ |
|---|---|---|---|---|
| 147 | A29 | 4-pyridyl | 2-chloro-imidazo[1,2-b]pyridazin-6-yl | Me, Me |
| 148 | A29 | 4-MeO-phenyl | 2-methyl-imidazo[1,2-b]pyridazin-6-yl | Me, Me |
| 149 | A29 | 4-NC-phenyl | 2-methyl-imidazo[1,2-b]pyridazin-6-yl | Me, Me |
| 150 | A29 | 4-pyridyl | 2-methyl-imidazo[1,2-b]pyridazin-6-yl | Me, Me |
| 151 | A29 | 4-MeO-phenyl | 2-hydroxy-imidazo[1,2-b]pyridazin-6-yl | Me, Me |
| 152 | A29 | 4-NC-phenyl | 2-hydroxy-imidazo[1,2-b]pyridazin-6-yl | Me, Me |
| 153 | A29 | 4-pyridyl | 2-hydroxy-imidazo[1,2-b]pyridazin-6-yl | Me, Me |
| 154 | A29 | 4-MeO-phenyl | 2-methoxy-imidazo[1,2-b]pyridazin-6-yl | Me, Me |
| 155 | A29 | 4-NC-phenyl | 2-methoxy-imidazo[1,2-b]pyridazin-6-yl | Me, Me |
| 156 | A29 | 4-pyridyl | 2-methoxy-imidazo[1,2-b]pyridazin-6-yl | Me, Me |

-continued
| Example # | HET | X | Z | R₂ |
|---|---|---|---|---|
| 157 | A29 | 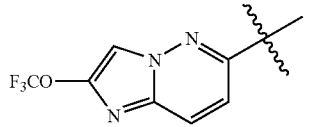 [SMILES: *c1ccc2nc(OC(F)(F)F)cn2n1] | 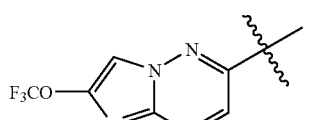 | Me, Me |
| 158 | A29 | 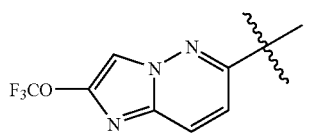 [SMILES: *c1ccc2nc(OC(F)(F)F)cn2n1] | 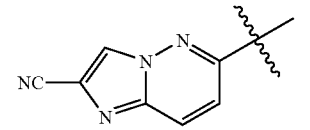 | Me, Me |
| 159 | A29 | 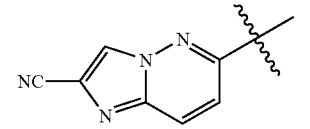 | 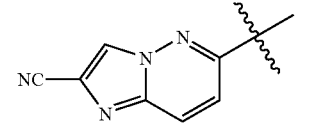 | Me, Me |
| 160 | A29 | 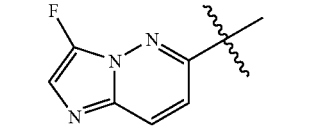 [SMILES: *c1ccc2ncc(F)n2n1] | 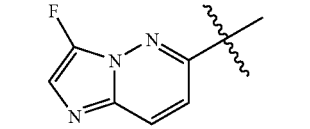 [SMILES: *c1ccc2ncc(F)n2n1] | Me, Me |
| 161 | A29 | 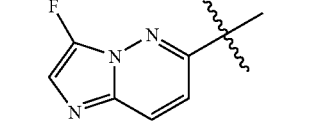 | 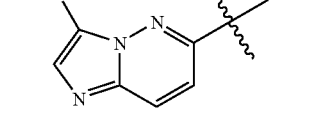 | Me, Me |
| 162 | A29 | (4-pyridyl) | 2-cyano-imidazo[1,2-b]pyridazin-6-yl | Me, Me |
| 163 | A29 | 4-MeO-phenyl | 3-fluoro-imidazo[1,2-b]pyridazin-6-yl | Me, Me |
| 164 | A29 | 4-NC-phenyl | 3-fluoro-imidazo[1,2-b]pyridazin-6-yl | Me, Me |
| 165 | A29 | (4-pyridyl) | 3-fluoro-imidazo[1,2-b]pyridazin-6-yl | Me, Me |
| 166 | A29 | 4-MeO-phenyl | 3-chloro-imidazo[1,2-b]pyridazin-6-yl | Me, Me |

-continued

| Example # | HET | X | Z | R₂ |
|---|---|---|---|---|
| 167 | A29 | 4-cyanophenyl | 3-chloroimidazo[1,2-b]pyridazin-6-yl | Me, Me |
| 168 | A29 | pyridin-4-yl | 3-chloroimidazo[1,2-b]pyridazin-6-yl | Me, Me |
| 169 | A29 | 4-methoxyphenyl | 3-methylimidazo[1,2-b]pyridazin-6-yl | Me, Me |
| 170 | A29 | 4-cyanophenyl | 3-methylimidazo[1,2-b]pyridazin-6-yl | Me, Me |
| 171 | A29 | pyridin-4-yl | 3-methylimidazo[1,2-b]pyridazin-6-yl | Me, Me |
| 172 | A29 | 4-methoxyphenyl | 3-hydroxyimidazo[1,2-b]pyridazin-6-yl | Me, Me |
| 173 | A29 | 4-cyanophenyl | 3-hydroxyimidazo[1,2-b]pyridazin-6-yl | Me, Me |
| 174 | A29 | pyridin-4-yl | 3-hydroxyimidazo[1,2-b]pyridazin-6-yl | Me, Me |
| 175 | A29 | 4-methoxyphenyl | 3-methoxyimidazo[1,2-b]pyridazin-6-yl | Me, Me |
| 176 | A29 | 4-cyanophenyl | 3-methoxyimidazo[1,2-b]pyridazin-6-yl | Me, Me |

-continued
| Example # | HET | X | Z | R₂ |
|---|---|---|---|---|
| 177 | A29 | 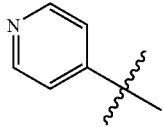 [SMILES: *c1ccncc1] | 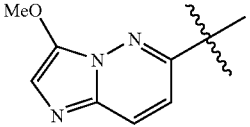 [SMILES: *c1ccc2ncc(OC)n2n1] | Me, Me |
| 178 | A29 | 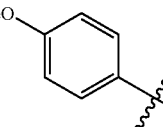 | 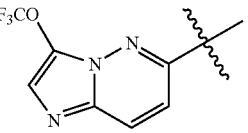 [SMILES: *c1ccc2ncc(OC)n2n1] | Me, Me |
| 179 | A29 | 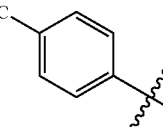 | 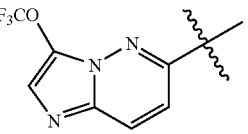 [SMILES: *c1ccc2ncc(OC)n2n1] | Me, Me |
| 180 | A29 | 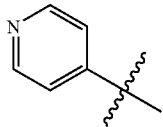 [SMILES: *c1ccncc1] | 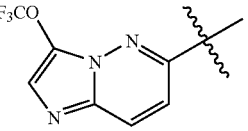 | Me, Me |
| 181 | A29 | 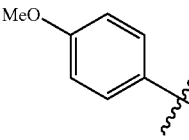 | 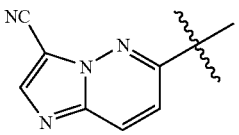 | Me, Me |
| 182 | A29 | 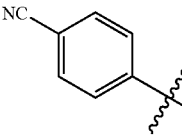 | 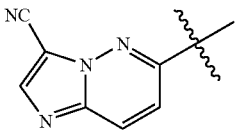 | Me, Me |
| 183 | A29 | 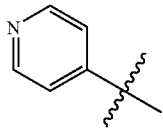 | 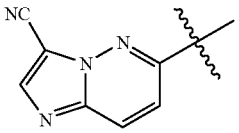 | Me, Me |
| 184 | A29 | 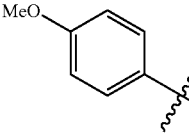 | 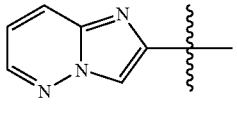 [SMILES: *c1cn2ncccc2n1] | Me, Me |
| 185 | A29 | 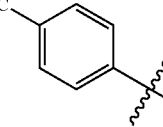 | 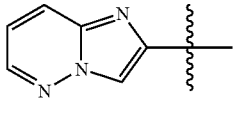 [SMILES: *c1cn2ncccc2n1] | Me, Me |
| 186 | A29 | 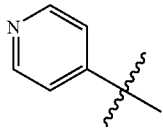 | 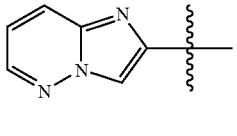 [SMILES: *c1cn2ncccc2n1] | Me, Me |

| Example # | HET | X | Z | R₂ |
|---|---|---|---|---|
| 187 | A29 | 4-MeO-phenyl | 3-F-imidazo[1,2-b]pyridazin-2-yl | Me, Me |
| 188 | A29 | 4-NC-phenyl | 3-F-imidazo[1,2-b]pyridazin-2-yl | Me, Me |
| 189 | A29 | pyridin-4-yl | 3-F-imidazo[1,2-b]pyridazin-2-yl | Me, Me |
| 190 | A29 | 4-MeO-phenyl | 3-Cl-imidazo[1,2-b]pyridazin-2-yl | Me, Me |
| 191 | A29 | 4-NC-phenyl | 3-Cl-imidazo[1,2-b]pyridazin-2-yl | Me, Me |
| 192 | A29 | pyridin-4-yl | 3-Cl-imidazo[1,2-b]pyridazin-2-yl | Me, Me |
| 193 | A29 | 4-MeO-phenyl | 3-Me-imidazo[1,2-b]pyridazin-2-yl | Me, Me |
| 194 | A29 | 4-NC-phenyl | 3-Me-imidazo[1,2-b]pyridazin-2-yl | Me, Me |
| 195 | A29 | pyridin-4-yl | 3-Me-imidazo[1,2-b]pyridazin-2-yl | Me, Me |
| 196 | A29 | 4-MeO-phenyl | 3-OH-imidazo[1,2-b]pyridazin-2-yl | Me, Me |

-continued

| Example # | HET | X | Z | R₂ |
|---|---|---|---|---|
| 197 | A29 | 4-cyanophenyl | imidazo[1,2-b]pyridazin-2-yl, 3-OH | Me, Me |
| 198 | A29 | pyridin-4-yl | imidazo[1,2-b]pyridazin-2-yl, 3-OH | Me, Me |
| 199 | A29 | 4-methoxyphenyl | imidazo[1,2-b]pyridazin-2-yl, 3-OMe | Me, Me |
| 200 | A29 | 4-cyanophenyl | imidazo[1,2-b]pyridazin-2-yl, 3-OMe | Me, Me |
| 201 | A29 | pyridin-4-yl | imidazo[1,2-b]pyridazin-2-yl, 3-OMe | Me, Me |
| 202 | A29 | 4-methoxyphenyl | imidazo[1,2-b]pyridazin-2-yl, 3-OCF₃ | Me, Me |
| 203 | A29 | 4-cyanophenyl | imidazo[1,2-b]pyridazin-2-yl, 3-OCF₃ | Me, Me |
| 204 | A29 | pyridin-4-yl | imidazo[1,2-b]pyridazin-2-yl, 3-OCF₃ | Me, Me |
| 205 | A29 | 4-methoxyphenyl | imidazo[1,2-b]pyridazin-2-yl, 3-CN | Me, Me |
| 206 | A29 | 4-cyanophenyl | imidazo[1,2-b]pyridazin-2-yl, 3-CN | Me, Me |

-continued
| Example # | HET | X | Z | R₂ |
|---|---|---|---|---|
| 207 | A29 | 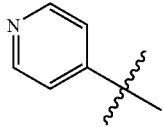 [SMILES: *c1ccncc1] | 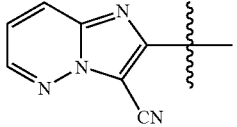 | Me, Me |
| 211 | A29 | 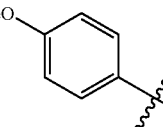 | 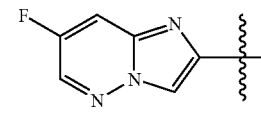 | Me, Me |
| 212 | A29 | 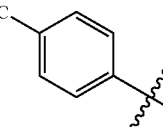 | 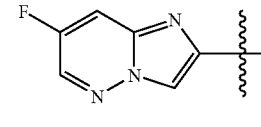 | Me, Me |
| 213 | A29 | 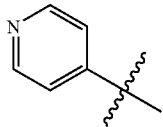 [SMILES: *c1ccncc1] | 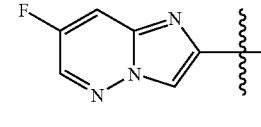 | Me, Me |
| 214 | A29 | 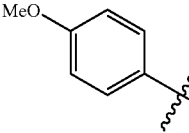 | 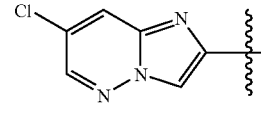 | Me, Me |
| 215 | A29 | 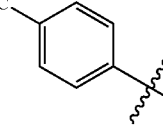 | 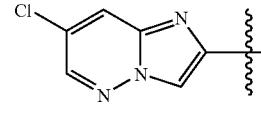 | Me, Me |
| 216 | A29 | 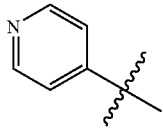 [SMILES: *c1ccncc1] | 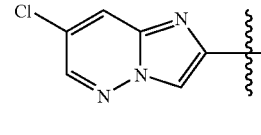 | Me, Me |
| 217 | A29 | 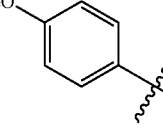 | 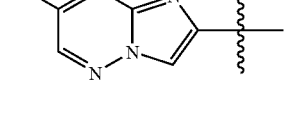 | Me, Me |
| 218 | A29 | 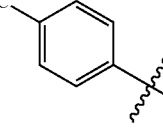 | 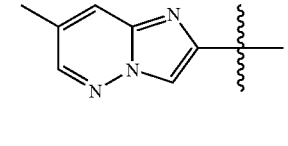 [SMILES: *c1cn2ncc(C)cc2n1] | Me, Me |
| 219 | A29 | 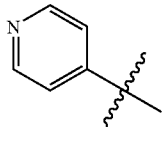 | 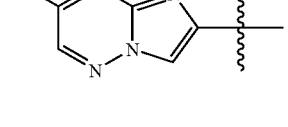 | Me, Me |

-continued

| Example # | HET | X | Z | R₂ |
|---|---|---|---|---|
| 220 | A29 | MeO-phenyl | 7-HO-imidazo[1,2-b]pyridazin-2-yl | Me, Me |
| 221 | A29 | NC-phenyl | 7-HO-imidazo[1,2-b]pyridazin-2-yl | Me, Me |
| 222 | A29 | pyridin-4-yl | 7-HO-imidazo[1,2-b]pyridazin-2-yl | Me, Me |
| 223 | A29 | MeO-phenyl | 7-MeO-imidazo[1,2-b]pyridazin-2-yl | Me, Me |
| 224 | A29 | NC-phenyl | 7-MeO-imidazo[1,2-b]pyridazin-2-yl | Me, Me |
| 225 | A29 | pyridin-4-yl | 7-MeO-imidazo[1,2-b]pyridazin-2-yl | Me, Me |
| 226 | A29 | MeO-phenyl | 7-F₃CO-imidazo[1,2-b]pyridazin-2-yl | Me, Me |
| 227 | A29 | NC-phenyl | 7-F₃CO-imidazo[1,2-b]pyridazin-2-yl | Me, Me |
| 228 | A29 | pyridin-4-yl | 7-F₃CO-imidazo[1,2-b]pyridazin-2-yl | Me, Me |
| 229 | A29 | MeO-phenyl | 7-NC-imidazo[1,2-b]pyridazin-2-yl | Me, Me |

-continued
| Example # | HET | X | Z | R₂ |
|---|---|---|---|---|
| 230 | A29 | 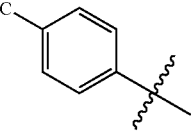 | 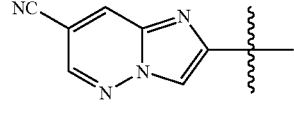 | Me, Me |
| 231 | A29 | 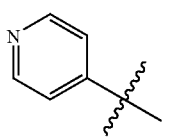 [SMILES: *c1ccncc1] | 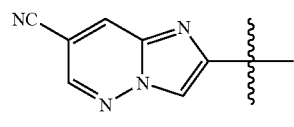 | Me, Me |
| 232 | A29 | 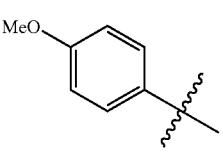 | 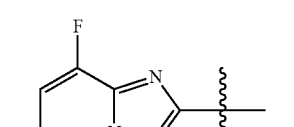 | Me, Me |
| 233 | A29 | 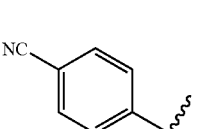 | 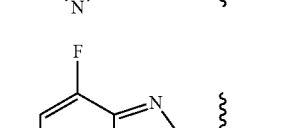 | Me, Me |
| 234 | A29 | 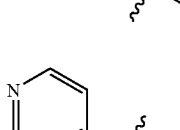 | 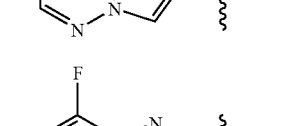 | Me, Me |
| 235 | A29 | 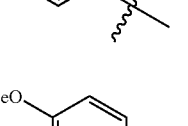 | 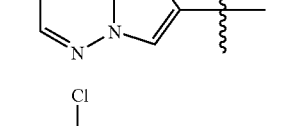 | Me, Me |
| 236 | A29 | 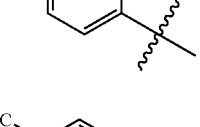 | 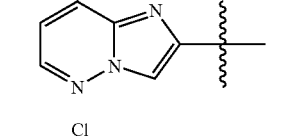 | Me, Me |
| 237 | A29 | 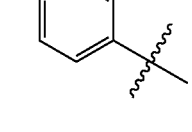 | 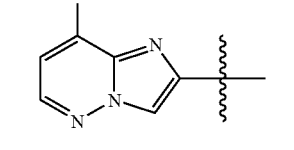 | Me, Me |
| 238 | A29 | 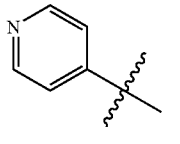 | 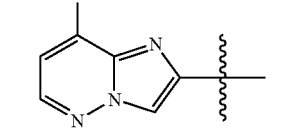 | Me, Me |
| 239 | A29 | 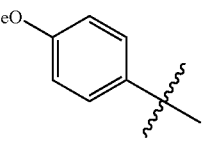 | 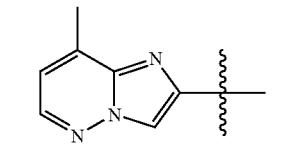 [SMILES: *c1cn2nccc(C)c2n1] | Me, Me |

-continued

| Example # | HET | X | Z | R₂ |
|---|---|---|---|---|
| 240 | A29 | 4-pyridyl | 8-methyl-imidazo[1,2-b]pyridazin-2-yl | Me, Me |
| 241 | A29 | 4-MeO-phenyl | 8-OH-imidazo[1,2-b]pyridazin-2-yl | Me, Me |
| 242 | A29 | 4-NC-phenyl | 8-OH-imidazo[1,2-b]pyridazin-2-yl | Me, Me |
| 243 | A29 | 4-pyridyl | 8-OH-imidazo[1,2-b]pyridazin-2-yl | Me, Me |
| 244 | A29 | 4-MeO-phenyl | 8-OMe-imidazo[1,2-b]pyridazin-2-yl | Me, Me |
| 245 | A29 | 4-NC-phenyl | 8-OMe-imidazo[1,2-b]pyridazin-2-yl | Me, Me |
| 246 | A29 | 4-pyridyl | 8-OMe-imidazo[1,2-b]pyridazin-2-yl | Me, Me |
| 247 | A29 | 4-MeO-phenyl | 8-OCF₃-imidazo[1,2-b]pyridazin-2-yl | Me, Me |
| 248 | A29 | 4-NC-phenyl | 8-OCF₃-imidazo[1,2-b]pyridazin-2-yl | Me, Me |

-continued

| Example # | HET | X | Z | R₂ |
|---|---|---|---|---|
| 249 | A29 | 4-pyridyl | 8-OCF₃-imidazo[1,2-b]pyridazin-2-yl | Me, Me |
| 250 | A29 | 4-MeO-phenyl | 8-CN-imidazo[1,2-b]pyridazin-2-yl | Me, Me |
| 251 | A29 | 4-NC-phenyl | 8-CN-imidazo[1,2-b]pyridazin-2-yl | Me, Me |
| 252 | A29 | 4-pyridyl | 8-CN-imidazo[1,2-b]pyridazin-2-yl | Me, Me |
| 253 | A31 | 4-MeO-phenyl | imidazo[1,2-a]pyridin-2-yl | Me, Me |
| 254 | A31 | 4-NC-phenyl | imidazo[1,2-a]pyridin-2-yl | Me, Me |
| 255 | A31 | 4-pyridyl | imidazo[1,2-a]pyridin-2-yl | Me, Me |
| 256 | A31 | 4-MeO-phenyl | 3-F-imidazo[1,2-a]pyridin-2-yl | Me, Me |
| 257 | A31 | 4-NC-phenyl | 3-F-imidazo[1,2-a]pyridin-2-yl | Me, Me |
| 258 | A31 | 4-pyridyl | 3-F-imidazo[1,2-a]pyridin-2-yl | Me, Me |

-continued

| Example # | HET | X | Z | R₂ |
|---|---|---|---|---|
| 259 | A31 | MeO-C₆H₄- | imidazo[1,2-a]pyridine-2-yl, 3-Cl | Me, Me |
| 260 | A31 | NC-C₆H₄- | imidazo[1,2-a]pyridine-2-yl, 3-Cl | Me, Me |
| 261 | A31 | 4-pyridyl | imidazo[1,2-a]pyridine-2-yl, 3-Cl | Me, Me |
| 262 | A31 | MeO-C₆H₄- | imidazo[1,2-a]pyridine-2-yl, 3-Me | Me, Me |
| 263 | A31 | NC-C₆H₄- | imidazo[1,2-a]pyridine-2-yl, 3-Me | Me, Me |
| 264 | A31 | 4-pyridyl | imidazo[1,2-a]pyridine-2-yl, 3-Me | Me, Me |
| 265 | A31 | MeO-C₆H₄- | imidazo[1,2-a]pyridine-2-yl, 3-OH | Me, Me |
| 266 | A31 | NC-C₆H₄- | imidazo[1,2-a]pyridine-2-yl, 3-OH | Me, Me |
| 267 | A31 | 4-pyridyl | imidazo[1,2-a]pyridine-2-yl, 3-OH | Me, Me |
| 268 | A31 | MeO-C₆H₄- | imidazo[1,2-a]pyridine-2-yl, 3-OMe | Me, Me |

-continued

| Example # | HET | X | Z | R₂ |
|---|---|---|---|---|
| 269 | A31 | 4-CN-phenyl | imidazo[1,2-a]pyridin-2-yl, 3-OMe | Me, Me |
| 270 | A31 | pyridin-4-yl | imidazo[1,2-a]pyridin-2-yl, 3-OMe | Me, Me |
| 271 | A31 | 4-MeO-phenyl | imidazo[1,2-a]pyridin-2-yl, 3-OCF₃ | Me, Me |
| 272 | A31 | 4-CN-phenyl | imidazo[1,2-a]pyridin-2-yl, 3-OCF₃ | Me, Me |
| 273 | A31 | pyridin-4-yl | imidazo[1,2-a]pyridin-2-yl, 3-OCF₃ | Me, Me |
| 274 | A31 | 4-MeO-phenyl | imidazo[1,2-a]pyridin-2-yl, 3-CN | Me, Me |
| 275 | A31 | 4-CN-phenyl | imidazo[1,2-a]pyridin-2-yl, 3-CN | Me, Me |
| 276 | A31 | pyridin-4-yl | imidazo[1,2-a]pyridin-2-yl, 3-CN | Me, Me |
| 277 | A31 | 4-MeO-phenyl | 5-F-imidazo[1,2-a]pyridin-2-yl | Me, Me |
| 278 | A31 | 4-CN-phenyl | 5-F-imidazo[1,2-a]pyridin-2-yl | Me, Me |

-continued
| Example # | HET | X | Z | R₂ |
|---|---|---|---|---|
| 279 | A31 | 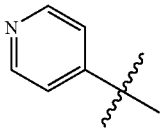 [SMILES: *c1ccncc1] | 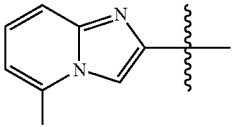 | Me, Me |
| 280 | A31 | 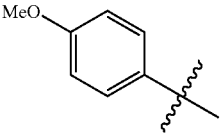 [SMILES: *c1ccc(OC)cc1] | 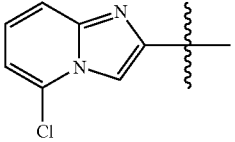 | Me, Me |
| 281 | A31 | 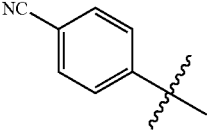 | 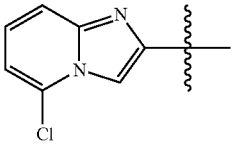 [SMILES: *c1cn2c(Cl)cccc2n1] | Me, Me |
| 282 | A31 | 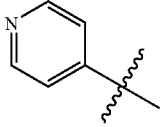 [SMILES: *c1ccncc1] | 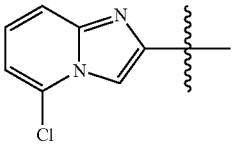 | Me, Me |
| 283 | A31 | 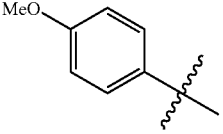 [SMILES: *c1ccc(OC)cc1] | 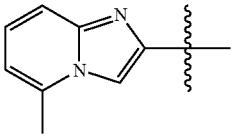 [SMILES: *c1cn2c(C)cccc2n1] | Me, Me |
| 284 | A31 | 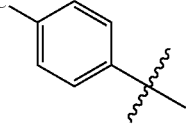 | 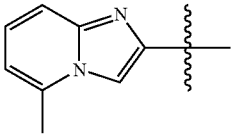 [SMILES: *c1cn2c(C)cccc2n1] | Me, Me |
| 285 | A31 | 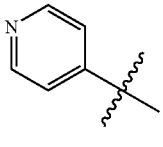 [SMILES: *c1ccncc1] | 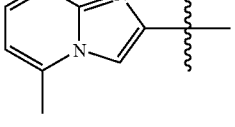 | Me, Me |
| 286 | A31 | 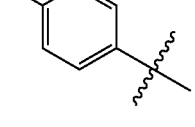 | 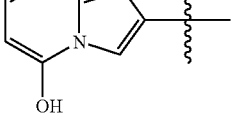 | Me, Me |
| 287 | A31 | 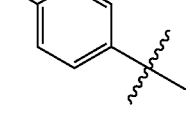 | 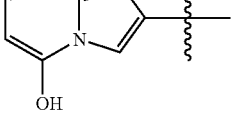 | Me, Me |
| 288 | A31 | 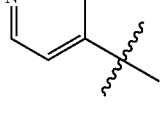 | 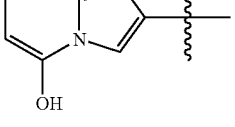 | Me, Me |

-continued

| Example # | HET | X | Z | R$_2$ |
|---|---|---|---|---|
| 289 | A31 | 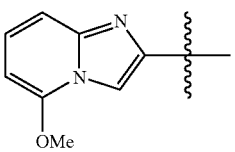 [SMILES: *c1cn2c(C#N)cccc2n1] MeO-phenyl | 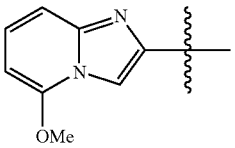 imidazo[1,2-a]pyridine, OMe | Me, Me |
| 290 | A31 | NC-phenyl | imidazo[1,2-a]pyridine, OMe | Me, Me |
| 291 | A31 | pyridyl | imidazo[1,2-a]pyridine, OMe | Me, Me |
| 292 | A31 | MeO-phenyl | imidazo[1,2-a]pyridine, OCF$_3$ | Me, Me |
| 293 | A31 | NC-phenyl | imidazo[1,2-a]pyridine, OCF$_3$ | Me, Me |
| 294 | A31 | pyridyl | imidazo[1,2-a]pyridine, OCF$_3$ | Me, Me |
| 295 | A31 | MeO-phenyl | imidazo[1,2-a]pyridine, CN | Me, Me |
| 296 | A31 | NC-phenyl | imidazo[1,2-a]pyridine, CN | Me, Me |
| 297 | A31 | pyridyl | imidazo[1,2-a]pyridine, CN | Me, Me |
| 298 | A31 | MeO-phenyl | 6-F-imidazo[1,2-a]pyridine | Me, Me |

-continued
| Example # | HET | X | Z | R₂ |
|---|---|---|---|---|
| 299 | A31 | 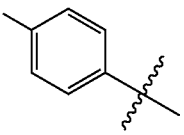 | 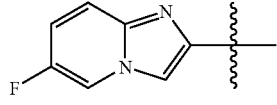 [SMILES: *c1cn2cc(F)ccc2n1] | Me, Me |
| 300 | A31 | 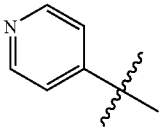 [SMILES: *c1ccncc1] | 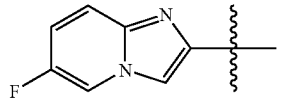 [SMILES: *c1cn2cc(F)ccc2n1] | Me, Me |
| 301 | A31 | 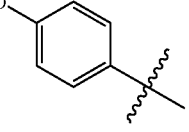 | 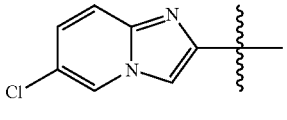 [SMILES: *c1cn2cc(Cl)ccc2n1] | Me, Me |
| 302 | A31 | 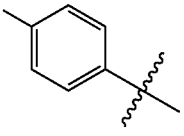 | 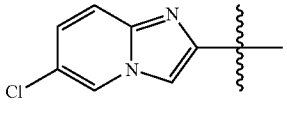 [SMILES: *c1cn2cc(Cl)ccc2n1] | Me, Me |
| 303 | A31 | 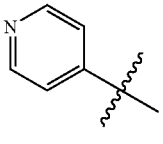 [SMILES: *c1ccncc1] | 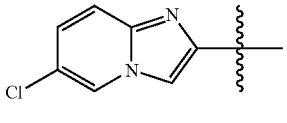 [SMILES: *c1cn2cc(Cl)ccc2n1] | Me, Me |
| 304 | A31 | 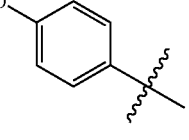 | 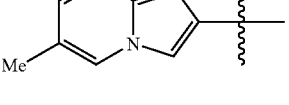 | Me, Me |
| 305 | A31 | 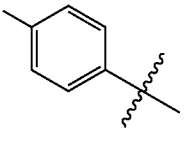 | 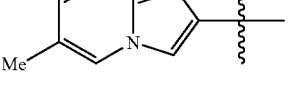 | Me, Me |
| 306 | A31 | 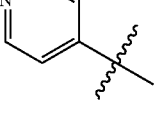 | 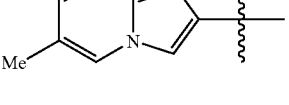 | Me, Me |
| 307 | A31 | 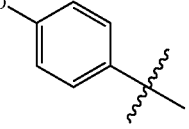 | 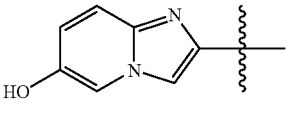 | Me, Me |
| 308 | A31 | 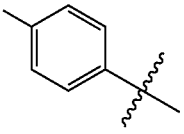 | 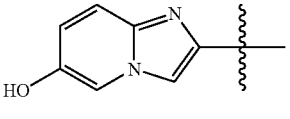 | Me, Me |

-continued

| Example # | HET | X | Z | R₂ |
|---|---|---|---|---|
| 309 | A31 | 4-pyridyl | 6-hydroxy-imidazo[1,2-a]pyridin-2-yl | Me, Me |
| 310 | A31 | 4-MeO-phenyl | 6-MeO-imidazo[1,2-a]pyridin-2-yl | Me, Me |
| 311 | A31 | 4-NC-phenyl | 6-MeO-imidazo[1,2-a]pyridin-2-yl | Me, Me |
| 312 | A31 | 4-pyridyl | 6-MeO-imidazo[1,2-a]pyridin-2-yl | Me, Me |
| 313 | A31 | 4-MeO-phenyl | 6-F₃CO-imidazo[1,2-a]pyridin-2-yl | Me, Me |
| 314 | A31 | 4-NC-phenyl | 6-F₃CO-imidazo[1,2-a]pyridin-2-yl | Me, Me |
| 315 | A31 | 4-pyridyl | 6-F₃CO-imidazo[1,2-a]pyridin-2-yl | Me, Me |
| 316 | A31 | 4-MeO-phenyl | 6-NC-imidazo[1,2-a]pyridin-2-yl | Me, Me |
| 317 | A31 | 4-NC-phenyl | 6-NC-imidazo[1,2-a]pyridin-2-yl | Me, Me |
| 318 | A31 | 4-pyridyl | 6-NC-imidazo[1,2-a]pyridin-2-yl | Me, Me |

-continued
| Example # | HET | X | Z | R₂ |
|---|---|---|---|---|
| 319 | A31 | 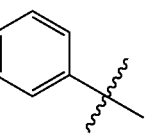 | 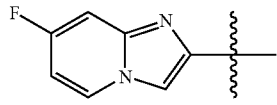 | Me, Me |
| 320 | A31 |  | 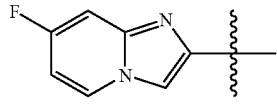 [SMILES: *c1cn2ccc(F)cc2n1] | Me, Me |
| 321 | A31 | 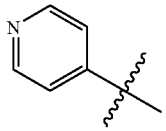 [SMILES: *c1ccncc1] | 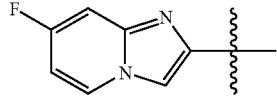 [SMILES: *c1cn2ccc(F)cc2n1] | Me, Me |
| 322 | A31 | 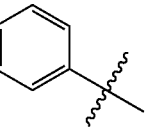 | 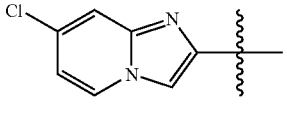 [SMILES: *c1cn2ccc(Cl)cc2n1] | Me, Me |
| 323 | A31 |  | 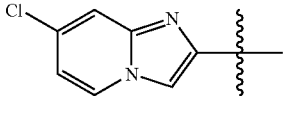 [SMILES: *c1cn2ccc(Cl)cc2n1] | Me, Me |
| 324 | A31 | 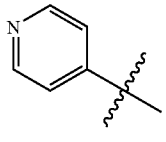 | 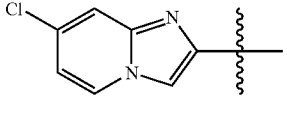 [SMILES: *c1cn2ccc(Cl)cc2n1] | Me, Me |
| 325 | A31 | 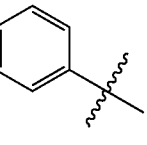 | 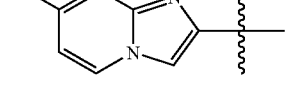 | Me, Me |
| 326 | A31 | 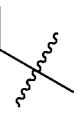 | 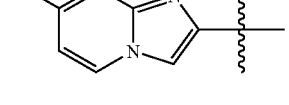 | Me, Me |
| 327 | A31 | 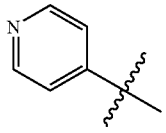 | 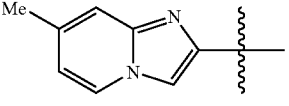 | Me, Me |
| 328 | A31 | 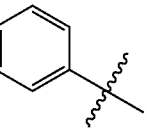 | 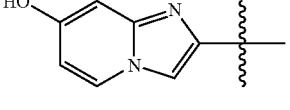 | Me, Me |

-continued

| Example # | HET | X | Z | R₂ |
|---|---|---|---|---|
| 329 | A31 | 4-cyanophenyl | 7-hydroxyimidazo[1,2-a]pyridin-2-yl | Me, Me |
| 330 | A31 | pyridin-4-yl | 7-hydroxyimidazo[1,2-a]pyridin-2-yl | Me, Me |
| 331 | A31 | 4-methoxyphenyl | 7-methoxyimidazo[1,2-a]pyridin-2-yl | Me, Me |
| 332 | A31 | 4-cyanophenyl | 7-methoxyimidazo[1,2-a]pyridin-2-yl | Me, Me |
| 333 | A31 | pyridin-4-yl | 7-methoxyimidazo[1,2-a]pyridin-2-yl | Me, Me |
| 334 | A31 | 4-methoxyphenyl | 7-trifluoromethoxyimidazo[1,2-a]pyridin-2-yl | Me, Me |
| 335 | A31 | 4-cyanophenyl | 7-trifluoromethoxyimidazo[1,2-a]pyridin-2-yl | Me, Me |
| 336 | A31 | pyridin-4-yl | 7-trifluoromethoxyimidazo[1,2-a]pyridin-2-yl | Me, Me |
| 337 | A31 | 4-methoxyphenyl | 7-cyanoimidazo[1,2-a]pyridin-2-yl | Me, Me |
| 338 | A31 | 4-cyanophenyl | 7-cyanoimidazo[1,2-a]pyridin-2-yl | Me, Me |

-continued

| Example # | HET | X | Z | R₂ |
|---|---|---|---|---|
| 339 | A31 | 4-pyridyl | 7-cyano-imidazo[1,2-a]pyridin-2-yl | Me, Me |
| 340 | A31 | 4-MeO-phenyl | imidazo[1,2-b]pyridazin-6-yl | Me, Me |
| 341 | A31 | 4-NC-phenyl | imidazo[1,2-b]pyridazin-6-yl | Me, Me |
| 342 | A31 | 4-pyridyl | imidazo[1,2-b]pyridazin-6-yl | Me, Me |
| 343 | A31 | 4-MeO-phenyl | 3-fluoro-imidazo[1,2-b]pyridazin-6-yl | Me, Me |
| 344 | A31 | 4-NC-phenyl | 3-fluoro-imidazo[1,2-b]pyridazin-6-yl | Me, Me |
| 345 | A31 | 4-pyridyl | 3-fluoro-imidazo[1,2-b]pyridazin-6-yl | Me, Me |
| 346 | A31 | 4-MeO-phenyl | 3-chloro-imidazo[1,2-b]pyridazin-6-yl | Me, Me |
| 347 | A31 | 4-NC-phenyl | 3-chloro-imidazo[1,2-b]pyridazin-6-yl | Me, Me |
| 348 | A31 | 4-pyridyl | 3-chloro-imidazo[1,2-b]pyridazin-6-yl | Me, Me |

-continued
| Example # | HET | X | Z | R₂ |
|---|---|---|---|---|
| 349 | A31 |  | 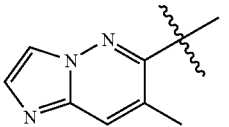 [SMILES: *c1nn2ccnc2cc1C] | Me, Me |
| 350 | A31 |  | 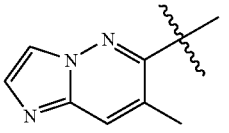 | Me, Me |
| 351 | A31 |  | 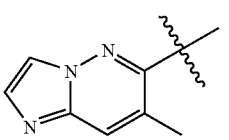 | Me, Me |
| 352 | A31 |  | 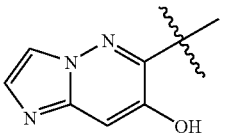 [SMILES: *c1nn2ccnc2cc1O] | Me, Me |
| 353 | A31 |  | 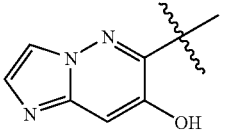 [SMILES: *c1nn2ccnc2cc1O] | Me, Me |
| 354 | A31 |  | 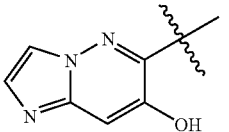 [SMILES: *c1nn2ccnc2cc1O] | Me, Me |
| 355 | A31 |  | 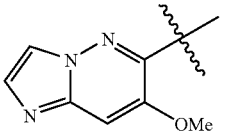 [SMILES: *c1nn2ccnc2cc1OC] | Me, Me |
| 356 | A31 |  | 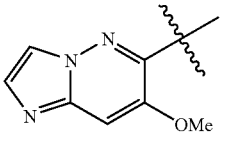 [SMILES: *c1nn2ccnc2cc1OC] | Me, Me |
| 357 | A31 |  | 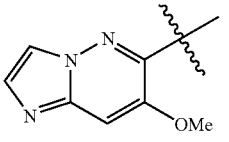 [SMILES: *c1nn2ccnc2cc1OC] | Me, Me |
| 358 | A31 |  | 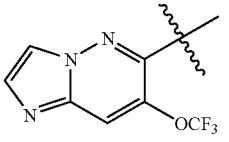 [SMILES: *c1nn2ccnc2cc1OC(F)(F)F] | Me, Me |

-continued

| Example # | HET | X | Z | R₂ |
|---|---|---|---|---|
| 359 | A31 | 4-NC-C₆H₄- | imidazo[1,2-b]pyridazine-6-yl, 7-OCF₃ | Me, Me |
| 360 | A31 | pyridin-4-yl | imidazo[1,2-b]pyridazine-6-yl, 7-OCF₃ | Me, Me |
| 361 | A31 | 4-MeO-C₆H₄- | imidazo[1,2-b]pyridazine-6-yl, 7-CN | Me, Me |
| 362 | A31 | 4-NC-C₆H₄- | imidazo[1,2-b]pyridazine-6-yl, 7-CN | Me, Me |
| 363 | A31 | pyridin-4-yl | imidazo[1,2-b]pyridazine-6-yl, 7-CN | Me, Me |
| 364 | A31 | 4-MeO-C₆H₄- | imidazo[1,2-b]pyridazine-6-yl, 8-F | Me, Me |
| 365 | A31 | 4-NC-C₆H₄- | imidazo[1,2-b]pyridazine-6-yl, 8-F | Me, Me |
| 366 | A31 | pyridin-4-yl | imidazo[1,2-b]pyridazine-6-yl, 8-F | Me, Me |
| 367 | A31 | 4-MeO-C₆H₄- | imidazo[1,2-b]pyridazine-6-yl, 8-Cl | Me, Me |

-continued

| Example # | HET | X | Z | R$_2$ |
|---|---|---|---|---|
| 368 | A31 | NC-phenyl | imidazopyridazine, Cl | Me, Me |
| 369 | A31 | 4-pyridyl | imidazopyridazine, Cl | Me, Me |
| 370 | A31 | MeO-phenyl | imidazopyridazine, Me | Me, Me |
| 371 | A31 | NC-phenyl | imidazopyridazine, Me | Me, Me |
| 372 | A31 | 4-pyridyl | imidazopyridazine, Me | Me, Me |
| 373 | A31 | MeO-phenyl | imidazopyridazine, OH | Me, Me |
| 374 | A31 | NC-phenyl | imidazopyridazine, OH | Me, Me |
| 375 | A31 | 4-pyridyl | imidazopyridazine, OH | Me, Me |

-continued
| Example # | HET | X | Z | R₂ |
|---|---|---|---|---|
| 376 | A31 | 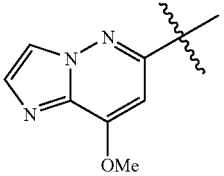 [SMILES: *c1cc(OC)c2nccn2n1] | 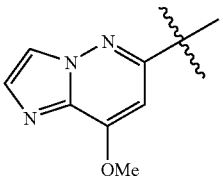 [SMILES: *c1cc(OC)c2nccn2n1] | Me, Me |
| 377 | A31 | 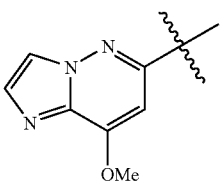 [SMILES: *c1cc(OC)c2nccn2n1] | 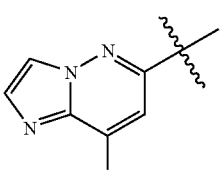 | Me, Me |
| 378 | A31 | 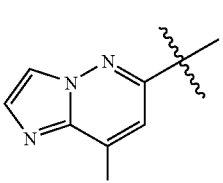 | 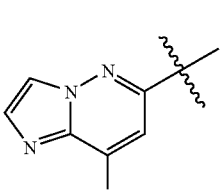 | Me, Me |
| 379 | A31 | 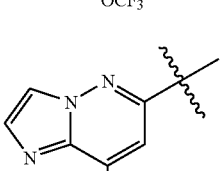 | 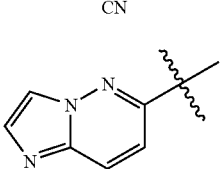 | Me, Me |
| 380 | A31 | | | Me, Me |
| 381 | A31 | | | Me, Me |
| 382 | A31 | | | Me, Me |
| 383 | A31 | | | Me, Me |

-continued

| Example # | HET | X | Z | R₂ |
|---|---|---|---|---|
| 384 | A31 | 4-pyridyl | 4-cyano-imidazo[1,2-b]pyridazin-6-yl | Me, Me |
| 385 | A31 | 4-methoxyphenyl | 2-fluoro-imidazo[1,2-b]pyridazin-6-yl | Me, Me |
| 386 | A31 | 4-cyanophenyl | 2-fluoro-imidazo[1,2-b]pyridazin-6-yl | Me, Me |
| 387 | A31 | 4-pyridyl | 2-fluoro-imidazo[1,2-b]pyridazin-6-yl | Me, Me |
| 388 | A31 | 4-methoxyphenyl | 2-chloro-imidazo[1,2-b]pyridazin-6-yl | Me, Me |
| 389 | A31 | 4-cyanophenyl | 2-chloro-imidazo[1,2-b]pyridazin-6-yl | Me, Me |
| 390 | A31 | 4-pyridyl | 2-chloro-imidazo[1,2-b]pyridazin-6-yl | Me, Me |
| 391 | A31 | 4-methoxyphenyl | 2-methyl-imidazo[1,2-b]pyridazin-6-yl | Me, Me |
| 392 | A31 | 4-cyanophenyl | 2-methyl-imidazo[1,2-b]pyridazin-6-yl | Me, Me |
| 393 | A31 | 4-pyridyl | 2-methyl-imidazo[1,2-b]pyridazin-6-yl | Me, Me |

-continued
| Example # | HET | X | Z | R₂ |
|---|---|---|---|---|
| 394 | A31 | 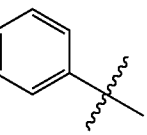 | 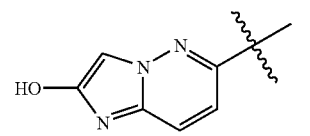 | Me, Me |
| 395 | A31 | 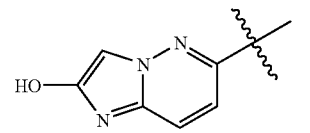 | 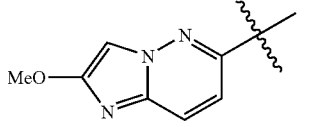 [SMILES: *c1ccc2nc(OC)cn2n1] | Me, Me |
| 396 | A31 | 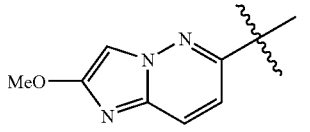 [SMILES: *c1ccc2nc(OC)cn2n1] | 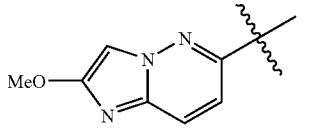 [SMILES: *c1ccc2nc(OC)cn2n1] | Me, Me |
| 397 | A31 | 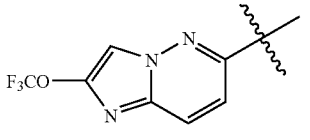 [SMILES: *c1ccc2nc(OC(F)(F)F)cn2n1] | 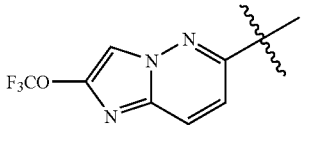 [SMILES: *c1ccc2nc(OC(F)(F)F)cn2n1] | Me, Me |
| 398 | A31 | 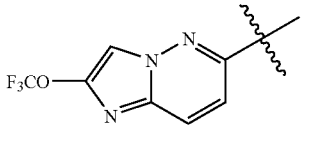 [SMILES: *c1ccc2nc(OC(F)(F)F)cn2n1] | 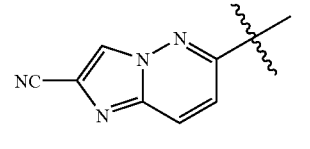 | Me, Me |
| 399 | A31 | | | Me, Me |
| 400 | A31 | | | Me, Me |
| 401 | A31 | | | Me, Me |
| 402 | A31 | | | Me, Me |
| 403 | A31 | | | Me, Me |

-continued
| Example # | HET | X | Z | R₂ |
|---|---|---|---|---|
| 404 | A31 | 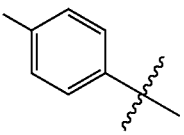 | 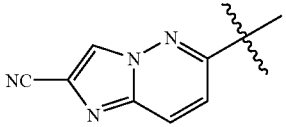 | Me, Me |
| 405 | A31 | 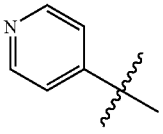 [SMILES: *c1ccncc1] | 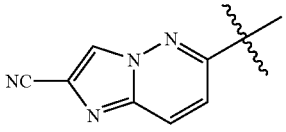 | Me, Me |
| 406 | A31 | 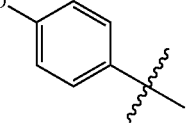 | 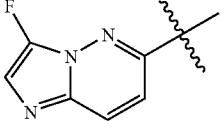 [SMILES: *c1ccc2ncc(F)n2n1] | Me, Me |
| 407 | A31 | 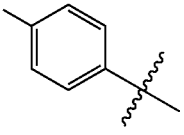 | 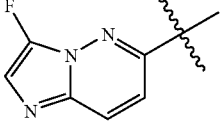 [SMILES: *c1ccc2ncc(C)n2n1] | Me, Me |
| 408 | A31 | 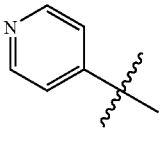 | 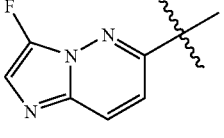 [SMILES: *c1ccc2ncc(C)n2n1] | Me, Me |
| 409 | A31 | 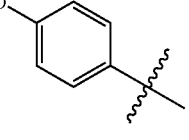 | 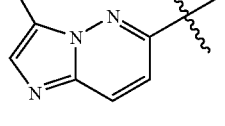 | Me, Me |
| 410 | A31 | 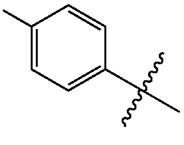 | 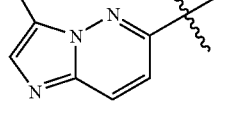 | Me, Me |
| 411 | A31 | 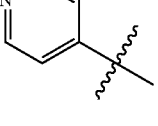 | 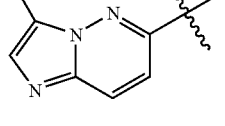 | Me, Me |
| 412 | A31 | 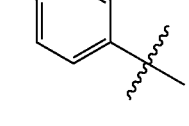 | 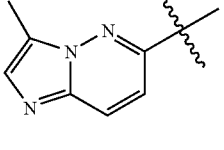 | Me, Me |
| 413 | A31 | 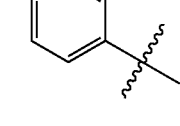 | 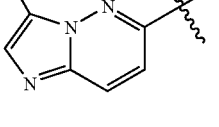 | Me, Me |

-continued

| Example # | HET | X | Z | R₂ |
|---|---|---|---|---|
| 414 | A31 | 4-pyridyl | 3-methyl-imidazo[1,2-b]pyridazin-6-yl | Me, Me |
| 415 | A31 | 4-MeO-phenyl | 3-hydroxy-imidazo[1,2-b]pyridazin-6-yl | Me, Me |
| 416 | A31 | 4-NC-phenyl | 3-hydroxy-imidazo[1,2-b]pyridazin-6-yl | Me, Me |
| 417 | A31 | 4-pyridyl | 3-hydroxy-imidazo[1,2-b]pyridazin-6-yl | Me, Me |
| 418 | A31 | 4-MeO-phenyl | 3-methoxy-imidazo[1,2-b]pyridazin-6-yl | Me, Me |
| 419 | A31 | 4-NC-phenyl | 3-methoxy-imidazo[1,2-b]pyridazin-6-yl | Me, Me |
| 420 | A31 | 4-pyridyl | 3-methoxy-imidazo[1,2-b]pyridazin-6-yl | Me, Me |
| 421 | A31 | 4-MeO-phenyl | 3-trifluoromethoxy-imidazo[1,2-b]pyridazin-6-yl | Me, Me |
| 422 | A31 | 4-NC-phenyl | 3-trifluoromethoxy-imidazo[1,2-b]pyridazin-6-yl | Me, Me |
| 423 | A31 | 4-pyridyl | 3-trifluoromethoxy-imidazo[1,2-b]pyridazin-6-yl | Me, Me |

| Example # | HET | X | Z | R₂ |
|---|---|---|---|---|
| 424 | A31 | 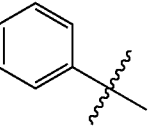 | 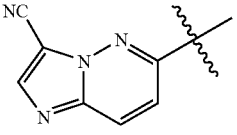 | Me, Me |
| 425 | A31 |  | 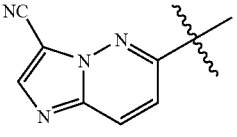 | Me, Me |
| 426 | A31 | 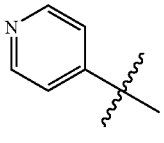 [SMILES: *c1ccncc1] | 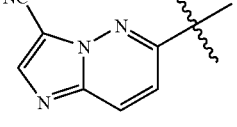 | Me, Me |
| 427 | A31 | 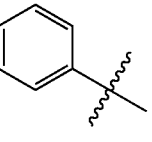 | 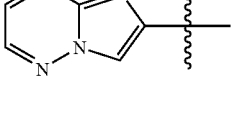 | Me, Me |
| 428 | A31 |  | 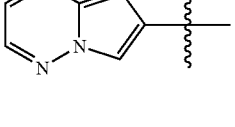 | Me, Me |
| 429 | A31 | 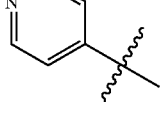 | 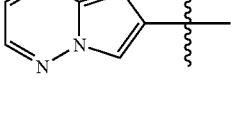 | Me, Me |
| 430 | A31 | 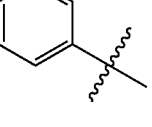 | 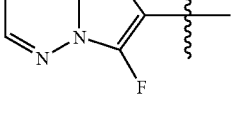 | Me, Me |
| 431 | A31 | 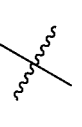 | 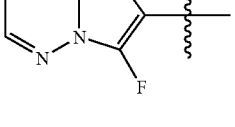 | Me, Me |
| 432 | A31 | 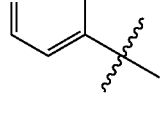 | 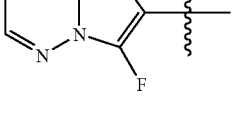 | Me, Me |
| 433 | A31 | 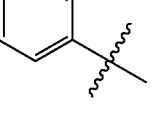 | 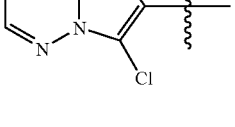 | Me, Me |

-continued

| Example # | HET | X | Z | R₂ |
|---|---|---|---|---|
| 434 | A31 | 4-CN-phenyl | imidazo[1,2-b]pyridazin-2-yl, 3-Cl | Me, Me |
| 435 | A31 | pyridin-4-yl | imidazo[1,2-b]pyridazin-2-yl, 3-Cl | Me, Me |
| 436 | A31 | 4-MeO-phenyl | imidazo[1,2-b]pyridazin-2-yl, 3-Me | Me, Me |
| 437 | A31 | 4-CN-phenyl | imidazo[1,2-b]pyridazin-2-yl, 3-Me | Me, Me |
| 438 | A31 | pyridin-4-yl | imidazo[1,2-b]pyridazin-2-yl, 3-Me | Me, Me |
| 439 | A31 | 4-MeO-phenyl | imidazo[1,2-b]pyridazin-2-yl, 3-OH | Me, Me |
| 440 | A31 | 4-CN-phenyl | imidazo[1,2-b]pyridazin-2-yl, 3-OH | Me, Me |
| 441 | A31 | pyridin-4-yl | imidazo[1,2-b]pyridazin-2-yl, 3-OH | Me, Me |
| 442 | A31 | 4-MeO-phenyl | imidazo[1,2-b]pyridazin-2-yl, 3-OMe | Me, Me |
| 443 | A31 | 4-CN-phenyl | imidazo[1,2-b]pyridazin-2-yl, 3-OMe | Me, Me |

-continued

| Example # | HET | X | Z | R₂ |
|---|---|---|---|---|
| 444 | A31 | 4-pyridyl | imidazo[1,2-b]pyridazin-2-yl, 3-OMe | Me, Me |
| 445 | A31 | 4-MeO-phenyl | imidazo[1,2-b]pyridazin-2-yl, 3-OCF₃ | Me, Me |
| 446 | A31 | 4-NC-phenyl | imidazo[1,2-b]pyridazin-2-yl, 3-OCF₃ | Me, Me |
| 447 | A31 | 4-pyridyl | imidazo[1,2-b]pyridazin-2-yl, 3-OCF₃ | Me, Me |
| 448 | A31 | 4-MeO-phenyl | imidazo[1,2-b]pyridazin-2-yl, 3-CN | Me, Me |
| 449 | A31 | 4-NC-phenyl | imidazo[1,2-b]pyridazin-2-yl, 3-CN | Me, Me |
| 450 | A31 | 4-pyridyl | imidazo[1,2-b]pyridazin-2-yl, 3-CN | Me, Me |
| 451 | A31 | 4-MeO-phenyl | 6-F-imidazo[1,2-b]pyridazin-2-yl | Me, Me |
| 452 | A31 | 4-NC-phenyl | 6-F-imidazo[1,2-b]pyridazin-2-yl | Me, Me |
| 453 | A31 | 4-pyridyl | 6-F-imidazo[1,2-b]pyridazin-2-yl | Me, Me |

-continued

| Example # | HET | X | Z | R₂ |
|---|---|---|---|---|
| 454 | A31 | 4-MeO-phenyl | 6-Cl-imidazo[1,2-b]pyridazin-2-yl | Me, Me |
| 455 | A31 | 4-NC-phenyl | 6-Cl-imidazo[1,2-b]pyridazin-2-yl | Me, Me |
| 456 | A31 | pyridin-4-yl | 6-Cl-imidazo[1,2-b]pyridazin-2-yl | Me, Me |
| 457 | A31 | 4-MeO-phenyl | 6-Me-imidazo[1,2-b]pyridazin-2-yl | Me, Me |
| 458 | A31 | 4-NC-phenyl | 6-Me-imidazo[1,2-b]pyridazin-2-yl | Me, Me |
| 459 | A31 | pyridin-4-yl | 6-Me-imidazo[1,2-b]pyridazin-2-yl | Me, Me |
| 460 | A31 | 4-MeO-phenyl | 6-HO-imidazo[1,2-b]pyridazin-2-yl | Me, Me |
| 461 | A31 | 4-NC-phenyl | 6-HO-imidazo[1,2-b]pyridazin-2-yl | Me, Me |
| 462 | A31 | pyridin-4-yl | 6-HO-imidazo[1,2-b]pyridazin-2-yl | Me, Me |
| 463 | A31 | 4-MeO-phenyl | 6-MeO-imidazo[1,2-b]pyridazin-2-yl | Me, Me |

-continued
| Example # | HET | X | Z | R₂ |
|---|---|---|---|---|
| 464 | A31 | 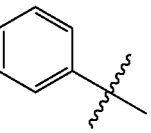 | 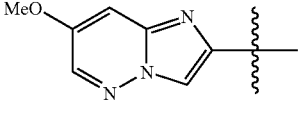 [SMILES: *c1cn2ncc(OC)cc2n1] | Me, Me |
| 465 | A31 | 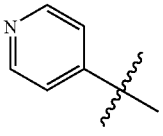 [SMILES: *c1ccncc1] | 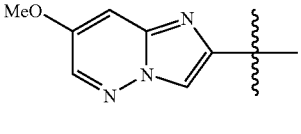 | Me, Me |
| 466 | A31 | 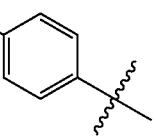 | 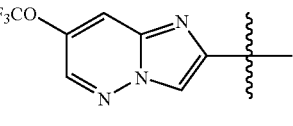 | Me, Me |
| 467 | A31 |  | 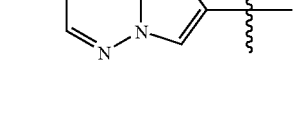 | Me, Me |
| 468 | A31 | 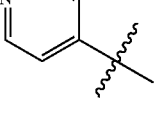 | 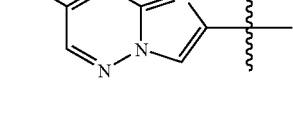 | Me, Me |
| 469 | A31 |  | 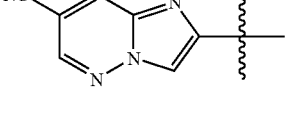 | Me, Me |
| 470 | A31 |  | 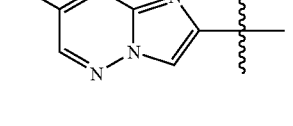 | Me, Me |
| 471 | A31 | 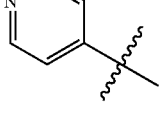 | 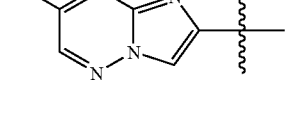 | Me, Me |
| 472 | A31 |  | 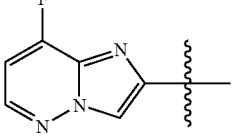 | Me, Me |
| 473 | A31 |  | 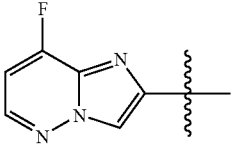 | Me, Me |

-continued

| Example # | HET | X | Z | R₂ |
|---|---|---|---|---|
| 474 | A31 | 4-pyridyl | 8-F-imidazo[1,2-b]pyridazin-2-yl | Me, Me |
| 475 | A31 | 4-MeO-phenyl | 8-Cl-imidazo[1,2-b]pyridazin-2-yl | Me, Me |
| 476 | A31 | 4-NC-phenyl | 8-Cl-imidazo[1,2-b]pyridazin-2-yl | Me, Me |
| 477 | A31 | 4-pyridyl | 8-Cl-imidazo[1,2-b]pyridazin-2-yl | Me, Me |
| 478 | A31 | 4-MeO-phenyl | 8-Me-imidazo[1,2-b]pyridazin-2-yl | Me, Me |
| 479 | A31 | 4-NC-phenyl | 8-Me-imidazo[1,2-b]pyridazin-2-yl | Me, Me |
| 480 | A31 | 4-pyridyl | 8-Me-imidazo[1,2-b]pyridazin-2-yl | Me, Me |
| 481 | A31 | 4-MeO-phenyl | 8-OH-imidazo[1,2-b]pyridazin-2-yl | Me, Me |
| 482 | A31 | 4-NC-phenyl | 8-OH-imidazo[1,2-b]pyridazin-2-yl | Me, Me |

-continued
| Example # | HET | X | Z | R₂ |
|---|---|---|---|---|
| 483 | A31 | 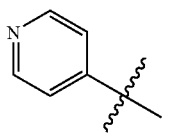 [SMILES: *c1ccncc1] | 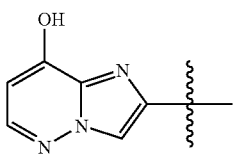 | Me, Me |
| 484 | A31 | 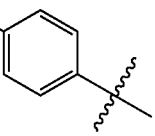 | 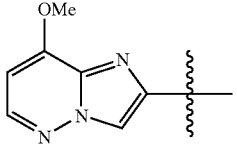 | Me, Me |
| 485 | A31 | 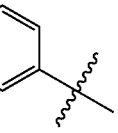 | 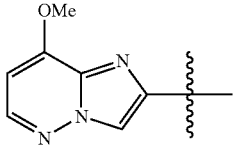 [SMILES: *c1cn2nccc(OC)c2n1] | Me, Me |
| 486 | A31 | 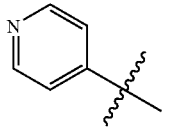 [SMILES: *c1ccncc1] | 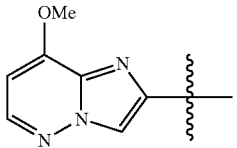 [SMILES: *c1cn2nccc(OC)c2n1] | Me, Me |
| 487 | A31 | 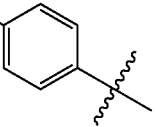 | 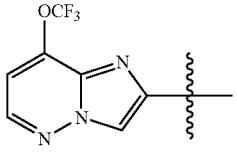 [SMILES: *c1cn2nccc(OC(F)(F)F)c2n1] | Me, Me |
| 488 | A31 | 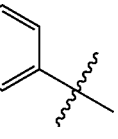 | 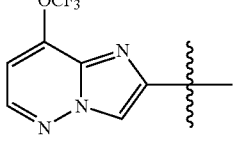 | Me, Me |
| 489 | A31 | 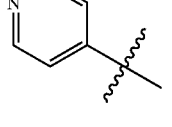 | 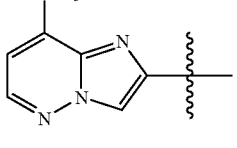 | Me, Me |
| 490 | A31 | 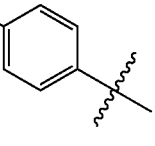 | 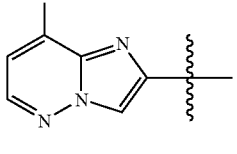 | Me, Me |
| 491 | A31 | 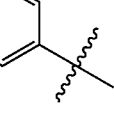 | 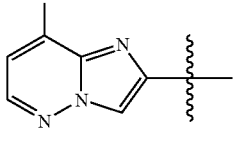 | Me, Me |

-continued
| Example # | HET | X | Z | R₂ |
|---|---|---|---|---|
| 492 | A31 | 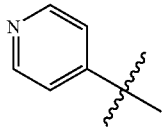 [SMILES: *c1ccncc1] | 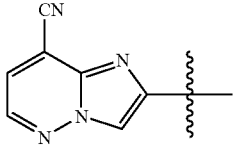 [SMILES: *c1cn2nccc(C#N)c2n1] | Me, Me |
| 493 | A29 | 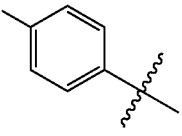 | 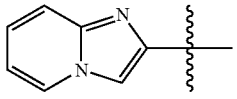 [SMILES: *c1cn2ccccc2n1] | --cyclopropyl-- |
| 494 | A29 | 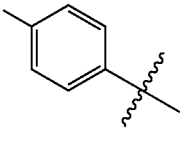 | 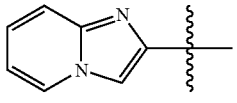 [SMILES: *c1cn2ccccc2n1] | --cyclopropyl-- |
| 495 | A29 | 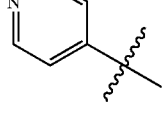 | 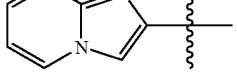 | --cyclopropyl-- |
| 496 | A29 | 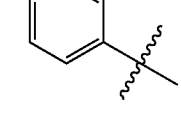 | 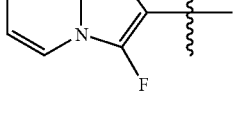 | --cyclopropyl-- |
| 497 | A29 | 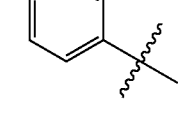 | 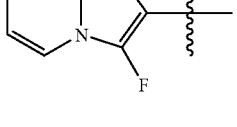 | --cyclopropyl-- |
| 498 | A29 | 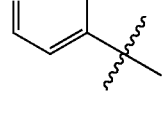 | 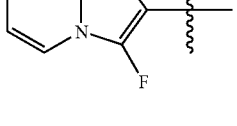 | --cyclopropyl-- |
| 499 | A29 | 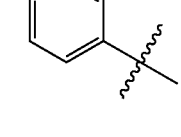 | 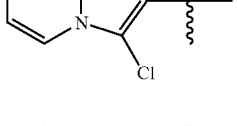 | --cyclopropyl-- |
| 500 | A29 | 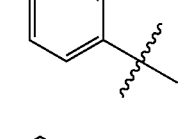 | 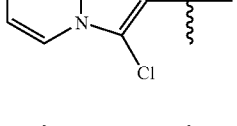 | --cyclopropyl-- |
| 501 | A29 | 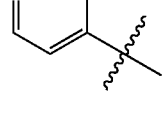 | 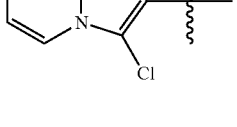 | --cyclopropyl-- |

-continued
| Example # | HET | X | Z | R₂ |
|---|---|---|---|---|
| 502 | A29 | 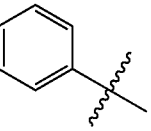 | 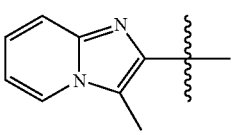 [SMILES: *c1nc2ccccn2c1C] | --cyclopropyl-- |
| 503 | A29 | 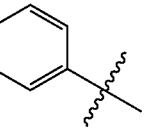 | 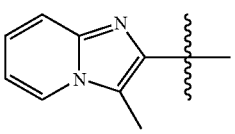 [SMILES: *c1nc2ccccn2c1C] | --cyclopropyl-- |
| 504 | A29 | 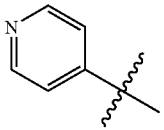 | 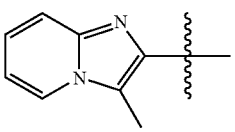 [SMILES: *c1nc2ccccn2c1C] | --cyclopropyl-- |
| 505 | A29 | 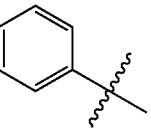 | 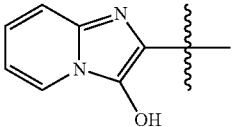 | --cyclopropyl-- |
| 506 | A29 | 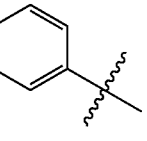 | 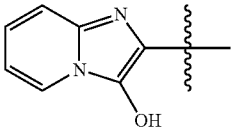 [SMILES: *c1nc2ccccn2c1O] | --cyclopropyl-- |
| 507 | A29 | 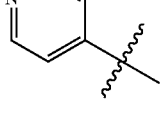 | 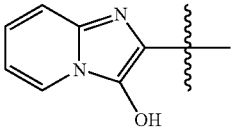 [SMILES: *c1nc2ccccn2c1O] | --cyclopropyl-- |
| 508 | A29 | 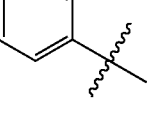 | 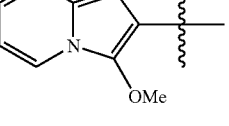 | --cyclopropyl-- |
| 509 | A29 | 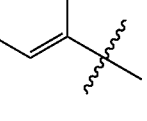 | 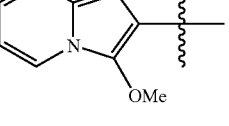 | --cyclopropyl-- |
| 510 | A29 | 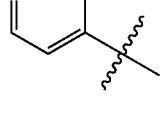 | 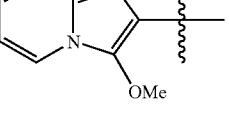 | --cyclopropyl-- |
| 511 | A29 | 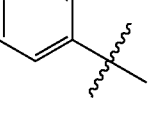 | 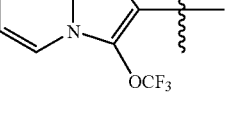 | --cyclopropyl-- |

-continued
| Example # | HET | X | Z | R₂ |
|---|---|---|---|---|
| 512 | A29 | 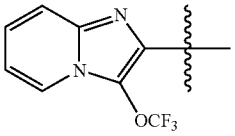 [SMILES: *c1nc2ccccn2c1OC(F)(F)F] | 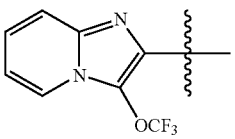 | --cyclopropyl-- |
| 513 | A29 | 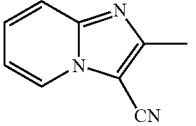 | 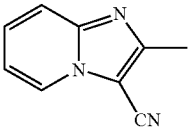 | --cyclopropyl-- |
| 514 | A29 | MeO- | 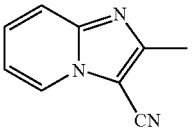 | --cyclopropyl-- |
| 515 | A29 | NC- | 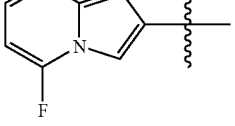 | --cyclopropyl-- |
| 516 | A29 | 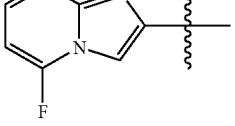 | 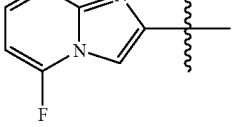 | --cyclopropyl-- |
| 517 | A29 | MeO- | 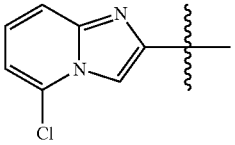 | --cyclopropyl-- |
| 518 | A29 | NC- | 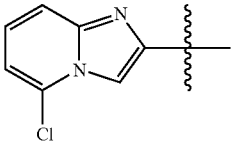 [SMILES: *c1cn2c(Cl)cccc2n1] | --cyclopropyl-- |
| 519 | A29 | pyridyl | imidazo[1,2-a]pyridine, F | --cyclopropyl-- |
| 520 | A29 | MeO- | imidazo[1,2-a]pyridine, Cl | --cyclopropyl-- |
| 521 | A29 | NC- | imidazo[1,2-a]pyridine, Cl | --cyclopropyl-- |

-continued

| Example # | HET | X | Z | R₂ |
|---|---|---|---|---|
| 522 | A29 | 4-pyridyl | 5-chloroimidazo[1,2-a]pyridin-2-yl | --cyclopropyl-- |
| 523 | A29 | 4-methoxyphenyl | 5-methylimidazo[1,2-a]pyridin-2-yl | --cyclopropyl-- |
| 524 | A29 | 4-cyanophenyl | 5-methylimidazo[1,2-a]pyridin-2-yl | --cyclopropyl-- |
| 525 | A29 | 4-pyridyl | 5-methylimidazo[1,2-a]pyridin-2-yl | --cyclopropyl-- |
| 526 | A29 | 4-methoxyphenyl | 5-hydroxyimidazo[1,2-a]pyridin-2-yl | --cyclopropyl-- |
| 527 | A29 | 4-cyanophenyl | 5-hydroxyimidazo[1,2-a]pyridin-2-yl | --cyclopropyl-- |
| 528 | A29 | 4-pyridyl | 5-hydroxyimidazo[1,2-a]pyridin-2-yl | --cyclopropyl-- |
| 529 | A29 | 4-methoxyphenyl | 5-methoxyimidazo[1,2-a]pyridin-2-yl | --cyclopropyl-- |
| 530 | A29 | 4-cyanophenyl | 5-methoxyimidazo[1,2-a]pyridin-2-yl | --cyclopropyl-- |
| 531 | A29 | 4-pyridyl | 5-methoxyimidazo[1,2-a]pyridin-2-yl | --cyclopropyl-- |

| Example # | HET | X | Z | R₂ |
|---|---|---|---|---|
| 532 | A29 | 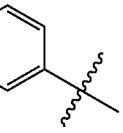 | 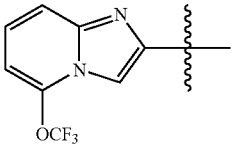 [SMILES: *c1cn2c(OC(F)(F)F)cccc2n1] | --cyclopropyl-- |
| 533 | A29 |  | 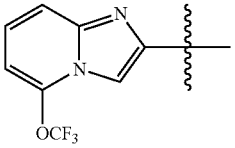 [SMILES: *c1cn2c(OC(F)(F)F)cccc2n1] | --cyclopropyl-- |
| 534 | A29 | 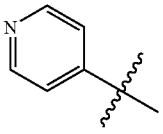 | 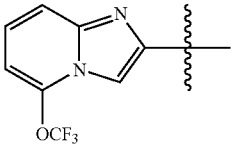 [SMILES: *c1cn2c(OC(F)(F)F)cccc2n1] | --cyclopropyl-- |
| 535 | A29 | 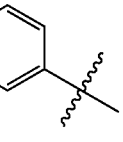 | 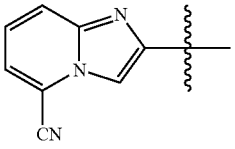 | --cyclopropyl-- |
| 536 | A29 | 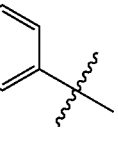 | 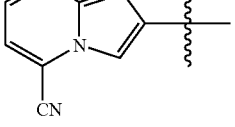 | --cyclopropyl-- |
| 537 | A29 | 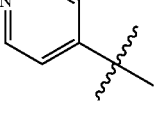 | 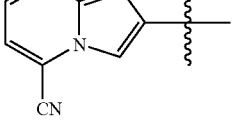 | --cyclopropyl-- |
| 538 | A29 | 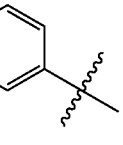 | 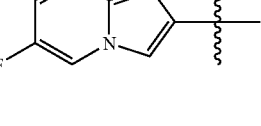 | --cyclopropyl-- |
| 539 | A29 | 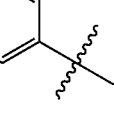 | 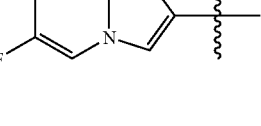 | --cyclopropyl-- |
| 540 | A29 | 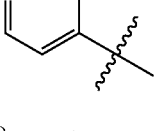 | 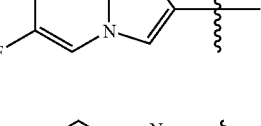 | --cyclopropyl-- |
| 541 | A29 | 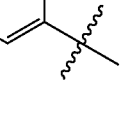 | 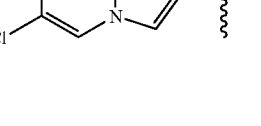 | --cyclopropyl-- |

-continued

| Example # | HET | X | Z | R₂ |
|---|---|---|---|---|
| 542 | A29 | 4-cyanophenyl | 6-chloroimidazo[1,2-a]pyridin-2-yl | --cyclopropyl-- |
| 543 | A29 | pyridin-4-yl | 6-chloroimidazo[1,2-a]pyridin-2-yl | --cyclopropyl-- |
| 544 | A29 | 4-methoxyphenyl | 6-methylimidazo[1,2-a]pyridin-2-yl | --cyclopropyl-- |
| 545 | A29 | 4-cyanophenyl | 6-methylimidazo[1,2-a]pyridin-2-yl | --cyclopropyl-- |
| 546 | A29 | pyridin-4-yl | 6-methylimidazo[1,2-a]pyridin-2-yl | --cyclopropyl-- |
| 547 | A29 | 4-methoxyphenyl | 6-hydroxyimidazo[1,2-a]pyridin-2-yl | --cyclopropyl-- |
| 548 | A29 | 4-cyanophenyl | 6-hydroxyimidazo[1,2-a]pyridin-2-yl | --cyclopropyl-- |
| 549 | A29 | pyridin-4-yl | 6-hydroxyimidazo[1,2-a]pyridin-2-yl | --cyclopropyl-- |
| 550 | A29 | 4-methoxyphenyl | 6-methoxyimidazo[1,2-a]pyridin-2-yl | --cyclopropyl-- |
| 551 | A29 | 4-cyanophenyl | 6-methoxyimidazo[1,2-a]pyridin-2-yl | --cyclopropyl-- |

-continued

| Example # | HET | X | Z | R₂ |
|---|---|---|---|---|
| 552 | A29 | 4-pyridyl | 6-MeO-imidazo[1,2-a]pyridin-2-yl | --cyclopropyl-- |
| 553 | A29 | 4-MeO-phenyl | 6-F₃CO-imidazo[1,2-a]pyridin-2-yl | --cyclopropyl-- |
| 554 | A29 | 4-NC-phenyl | 6-F₃CO-imidazo[1,2-a]pyridin-2-yl | --cyclopropyl-- |
| 555 | A29 | 4-pyridyl | 6-F₃CO-imidazo[1,2-a]pyridin-2-yl | --cyclopropyl-- |
| 556 | A29 | 4-MeO-phenyl | 6-NC-imidazo[1,2-a]pyridin-2-yl | --cyclopropyl-- |
| 557 | A29 | 4-NC-phenyl | 6-NC-imidazo[1,2-a]pyridin-2-yl | --cyclopropyl-- |
| 558 | A29 | 4-pyridyl | 6-NC-imidazo[1,2-a]pyridin-2-yl | --cyclopropyl-- |
| 559 | A29 | 4-MeO-phenyl | 7-F-imidazo[1,2-a]pyridin-2-yl | --cyclopropyl-- |
| 560 | A29 | 4-NC-phenyl | 7-F-imidazo[1,2-a]pyridin-2-yl | --cyclopropyl-- |
| 561 | A29 | 4-pyridyl | 7-F-imidazo[1,2-a]pyridin-2-yl | --cyclopropyl-- |

-continued
| Example # | HET | X | Z | R₂ |
|---|---|---|---|---|
| 562 | A29 | 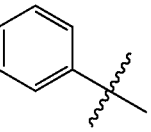 | 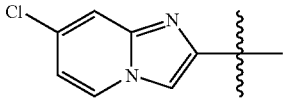 [SMILES: *c1cn2ccc(Cl)cc2n1] | --cyclopropyl-- |
| 563 | A29 |  | 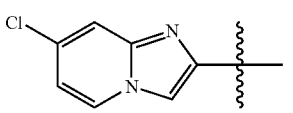 [SMILES: *c1cn2ccc(Cl)cc2n1] | --cyclopropyl-- |
| 564 | A29 | 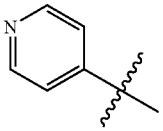 | 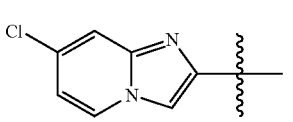 [SMILES: *c1cn2ccc(Cl)cc2n1] | --cyclopropyl-- |
| 565 | A29 |  | 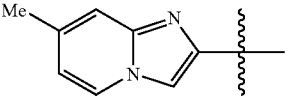 | --cyclopropyl-- |
| 566 | A29 |  | 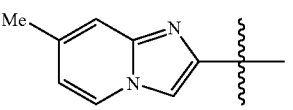 | --cyclopropyl-- |
| 567 | A29 | 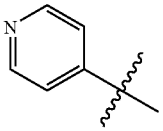 [SMILES: *c1ccncc1] | 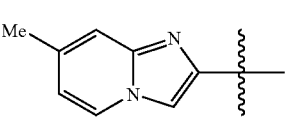 | --cyclopropyl-- |
| 568 | A29 |  | 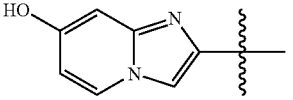 | --cyclopropyl-- |
| 569 | A29 |  | 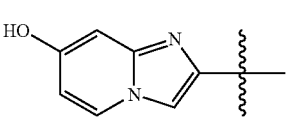 [SMILES: *c1cn2ccc(O)cc2n1] | --cyclopropyl-- |
| 570 | A29 | 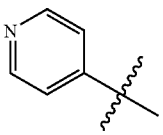 | 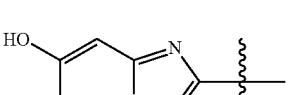 | --cyclopropyl-- |
| 571 | A29 | 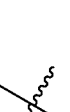 | 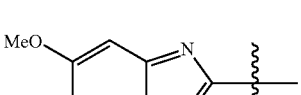 | --cyclopropyl-- |

| Example # | HET | X | Z | R₂ |
|---|---|---|---|---|
| 572 | A29 | NC-C₆H₄- | 7-MeO-imidazo[1,2-a]pyridin-2-yl | --cyclopropyl-- |
| 573 | A29 | pyridin-4-yl | 7-MeO-imidazo[1,2-a]pyridin-2-yl | --cyclopropyl-- |
| 574 | A29 | MeO-C₆H₄- | 7-F₃CO-imidazo[1,2-a]pyridin-2-yl | --cyclopropyl-- |
| 575 | A29 | NC-C₆H₄- | 7-F₃CO-imidazo[1,2-a]pyridin-2-yl | --cyclopropyl-- |
| 576 | A29 | pyridin-4-yl | 7-F₃CO-imidazo[1,2-a]pyridin-2-yl | --cyclopropyl-- |
| 577 | A29 | MeO-C₆H₄- | 7-NC-imidazo[1,2-a]pyridin-2-yl | --cyclopropyl-- |
| 578 | A29 | NC-C₆H₄- | 7-NC-imidazo[1,2-a]pyridin-2-yl | --cyclopropyl-- |
| 579 | A29 | pyridin-4-yl | 7-NC-imidazo[1,2-a]pyridin-2-yl | --cyclopropyl-- |
| 580 | A29 | MeO-C₆H₄- | imidazo[1,2-b]pyridazin-6-yl | --cyclopropyl-- |
| 581 | A29 | NC-C₆H₄- | imidazo[1,2-b]pyridazin-6-yl | --cyclopropyl-- |

-continued
| Example # | HET | X | Z | R₂ |
|---|---|---|---|---|
| 582 | A29 | 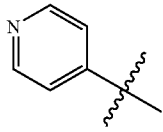 [SMILES: *c1ccncc1] | 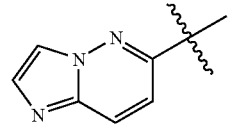 [SMILES: *c1ccc2nccn2n1] | --cyclopropyl-- |
| 583 | A29 | 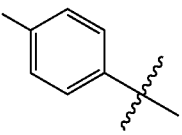 | 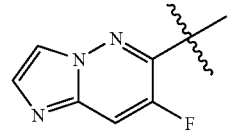 [SMILES: *c1nn2ccnc2cc1F] | --cyclopropyl-- |
| 584 | A29 | 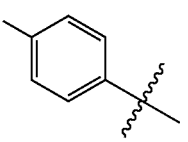 | 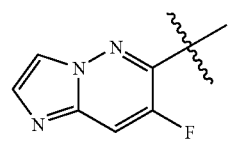 | --cyclopropyl-- |
| 585 | A29 | 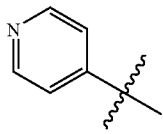 | 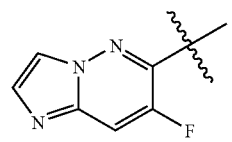 [SMILES: *c1nn2ccnc2cc1F] | --cyclopropyl-- |
| 586 | A29 | 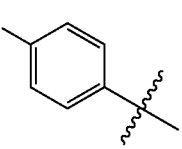 | 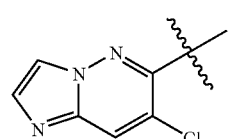 | --cyclopropyl-- |
| 587 | A29 | 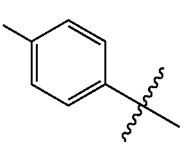 | 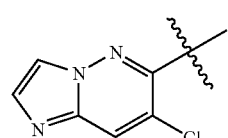 [SMILES: *c1nn2ccnc2cc1C] | --cyclopropyl-- |
| 588 | A29 | 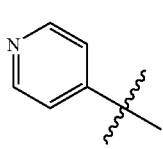 [SMILES: *c1ccncc1] | 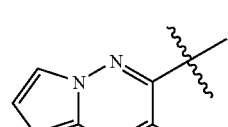 | --cyclopropyl-- |
| 589 | A29 | 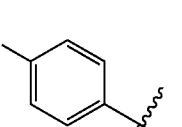 | 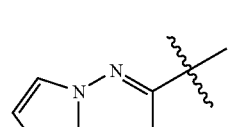 | --cyclopropyl-- |
| 590 | A29 | 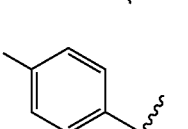 | 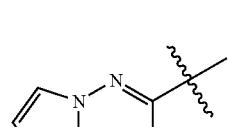 | --cyclopropyl-- |
| 591 | A29 | 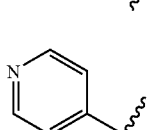 | 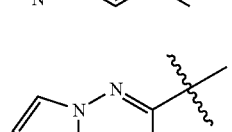 | --cyclopropyl-- |

-continued
| Example # | HET | X | Z | R₂ |
|---|---|---|---|---|
| 592 | A29 |  | 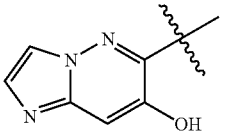 | --cyclopropyl-- |
| 593 | A29 |  | 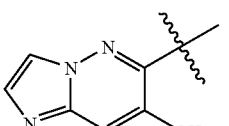 | --cyclopropyl-- |
| 594 | A29 | 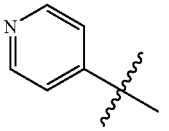 [SMILES: *c1ccncc1] | 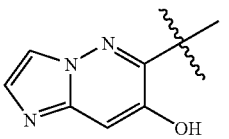 | --cyclopropyl-- |
| 595 | A29 |  | 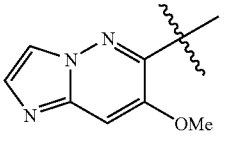 [SMILES: *c1nn2ccnc2cc1OC] | --cyclopropyl-- |
| 596 | A29 |  | 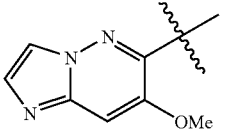 [SMILES: *c1nn2ccnc2cc1OC] | --cyclopropyl-- |
| 597 | A29 | 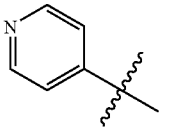 | 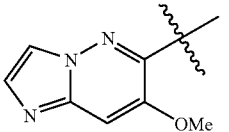 | --cyclopropyl-- |
| 598 | A29 |  | 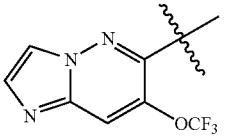 [SMILES: *c1nn2ccnc2cc1OC(F)(F)F] | --cyclopropyl-- |
| 599 | A29 |  | 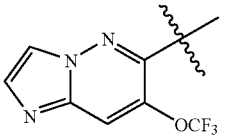 [SMILES: *c1nn2ccnc2cc1OC(F)(F)F] | --cyclopropyl-- |
| 600 | A29 | 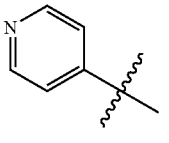 | 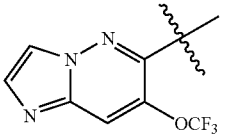 [SMILES: *c1nn2ccnc2cc1OC(F)(F)F] | --cyclopropyl-- |
| 601 | A29 |  | 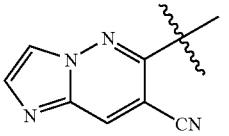 | --cyclopropyl-- |

-continued
| Example # | HET | X | Z | R₂ |
|---|---|---|---|---|
| 602 | A29 | 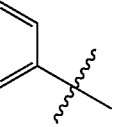 | 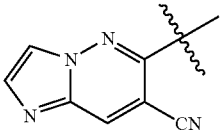 | --cyclopropyl-- |
| 603 | A29 | 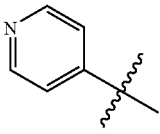 [SMILES: *c1ccncc1] | 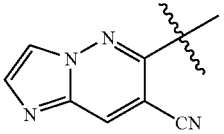 [SMILES: *c1nn2ccnc2cc1C#N] | --cyclopropyl-- |
| 604 | A29 | 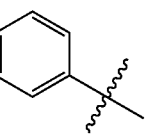 | 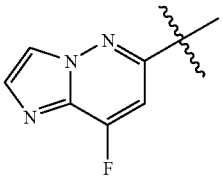 | --cyclopropyl-- |
| 605 | A29 | 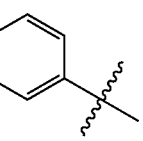 | 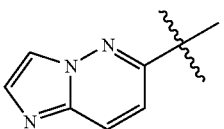 | --cyclopropyl-- |
| 606 | A29 | 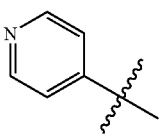 [SMILES: *c1ccncc1] | 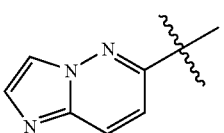 | --cyclopropyl-- |
| 607 | A29 | 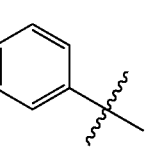 | 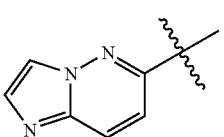 | --cyclopropyl-- |
| 608 | A29 |  | 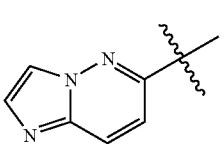 | --cyclopropyl-- |
| 609 | A29 | 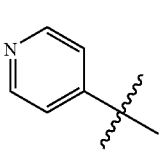 [SMILES: *c1ccncc1] | 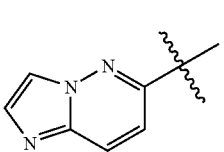 | --cyclopropyl-- |

-continued
| Example # | HET | X | Z | R$_2$ |
|---|---|---|---|---|
| 610 | A29 | 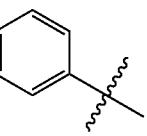 | 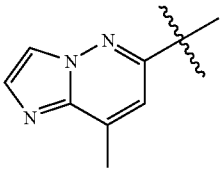 [SMILES: *c1cc(C)c2nccn2n1] | --cyclopropyl-- |
| 611 | A29 | 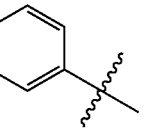 | 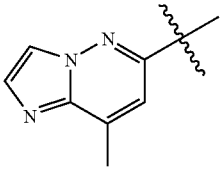 [SMILES: *c1cc(C)c2nccn2n1] | --cyclopropyl-- |
| 612 | A29 | 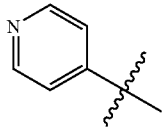 | 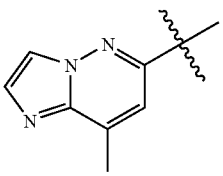 [SMILES: *c1cc(C)c2nccn2n1] | --cyclopropyl-- |
| 613 | A29 | 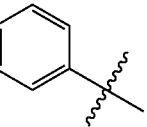 | 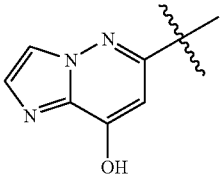 | --cyclopropyl-- |
| 614 | A29 | 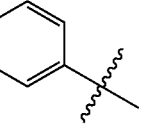 | 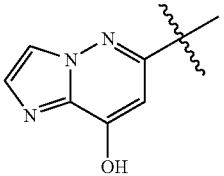 | --cyclopropyl-- |
| 615 | A29 | 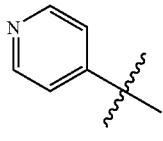 [SMILES: *c1ccncc1] | 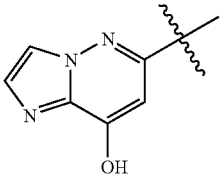 | --cyclopropyl-- |
| 616 | A29 | 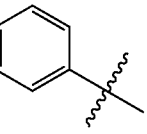 | 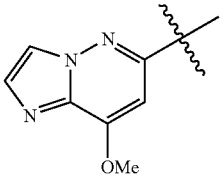 [SMILES: *c1cc(OC)c2nccn2n1] | --cyclopropyl-- |
| 617 | A29 | 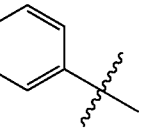 | 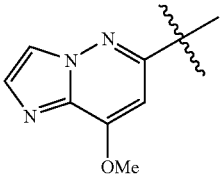 [SMILES: *c1cc(OC)c2nccn2n1] | --cyclopropyl-- |

| Example # | HET | X | Z | R₂ |
|---|---|---|---|---|
| 618 | A29 | 4-pyridyl | 6-(imidazo[1,2-b]pyridazin-6-yl), 8-OMe | --cyclopropyl-- |
| 619 | A29 | 4-MeO-phenyl | 6-(imidazo[1,2-b]pyridazin-6-yl), 8-OCF₃ | --cyclopropyl-- |
| 620 | A29 | 4-NC-phenyl | 6-(imidazo[1,2-b]pyridazin-6-yl), 8-OCF₃ | --cyclopropyl-- |
| 621 | A29 | 4-pyridyl | 6-(imidazo[1,2-b]pyridazin-6-yl), 8-OCF₃ | --cyclopropyl-- |
| 622 | A29 | 4-MeO-phenyl | 6-(imidazo[1,2-b]pyridazin-6-yl), 8-CN | --cyclopropyl-- |
| 623 | A29 | 4-NC-phenyl | 6-(imidazo[1,2-b]pyridazin-6-yl), 8-CN | --cyclopropyl-- |
| 624 | A29 | 4-pyridyl | 6-(imidazo[1,2-b]pyridazin-6-yl), 8-CN | --cyclopropyl-- |
| 625 | A29 | 4-MeO-phenyl | 6-(imidazo[1,2-b]pyridazin-6-yl), 2-F | --cyclopropyl-- |

-continued
| Example # | HET | X | Z | R₂ |
|---|---|---|---|---|
| 626 | A29 | 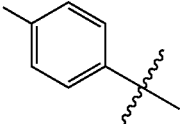 | 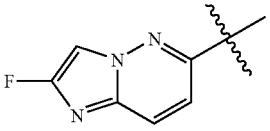 [SMILES: *c1ccc2nc(F)cn2n1] | --cyclopropyl-- |
| 627 | A29 | 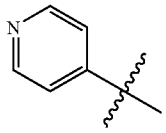 [SMILES: *c1ccncc1] | 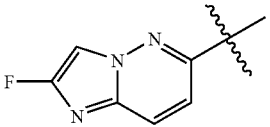 [SMILES: *c1ccc2nc(F)cn2n1] | --cyclopropyl-- |
| 628 | A29 | 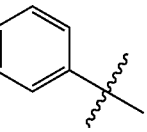 | 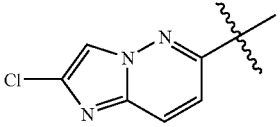 [SMILES: *c1ccc2nc(Cl)cn2n1] | --cyclopropyl-- |
| 629 | A29 | 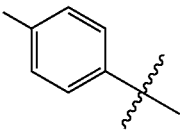 | 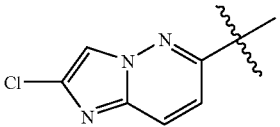 [SMILES: *c1ccc2nc(Cl)cn2n1] | --cyclopropyl-- |
| 630 | A29 | 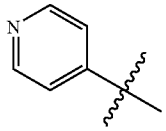 | 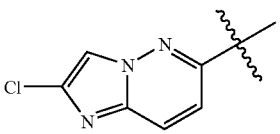 [SMILES: *c1ccc2nc(Cl)cn2n1] | --cyclopropyl-- |
| 631 | A29 | 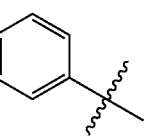 | 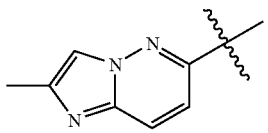 [SMILES: *c1ccc2nc(C)cn2n1] | --cyclopropyl-- |
| 632 | A29 | 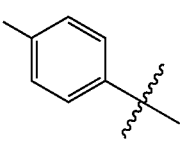 | 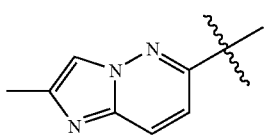 [SMILES: *c1ccc2nc(C)cn2n1] | --cyclopropyl-- |
| 633 | A29 | 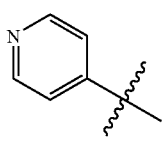 | 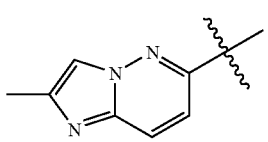 [SMILES: *c1ccc2nc(C)cn2n1] | --cyclopropyl-- |
| 634 | A29 | 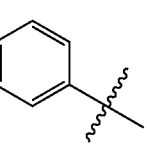 | 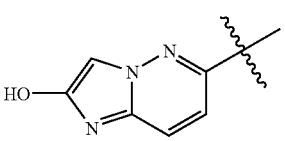 [SMILES: *c1ccc2nc(O)cn2n1] | --cyclopropyl-- |
| 635 | A29 | 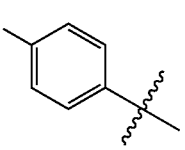 | 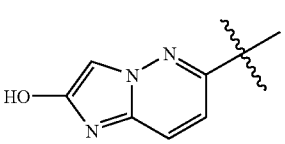 [SMILES: *c1ccc2nc(O)cn2n1] | --cyclopropyl-- |

| Example # | HET | X | Z | R₂ |
|---|---|---|---|---|
| 636 | A29 | 4-pyridyl | 2-hydroxy-imidazo[1,2-b]pyridazin-6-yl | --cyclopropyl-- |
| 637 | A29 | 4-MeO-phenyl | 2-MeO-imidazo[1,2-b]pyridazin-6-yl | --cyclopropyl-- |
| 638 | A29 | 4-NC-phenyl | 2-MeO-imidazo[1,2-b]pyridazin-6-yl | --cyclopropyl-- |
| 639 | A29 | 4-pyridyl | 2-MeO-imidazo[1,2-b]pyridazin-6-yl | --cyclopropyl-- |
| 640 | A29 | 4-MeO-phenyl | 2-F₃CO-imidazo[1,2-b]pyridazin-6-yl | --cyclopropyl-- |
| 641 | A29 | 4-NC-phenyl | 2-F₃CO-imidazo[1,2-b]pyridazin-6-yl | --cyclopropyl-- |
| 642 | A29 | 4-pyridyl | 2-F₃CO-imidazo[1,2-b]pyridazin-6-yl | --cyclopropyl-- |
| 643 | A29 | 4-MeO-phenyl | 2-NC-imidazo[1,2-b]pyridazin-6-yl | --cyclopropyl-- |
| 644 | A29 | 4-NC-phenyl | 2-NC-imidazo[1,2-b]pyridazin-6-yl | --cyclopropyl-- |
| 645 | A29 | 4-pyridyl | 2-NC-imidazo[1,2-b]pyridazin-6-yl | --cyclopropyl-- |

-continued

| Example # | HET | X | Z | R$_2$ |
|---|---|---|---|---|
| 646 | A29 | 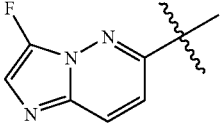 MeO-C$_6$H$_4$- | 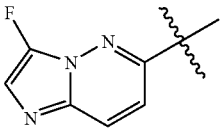 [SMILES: *c1ccc2ncc(F)n2n1] 3-F-imidazo[1,2-b]pyridazine | --cyclopropyl-- |
| 647 | A29 | NC-C$_6$H$_4$- | 3-F-imidazo[1,2-b]pyridazine | --cyclopropyl-- |
| 648 | A29 | 4-pyridyl | 3-F-imidazo[1,2-b]pyridazine | --cyclopropyl-- |
| 649 | A29 | MeO-C$_6$H$_4$- | 3-Cl-imidazo[1,2-b]pyridazine | --cyclopropyl-- |
| 650 | A29 | NC-C$_6$H$_4$- | 3-Cl-imidazo[1,2-b]pyridazine | --cyclopropyl-- |
| 651 | A29 | 4-pyridyl | 3-Cl-imidazo[1,2-b]pyridazine | --cyclopropyl-- |
| 652 | A29 | MeO-C$_6$H$_4$- | 3-Me-imidazo[1,2-b]pyridazine | --cyclopropyl-- |
| 653 | A29 | NC-C$_6$H$_4$- | 3-Me-imidazo[1,2-b]pyridazine | --cyclopropyl-- |
| 654 | A29 | 4-pyridyl | 3-Me-imidazo[1,2-b]pyridazine | --cyclopropyl-- |
| 655 | A29 | MeO-C$_6$H$_4$- | 3-HO-imidazo[1,2-b]pyridazine | --cyclopropyl-- |

-continued

| Example # | HET | X | Z | R₂ |
|---|---|---|---|---|
| 656 | A29 | 4-NC-phenyl | 3-HO-imidazo[1,2-b]pyridazin-6-yl | --cyclopropyl-- |
| 657 | A29 | pyridin-4-yl | 3-HO-imidazo[1,2-b]pyridazin-6-yl | --cyclopropyl-- |
| 658 | A29 | 4-MeO-phenyl | 3-MeO-imidazo[1,2-b]pyridazin-6-yl | --cyclopropyl-- |
| 659 | A29 | 4-NC-phenyl | 3-MeO-imidazo[1,2-b]pyridazin-6-yl | --cyclopropyl-- |
| 660 | A29 | pyridin-4-yl | 3-MeO-imidazo[1,2-b]pyridazin-6-yl | --cyclopropyl-- |
| 661 | A29 | 4-MeO-phenyl | 3-F₃CO-imidazo[1,2-b]pyridazin-6-yl | --cyclopropyl-- |
| 662 | A29 | 4-NC-phenyl | 3-F₃CO-imidazo[1,2-b]pyridazin-6-yl | --cyclopropyl-- |
| 663 | A29 | pyridin-4-yl | 3-F₃CO-imidazo[1,2-b]pyridazin-6-yl | --cyclopropyl-- |
| 664 | A29 | 4-MeO-phenyl | 3-NC-imidazo[1,2-b]pyridazin-6-yl | --cyclopropyl-- |
| 665 | A29 | 4-NC-phenyl | 3-NC-imidazo[1,2-b]pyridazin-6-yl | --cyclopropyl-- |

-continued

| Example # | HET | X | Z | R₂ |
|---|---|---|---|---|
| 666 | A29 | 4-pyridyl | 3-cyano-imidazo[1,2-b]pyridazin-6-yl | --cyclopropyl-- |
| 667 | A29 | 4-methoxyphenyl | imidazo[1,2-b]pyridazin-2-yl | --cyclopropyl-- |
| 668 | A29 | 4-cyanophenyl | imidazo[1,2-b]pyridazin-2-yl | --cyclopropyl-- |
| 669 | A29 | 4-pyridyl | imidazo[1,2-b]pyridazin-2-yl | --cyclopropyl-- |
| 670 | A29 | 4-methoxyphenyl | 3-fluoro-imidazo[1,2-b]pyridazin-2-yl | --cyclopropyl-- |
| 671 | A29 | 4-cyanophenyl | 3-fluoro-imidazo[1,2-b]pyridazin-2-yl | --cyclopropyl-- |
| 672 | A29 | 4-pyridyl | 3-fluoro-imidazo[1,2-b]pyridazin-2-yl | --cyclopropyl-- |
| 673 | A29 | 4-methoxyphenyl | 3-chloro-imidazo[1,2-b]pyridazin-2-yl | --cyclopropyl-- |
| 674 | A29 | 4-cyanophenyl | 3-chloro-imidazo[1,2-b]pyridazin-2-yl | --cyclopropyl-- |
| 675 | A29 | 4-pyridyl | 3-chloro-imidazo[1,2-b]pyridazin-2-yl | --cyclopropyl-- |

-continued
| Example # | HET | X | Z | R₂ |
|---|---|---|---|---|
| 676 | A29 | 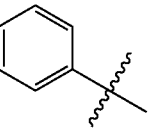 | 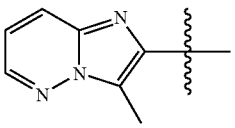 | --cyclopropyl-- |
| 677 | A29 | 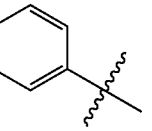 | 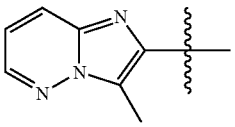 | --cyclopropyl-- |
| 678 | A29 | 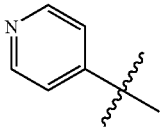 [SMILES: *c1ccncc1] | 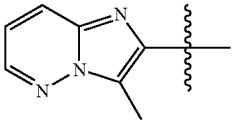 [SMILES: *c1nc2cccnn2c1C] | --cyclopropyl-- |
| 679 | A29 | 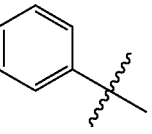 | 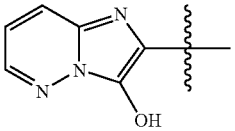 | --cyclopropyl-- |
| 680 | A29 | 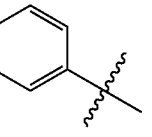 | 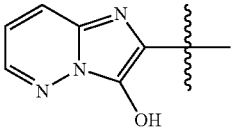 | --cyclopropyl-- |
| 681 | A29 | 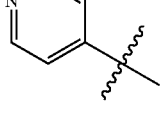 | 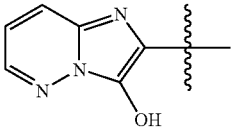 | --cyclopropyl-- |
| 682 | A29 | 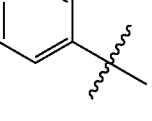 | 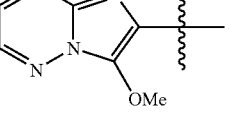 | --cyclopropyl-- |
| 683 | A29 | 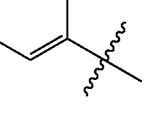 | 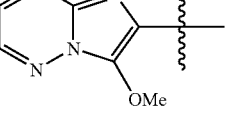 | --cyclopropyl-- |
| 684 | A29 | 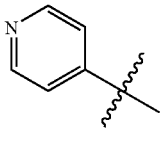 [SMILES: *c1ccncc1] | 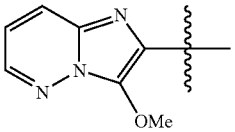 | --cyclopropyl-- |
| 685 | A29 | 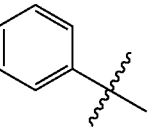 | 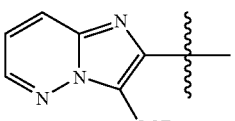 | --cyclopropyl-- |

-continued

| Example # | HET | X | Z | R₂ |
|---|---|---|---|---|
| 686 | A29 | 4-cyanophenyl | imidazo[1,2-b]pyridazin-2-yl, 3-OCF₃ | --cyclopropyl-- |
| 687 | A29 | pyridin-4-yl | imidazo[1,2-b]pyridazin-2-yl, 3-OCF₃ | --cyclopropyl-- |
| 688 | A29 | 4-methoxyphenyl | imidazo[1,2-b]pyridazin-2-yl, 3-CN | --cyclopropyl-- |
| 689 | A29 | 4-cyanophenyl | imidazo[1,2-b]pyridazin-2-yl, 3-CN | --cyclopropyl-- |
| 690 | A29 | pyridin-4-yl | imidazo[1,2-b]pyridazin-2-yl, 3-CN | --cyclopropyl-- |
| 691 | A29 | 4-methoxyphenyl | 6-fluoroimidazo[1,2-b]pyridazin-2-yl | --cyclopropyl-- |
| 692 | A29 | 4-cyanophenyl | 6-fluoroimidazo[1,2-b]pyridazin-2-yl | --cyclopropyl-- |
| 693 | A29 | pyridin-4-yl | 6-fluoroimidazo[1,2-b]pyridazin-2-yl | --cyclopropyl-- |
| 694 | A29 | 4-methoxyphenyl | 6-chloroimidazo[1,2-b]pyridazin-2-yl | --cyclopropyl-- |
| 695 | A29 | 4-cyanophenyl | 6-chloroimidazo[1,2-b]pyridazin-2-yl | --cyclopropyl-- |

-continued

| Example # | HET | X | Z | R₂ |
|---|---|---|---|---|
| 696 | A29 | 4-pyridyl | 6-chloro-imidazo[1,2-b]pyridazin-2-yl | --cyclopropyl-- |
| 697 | A29 | 4-methoxyphenyl | 6-methyl-imidazo[1,2-b]pyridazin-2-yl | --cyclopropyl-- |
| 698 | A29 | 4-cyanophenyl | 6-methyl-imidazo[1,2-b]pyridazin-2-yl | --cyclopropyl-- |
| 699 | A29 | 4-pyridyl | 6-methyl-imidazo[1,2-b]pyridazin-2-yl | --cyclopropyl-- |
| 700 | A29 | 4-methoxyphenyl | 6-hydroxy-imidazo[1,2-b]pyridazin-2-yl | --cyclopropyl-- |
| 701 | A29 | 4-cyanophenyl | 6-hydroxy-imidazo[1,2-b]pyridazin-2-yl | --cyclopropyl-- |
| 702 | A29 | 4-pyridyl | 6-hydroxy-imidazo[1,2-b]pyridazin-2-yl | --cyclopropyl-- |
| 703 | A29 | 4-methoxyphenyl | 6-methoxy-imidazo[1,2-b]pyridazin-2-yl | --cyclopropyl-- |
| 704 | A29 | 4-cyanophenyl | 6-methoxy-imidazo[1,2-b]pyridazin-2-yl | --cyclopropyl-- |
| 705 | A29 | 4-pyridyl | 6-methoxy-imidazo[1,2-b]pyridazin-2-yl | --cyclopropyl-- |

-continued
| Example # | HET | X | Z | R₂ |
|---|---|---|---|---|
| 706 | A29 |  | 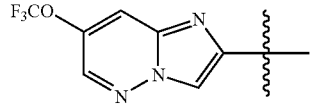 | --cyclopropyl-- |
| 707 | A29 |  | 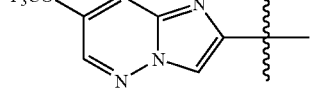 | --cyclopropyl-- |
| 708 | A29 | 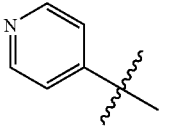 [SMILES: *c1ccncc1] | 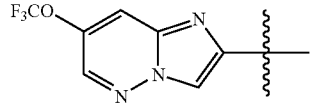 [SMILES: *c1cn2ncc(OC(F)(F)F)cc2n1] | --cyclopropyl-- |
| 709 | A29 |  | 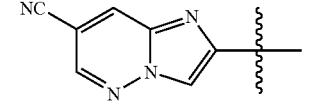 | --cyclopropyl-- |
| 710 | A29 |  | 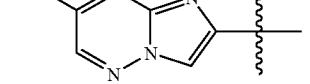 | --cyclopropyl-- |
| 711 | A29 | 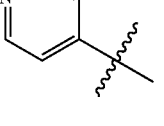 | 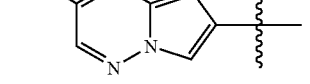 | --cyclopropyl-- |
| 712 | A29 | 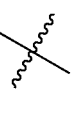 | 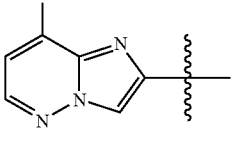 | --cyclopropyl-- |
| 713 | A29 | 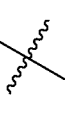 | 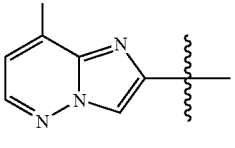 | --cyclopropyl-- |
| 714 | A29 | 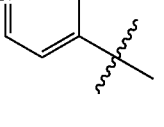 | 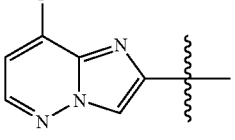 | --cyclopropyl-- |
| 715 | A29 |  | 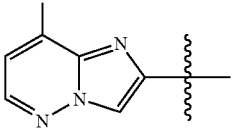 | --cyclopropyl-- |

-continued

| Example # | HET | X | Z | R₂ |
|---|---|---|---|---|
| 716 | A29 | 4-NC-phenyl | 8-Cl-imidazo[1,2-b]pyridazin-2-yl | --cyclopropyl-- |
| 717 | A29 | pyridin-4-yl | 8-Cl-imidazo[1,2-b]pyridazin-2-yl | --cyclopropyl-- |
| 718 | A29 | 4-MeO-phenyl | 8-Me-imidazo[1,2-b]pyridazin-2-yl | --cyclopropyl-- |
| 719 | A29 | 4-NC-phenyl | 8-Me-imidazo[1,2-b]pyridazin-2-yl | --cyclopropyl-- |
| 720 | A29 | pyridin-4-yl | 8-Me-imidazo[1,2-b]pyridazin-2-yl | --cyclopropyl-- |
| 721 | A29 | 4-MeO-phenyl | 8-OH-imidazo[1,2-b]pyridazin-2-yl | --cyclopropyl-- |
| 722 | A29 | 4-NC-phenyl | 8-OH-imidazo[1,2-b]pyridazin-2-yl | --cyclopropyl-- |
| 723 | A29 | pyridin-4-yl | 8-OH-imidazo[1,2-b]pyridazin-2-yl | --cyclopropyl-- |
| 724 | A29 | 4-MeO-phenyl | 8-OMe-imidazo[1,2-b]pyridazin-2-yl | --cyclopropyl-- |

-continued

| Example # | HET | X | Z | R₂ |
|---|---|---|---|---|
| 725 | A29 | 4-cyanophenyl | 8-OMe-imidazo[1,2-b]pyridazin-2-yl | --cyclopropyl-- |
| 726 | A29 | pyridin-4-yl | 8-OMe-imidazo[1,2-b]pyridazin-2-yl | --cyclopropyl-- |
| 727 | A29 | 4-MeO-phenyl | 8-OCF₃-imidazo[1,2-b]pyridazin-2-yl | --cyclopropyl-- |
| 728 | A29 | 4-cyanophenyl | 8-OCF₃-imidazo[1,2-b]pyridazin-2-yl | --cyclopropyl-- |
| 729 | A29 | pyridin-4-yl | 8-OCF₃-imidazo[1,2-b]pyridazin-2-yl | --cyclopropyl-- |
| 730 | A29 | 4-MeO-phenyl | 8-CN-imidazo[1,2-b]pyridazin-2-yl | --cyclopropyl-- |
| 731 | A29 | 4-cyanophenyl | 8-CN-imidazo[1,2-b]pyridazin-2-yl | --cyclopropyl-- |
| 732 | A29 | pyridin-4-yl | 8-CN-imidazo[1,2-b]pyridazin-2-yl | --cyclopropyl-- |

DOSAGE AND ADMINISTRATION

The present disclosure includes pharmaceutical composition for treating a subject having a neurological disorder comprising a therapeutically effective amount of a compound of Formula (I), a derivative or a pharmaceutically acceptable salt thereof, and a pharmaceutically acceptable excipient, carrier or diluent.

The pharmaceutical compositions can be administered in a variety of dosage forms including, but not limited to, a solid dosage form or in a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The dosage can be an oral dosage form that is a controlled release dosage form. The oral dosage form can be a tablet or a caplet. The compounds can be administered, for example, by oral or parenteral routes, including intravenous, intramuscular, intraperitoneal, subcutaneous, transdermal, airway (aerosol), rectal, vaginal and topical (including buccal and sublingual) administration. In one embodiment, the compounds or pharmaceutical compositions comprising the compounds are delivered to a desired site, such as the brain, by continuous injection via a shunt.

In another embodiment, the compound can be administered parenterally, such as intravenous (IV) administration. The formulations for administration will commonly comprise a solution of the compound of the Formula (I) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of compound of Formula (I) in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment, a compound of Formula (I) can be administered by introduction into the central nervous system of the subject, e.g., into the cerbrospinal fluid of the subject. The formulations for administration will commonly comprise a solution of the compound of Formula (I) dissolved in a pharmaceutically acceptable carrier. In certain aspects, the compound of Formula (I) is introduced intrathecally, e.g., into a cerebral ventricle, the lumbar area, or the cisterna magna. In another aspect, the compound of Formula (I) is introduced intraocularly, to thereby contact retinal ganglion cells.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

In one embodiment, the pharmaceutical composition comprising a compound of Formula (I) is administered into a subject intrathecally. As used herein, the term "intrathecal administration" is intended to include delivering a pharmaceutical composition comprising a compound of Formula (I) directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a compound of Formula (I) to any of the above mentioned sites can be achieved by direct injection of the pharmaceutical composition comprising the compound of Formula (I) or by the use of infusion pumps. For injection, the pharmaceutical compositions can be formulated in liquid solutions, preferably in physiologically compatible buffers such as Hank's solution or Ringer's solution. In addition, the pharmaceutical compositions may be formulated in solid form and re-dissolved or suspended immediately prior to use. Lyophilized forms are also included. The injection can be, for example, in the form of a bolus injection or continuous infusion (e.g., using infusion pumps) of pharmaceutical composition.

In one embodiment, the pharmaceutical composition comprising a compound of Formula (I) is administered by lateral cerebro ventricular injection into the brain of a subject. The injection can be made, for example, through a burr hole made in the subject's skull. In another embodiment, the encapsulated therapeutic agent is administered through a surgically inserted shunt into the cerebral ventricle of a subject. For example, the injection can be made into the lateral ventricles, which are larger, even though injection into the third and fourth smaller ventricles can also be made.

In yet another embodiment, the pharmaceutical composition is administered by injection into the cisterna magna, or lumbar area of a subject.

For oral administration, the compounds will generally be provided in unit dosage foams of a tablet, pill, dragee, lozenge or capsule; as a powder or granules; or as an aqueous solution, suspension, liquid, gels, syrup, slurry, etc. suitable for ingestion by the patient. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical preparations for oral use can be obtained through combination of a compound of Formula (I) with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethylcellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For transmucosal administration (e.g., buccal, rectal, nasal, ocular, etc.), penetrants appropriate to the barrier to be permeated are used in the formulation. Such penetrants are generally known in the art.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the compounds will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The suppositories for rectal administration of the drug can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds can be delivered transdermally, by a topical route, formulated as applicator sticks, solutions, suspensions, emulsions, gels, creams, ointments, pastes, jellies, paints, powders, or aerosols.

The compounds may also be presented as aqueous or liposome formulations. Aqueous suspensions can contain a compound of Formula (I) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a compound of Formula (I) in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In general a suitable dose will be in the range of 0.01 to 100 mg per kilogram body weight of the recipient per day, preferably in the range of 0.1 to 10 mg per kilogram body weight per day. The desired dose is preferably presented once daily, but may be dosed as two, three, four, five, six or more subdoses administered at appropriate intervals throughout the day.

The compounds can be administered as the sole active agent, or in combination with other known therapeutics to be beneficial in the treatment of neurological disorders. In any event, the administering physician can provide a method of treatment that is prophylactic or therapeutic by adjusting the amount and timing of drug administration on the basis of observations of one or more symptoms (e.g., motor or cognitive function as measured by standard clinical scales or assessments) of the disorder being treated. Details on techniques for formulation and administration are well described in the scientific and patent literature, see, e.g., the latest edition of Remington's Pharmaceutical Sciences, Maack Publishing Co, Easton Pa. After a pharmaceutical composition has been formulated in an acceptable carrier, it can be placed in an appropriate container and labeled for treatment of an indicated condition. For administration of the compounds of Formula (I), such labeling would include, e.g., instructions concerning the amount, frequency and method of administration.

BIOLOGICAL EXAMPLES

In Vivo Methods

Subjects: Male C57BL/6J mice (Charles River; 20-25 g) were used for all assays except prepulse inhibition (PPI) which used male DBA/2N mice (Charles River, 20-25 g). For all studies, animals were housed five/cage on a 12-h light/dark cycle with food and water available ad libitum.

Conditioned avoidance responding: Testing was performed in commercially available avoidance boxes (Kinder Scientific, Poway Calif.). The boxes were divided into two compartments separated by an archway. Each side of the chamber has electronic grid flooring that is equipped to administer footshocks and an overhead light. Training consisted of repeated pairings of the light (conditioned stimulus) followed by a shock (unconditioned stimulus). For each trial the light was presented for 5 sec followed by a 0.5 mA shock that would terminate if the mouse crossed to the other chamber or after 10 seconds. The intertrial interval was set to 20 seconds. Each training and test session consisted a four min habituation period followed by 30 trials. The number of avoidances (mouse crossed to other side during presentation of the light), escapes (mouse crossed to the other side during presentation of the shock) and failures (mouse did not cross during the entire trial period) were recorded by a computer. For study inclusion an animal had to reach a criterion of at least 80% avoidances for two consecutive test sessions.

PPI: Mice were individually placed into the test chambers (StartleMonitor, Kinder Scientific, Poway Calif.). The animals were given a five min acclimation period to the test chambers with the background noise level set to 65 decibel (dB) which remained for the entire test session. Following acclimation, four successive trials 120 dB pulse for 40 msec were presented, however these trials were not included in data analysis. The mice were then subjected to five different types of trials in random order: pulse alone (120 dB for 40 msec), no stimulus and three different prepulse+pulse trials with the prepulse set at 67, 69 or 74 dB for 20 msec followed a 100 msec later by a 120 dB pulse for 40 msec. Each animal received 12 trials for each condition for a total of 60 trials with an average intertrial interval of 15 sec. Percent PPI was calculated according to the following formula: (1−(startle response to prepulse+pulse)/startle response to pulse alone))×100.

MK-801-induced hyperactivity: After a 30 min acclimatation to the test room mice were individually placed into test cages for a 30 min habituation period. Following habituation to test cages, baseline activity was recorded for 60 min. Mice were then briefly removed and administered test compound and placed immediately back into the test cage. At 5 min prior to test time mice were again briefly removed from test cages and administered MK-801 (0.3 mg/kg, i.p. in 0.9% saline) and then immediately placed back into test cages and activity level recorded 1 hour. Activity level was measured as distance traveled in centimeters (Ethovision tracking software, Noldus Inc. Wageningen, Netherlands).

Catalepsy: Mice were placed on a wire mesh screen set at a 60 degree angle with their heads facing upwards and the latency to move or break stance was recorded. Animals were given three trials per time point with a 30 sec cut-off per trial.

Data analysis: A one-way or two-way ANOVA was used to evaluate overall differences between treatments and a Tukey's post-hoc test or Student's t-test was used to evaluate differences between treatment groups for the one-way ANOVA and a Bonferroni test was used for the two-way ANOVA. The criterion for statistical significance was set to $p<0.05$.

In Vitro Methods hPDE10A1 Enzyme Activity: 50 µl samples of serially diluted Human PDE10A1 enzyme were incubated with 50 µl of [$^3$H]-cAMP for 20 minutes (at 37° C.). Reactions were carried out in Greiner 96 deep well 1 ml master-block. The enzyme was diluted in 20 mM Tris HCl pH7.4 and [$^3$H]-cAMP was diluted in 10 mM MgCl$_2$, 40 mM Tris.HCl pH 7.4. The reaction was terminated by denaturing the PDE enzyme (at 70° C.) after which [$^3$H]-5'-AMP was converted to [$^3$H]-adenosine by adding 25 µl snake venom nucleotidase and incubating for 10 minutes (at 37° C.). Adenosine, being neutral, was separated from charged cAMP or AMP by the addition of 200 µl Dowex resin. Samples were shaken for 20 minutes then centrifuged for 3 minutes at 2,500 r.p.m. 50 µl of supernatant was removed and added to 200 µl of MicroScint-20 in white plates (Greiner 96-well Optiplate) and shaken for 30 minutes before reading on Perkin Elmer TopCount Scintillation Counter.

hPDE10A1 Enzyme Inhibition: To check inhibition profile 11 µl of serially diluted inhibitor was added to 50 µl of [$^3$H]-cAMP and 50 ul of diluted Human PDE10A1 and assay was carried out as in the enzyme activity assay. Data was analysed using Prism software (GraphPad Inc). Representative compounds of this disclosure are shown in the table below. A compound with the value "A" had an IC$_{50}$ value less than or equal to 10 nM. A compound with the value "B" had an IC$_{50}$ value greater than 10 nM and less than 50 nM:

| Name | hPDE10A1 IC$_{50}$ Band |
|---|---|
| 4-(4-((3,5-dimethylpyridin-2-yl)methoxy)phenyl)-5-(4-methoxyphenyl)-2,2-dimethylfuran-3(2H)-one | A |
| 4-(4-(imidazo[1,2-a]pyridin-2-ylmethoxy)phenyl)-5-(4-methoxyphenyl)-2,2-dimethylfuran-3(2H)-one | A |
| 4-(4-(imidazo[1,2-b]pyridazin-6-ylmethoxy)phenyl)-5-(4-methoxyphenyl)-2,2-dimethylfuran-3(2H)-one | B |
| 4-(4-((6-chloroimidazo[1,2-b]pyridazin-2-yl)methoxy)phenyl)-5-(4-methoxyphenyl)-2,2-dimethylfuran-3(2H)-one | B |
| 4-(4-(imidazo[1,2-b]pyridazin-2-ylmethoxy)phenyl)-5-(4-methoxyphenyl)-2,2-dimethylfuran-3(2H)-one | A |
| 4-(3-(4-(imidazo[1,2-a]pyridin-2-ylmethoxy)phenyl)-5,5-dimethyl-4-oxo-4,5-dihydrofuran-2-yl)benzonitrile | A |

-continued

| Name | hPDE10A1 IC$_{50}$ Band |
|---|---|
| 4-(4-((3-chloroimidazo[1,2-a]pyridin-2-yl)methoxy)phenyl)-5-(4-methoxyphenyl)-2,2-dimethylfuran-3(2H)-one | A |
| 5-(4-methoxyphenyl)-2,2-dimethyl-4-(4-((5-methylpyridin-2-yl)methoxy)phenyl)furan-3(2H)-one | A |
| 4-(5,5-dimethyl-3-(4-((5-methylpyridin-2-yl)methoxy)phenyl)-4-oxo-4,5-dihydrofuran-2-yl)benzonitrile | A |
| 4-(4-((6-chloroimidazo[1,2-a]pyridin-2-yl)methoxy)phenyl)-5-(4-methoxyphenyl)-2,2-dimethylfuran-3(2H)-one | A |
| 5-(4-methoxyphenyl)-2,2-dimethyl-4-(4-((3-methylimidazo[1,2-a]pyridin-2-yl)methoxy)phenyl)furan-3(2H)-one | B |
| 5-(4-methoxyphenyl)-2,2-dimethyl-4-(4-((5-methylimidazo[1,2-a]pyridin-2-yl)methoxy)phenyl)furan-3(2H)-one | A |

What is claimed is:

1. 4-(4-(imidazo[1,2-b]pyridazin-2-ylmethoxy)phenyl)-2,2-dimethyl-5-(pyridin-4-yl)furan-3(2H)-one.

2. A pharmaceutically acceptable salt of 4-(4-(imidazo[1,2-b]pyridazin-2-ylmethoxy)phenyl)-2,2-dimethyl-5-(pyridin-4-yl)furan-3(2H)-one.

3. A pharmaceutical composition comprising:
   (i) 4-(4-(imidazo[1,2-b]pyridazin-2-ylmethoxy)phenyl)-2,2-dimethyl-5-(pyridin-4-yl)furan-3(2H)-one; and
   (ii) a pharmaceutically acceptable carrier or excipient.

4. A pharmaceutical composition comprising:
   (i) a pharmaceutically acceptable salt of 4-(4-(imidazo[1,2-b]pyridazin-2-ylmethoxy)phenyl)-2,2-dimethyl-5-(pyridin-4-yl)furan-3(2H)-one; and
   (ii) a pharmaceutically acceptable carrier or excipient.

\* \* \* \* \*